US011299545B2

(12) United States Patent
Eberwine et al.

(10) Patent No.: US 11,299,545 B2
(45) Date of Patent: Apr. 12, 2022

(54) ANTI-HLA-C ANTIBODIES AND USES THEREOF

(71) Applicant: Janssen Biotech, Inc., Horsham, PA (US)

(72) Inventors: Ryan Eberwine, Philadelphia, PA (US); Anne Fourie, San Diego, CA (US); Paul H. Kim, Del Mar, CA (US); Carl L. Manthey, Chester Springs, PA (US); Hong Zhou, San Diego, CA (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 16/839,179

(22) Filed: Apr. 3, 2020

(65) Prior Publication Data

US 2020/0317791 A1 Oct. 8, 2020

Related U.S. Application Data

(60) Provisional application No. 62/829,282, filed on Apr. 4, 2019.

(51) Int. Cl.
  *C07K 16/28* (2006.01)
  *A61K 38/00* (2006.01)
(52) U.S. Cl.
  CPC .......... *C07K 16/2833* (2013.01); *A61K 38/00* (2013.01); *C07K 2317/24* (2013.01); *C07K 2317/565* (2013.01)
(58) Field of Classification Search
  CPC .................................................. C07K 16/2833
  See application file for complete search history.

(56) References Cited

U.S. PATENT DOCUMENTS

| | | | | |
|---|---|---|---|---|
| 2005/0049402 | A1* | 3/2005 | Babcook | A61P 29/00 530/388.23 |
| 2014/0088295 | A1* | 3/2014 | Smith | A61P 37/04 530/387.3 |
| 2014/0114054 | A1 | 4/2014 | Kurosawa et al. | |
| 2017/0088620 | A1* | 3/2017 | Nioi | A61P 3/06 |
| 2018/0355043 | A1* | 12/2018 | Martinez | A61P 19/02 |

FOREIGN PATENT DOCUMENTS

| | | | |
|---|---|---|---|
| WO | WO-2009040134 A1 * | 4/2009 | ............. A61P 11/00 |
| WO | WO 2017/106684 A2 | 6/2017 | |

OTHER PUBLICATIONS

Wang et al. "Human autoimmune diseases: a comprehensive update", J Intern Med. Oct. 2015;278(4):369-95 (Year: 2015).*
PCT Search Report dated Sep. 14, 2020.
Altschul et al., "Basic Local Alignment Search Tool," Journal of Molecular Biology, 215: 403-410 (1990).
Altschul et al., "Gapped BLAST and PSI-BLAST: a new generation of protein database search programs," Nucleic Acids Research, 25: 3389-3402 (1997).
Arakawa et al., "Melanocyte antigen triggers autoimmunity in human psoriasis," Journal of Experimental Medicine, 212(13):2203-2212 (2015).
Asumalahti et al., "Genetic Analysis of PSORS1 Distinguishes Guttate Psoriasis and palmoplantar Pustulosis," Journal of Investigative Dermatology, 120(4):627-632 (2003).
Besgen et al., "Ezrin, Maspin, Peroxiredoxin 2, and Heat Shock Protein 27: Potential Targets of a *Streptococcal*-Induced Autoimmune Response in Psoriasis," Journal of Immunology, 184(9):5392-5402 (2010).
Cairns et al., The Fine Specificity and Cytokine Profile of T-Helper Cells Responsive to the α3 Chain of Type IV Collagen in Goodpasture's Disease, Journal of American Soc. Nephrol., 14(11):2801-2812 (2003).
Elder et al., Molecular Dissection of Psoriasis: Integrating Genetics and Biology, Journal of Investigative Dermatology, 130(5):1213-1226 (2010).
Gudjonsson et al., "Psoriasis patients who are homozygous for the HLA-Cw*0602 allele have a 2·5-fold increased risk of developing psoriasis compared with Cw6 heterozygotes," British Journal of Dermatology, 148(2):233-235 (2003).
Gudjonsson et al., "Distinct Clinical Differences Between HLA-Cw*0602 Positive and Negative Psoriasis Patients—An Analysis of 1019 HLA-C- and LA-B-Typed Patients," Journal of Investigative Dermatology, 126(4):740-745 (2006).
Hayter, et al., "Updated assessment of the prevalence, spectrum and case definition of autoimmune disease," Autoimmune Reviews, 11(10):754-765 (2012).
Henikoff, et al., "Amino acid substitution matrices from protein blocks," Proceeding of the National Academy of Science USA, 89:10915-10919 (1989).
Her, et al., "Alterations in immune function with biologic therapies for autoimmune disease," Journal of Allergy and Clinical Immunology, 137(1): 19-27 (2016).
Karlin, et al., "Applications and statistics for multiple high-scoring segments in molecular sequences," Proceedings of the National Academy of Science USA, 90:5873-5787 (1993).
Kim et al., "Analysis of the Paired TCR α- and β-chains of Single Human T Cells," PLoS One 7(5):e37338 (2012).
Lande et al., "The antimicrobial peptide LL37 is a T-cell autoantigen in psoriasis," Nature Communications, 5(5621): 1-15 (2014).
Laydon et al., "Estimating T-cell repertoire diversity: limitations of classical estimators and a new approach," Philosophical Transactions Royal Society B, 370: 1-11 (2015).
Matzaraki et al., "The MHC locus and genetic susceptibility to autoimmune and infectious diseases," Genome Biology 18(76): 1-21 (2017).

(Continued)

*Primary Examiner* — Sharon X Wen
*Assistant Examiner* — Peter Johansen
(74) *Attorney, Agent, or Firm* — Eric Dichter

(57) ABSTRACT

Anti-HLA-C6 antibodies and antigen-binding fragments thereof are described. Also described are nucleic acids encoding the antibodies, compositions comprising the antibodies, methods of producing the antibodies, and methods of using the antibodies for treating or preventing diseases, such as autoimmune diseases.

14 Claims, 23 Drawing Sheets

Specification includes a Sequence Listing.

(56) References Cited

OTHER PUBLICATIONS

Nair et al., "Sequence and Haplotype Analysis Supports HLA-C as the Psoriasis Susceptibility 1 Gene," The American Journal of Human Genetics, 78(5):827-851 (2006).
Needleman, et al., "A General Method Applicable to the Search for Similarities in the Amino Acid Sequence of Two Proteins," Journal of Molecular Biology, 48:443-453 (1970).
Pearson, et al., "Improved tools for biological sequence comparison," Proceedings of the National Academy of Science USA, 85:2444-2448 (1988).
Temple F. Smith, "Comparison of Biosequences," Advances in Applied Mathematics, 2:482-489 (1981).
Strange et al., "Genome-wide association study identifies new psoriasis susceptibility loci and an interaction between HLA-C and ERAP1," Nature Genetics, 42(11):985-990 (2010).
Thomas, et al., "HLA-C Cell Surface Expression and Control of HIV/AIDS Correlate with a Variant Upstream of HLA-C," Nature Genetics, 41(12): 1-14 (2009).
John Trowsdale, "The MHC, disease and selection," Immunology Letters, 137:1-8 (2011).
Wolf, et al., "Biologic Therapies for Autoimmune and Connective Tissue Disease," Immunological Allergy Clinic North America, 37(2):283-299 (2017).
Yunusbaeva et al., "Psoriasis patients demonstrate HLA-Cw*06:02 allele dosage-dependent T cell proliferation when treated with hair follicle-derived keratin 17 protein," Scientific Reports, Scientific Reports, 8(6098): 1-7 (2018).

\* cited by examiner

ANTI-HLA-C ANTIBODIES AND USES THEREOF

CROSS-REFERENCE TO RELATED APPLICATIONS

This application claims the benefit of United States Provisional Application Ser. No. 62/829,282, filed 4 Apr. 2019. The entire contents of the aforementioned application is incorporated herein by reference in its entirety.

FIELD OF THE INVENTION

This invention relates to monoclonal anti-HLA-C antibodies, nucleic acids and expression vectors encoding the antibodies, recombinant cells containing the vectors, and compositions comprising the antibodies. Methods of making the antibodies, and methods of using the antibodies to treat diseases including psoriasis, are also provided.

REFERENCE TO SEQUENCE LISTING SUBMITTED ELECTRONICALLY

This application contains a sequence listing, which is submitted electronically via EFS-Web as an ASCII formatted sequence listing with a file name "JBI6065USNPSEQLIST.TXT" and a creation date of Mar. 28, 2019 and having a size of 126 kb. The sequence listing submitted via EFS-Web is part of the specification and is herein incorporated by reference in its entirety.

BACKGROUND OF THE INVENTION

It is estimated that autoimmune diseases afflict 1 in 20 persons (Hayter and Cook, Autoimmune Rev. 11(10):754-65 (2012)). The root cause of autoimmunity is emergence of dysregulated T cell clones reactive to self-antigens. Auto-reactive T cells initiate cytokine-driven feed-forward loops resulting in inflammation (e.g., leukocyte recruitment and edema), which when chronic, leads to tissue destruction and loss of function.

Antibodies that neutralize specific cytokines (e.g., anti-TNFα, IL-12, IL-23, IL-17) are useful to interrupt the feed-forward loops and minimize inflammation (Wolf and Ang, Immunol. Allergy Clin. North Am. 37(2):283-99 (2017); Her and Kavanaugh, J. Allergy Clin. Immunol. 137(1):19-27 (2016)). However, these agents require chronic treatment, as they do not address the initial root cause of the disease. Therefore, therapies that target the development and activation of auto-reactive T cells and not the cytokines are needed to address the root cause of disease versus targeting the downstream inflammation.

An improved selective approach that would address the root cause would be to develop antibodies that block the development and activation of auto-reactive T cells that recognize self-antigens. T cells recognize antigens by a heterodimeric surface receptor consisting of an β and a β chain and known as the T cell receptor (TCR). The α and β chain genes are subject to extensive somatic recombination in the thymus. Recombination during thymic T cell development gives rise to tremendous diversity in TCR genes expressed within an individual (Laydon et al., Philos. Trans. R. Soc. Long. B Biol. Sci. 370(1675):20140291 (2015)). Each TCR has distinct antigen recognition capability. The antigens are short peptides bound and displayed by one of six major histocompatibility complex (MHC) proteins of the host. Specifically, humans express three class I MHC genes (i.e., HLA-A, HLA-B, or HLA-C) and three class II MHC genes (i.e., HLA-DR, HLA-DP, or HLA-DQ) (Trowsdale, Immunol. Lett. 137(1-2):1-8 (2011)). MHC genes are among the most polymorphic genes in the genome and there are >1000 alleles of each MHC gene in the human population encoding hundreds of allomorphs (protein isoforms). Each MHC allomorph has a unique peptide binding surface and binds a unique repertoire of self and foreign peptides. TCRs expressed by mature T cells are "restricted" to one of the self MHC allomorphs, meaning that a T cell can only be activated by a specific peptide-MHC complex.

Much research effort has been made to determine the exact self-peptide-MHC complexes recognized by auto-reactive T cells. Although it is possible to detect T cells cognate for specific self-peptide-MHC complexes, it has been more difficult to identify self-peptide-MHC complexes recognized in a majority of patients or that are proven to drive disease. Further, autoimmune diseases may be driven by many T cell clones recognizing multiple self-peptide MHC complexes.

Although the identity of the self-peptide-MHC complexes remain obscure, genetics offer important clues as to the identity of the offending MHC, as many autoimmune diseases show a strong association with specific MHC alleles (Matzaraki et al., Genome Biology 18(1):76 (2017)). It is meaningful that specific alleles may be highly enriched in individuals with specific autoimmune diseases because each allomorph binds a unique repertoire of self-peptides. Thus, the genetic risk of an autoimmune disease is believed to reflect the ability of the allomorph to display tissue specific self-peptides. This is best exemplified by Goodpasture's disease where T cells recognize collagen IV peptide bound by HLA-DQ15 (Cairns et al., J. Am. Soc. Nephrol. 14(11): 2801-12 (2003)).

Inheritance of the HLA-C*06:02 allele is the strongest genetic determinant of who will develop the autoimmune disease called psoriasis (Nair et al., Am. J. Hum. Genet. 78(5):827-51 (2006); Elder et al., J. Invest. Dermatol. 130 (5):1213-26 (2010)). A large majority (~80%) of individuals experiencing the guttate form of psoriasis carry the HLA-C*06:02 allele (Asumalahti et al., J. Invest. Dermatol. 120(4):627-32 (2003)), while about 50% of individuals with the more common plaque psoriasis carry this allele compared with about 10-15% of healthy control individuals. One copy of the HLA-C*06:02 allele carries a ~10% lifetime risk, which is 2.5× higher in homozygotes (Gudjonsson et al., Br. J. Dermatol. 148(2):233-5 (2003)), and individuals that are HLA-C*06:02 positive develop psoriasis at an earlier age and with greater severity (Gudjonsson et al., J. Invest. Dermatol. 126(4):740-5 (2006)). Importantly the risk of psoriasis in HLA-C*06:02 individuals is epistatic with a catalytically more active variant of ERAP1 (Strange et al., N. Genet. 42(11):985-90 (2010)), the primary endopeptidase required to customize peptides for class I MHC loading.

While the literature does not provide a consensus on self-peptides driving psoriasis, several self-peptides/proteins have been shown to activate T cells isolated from patient blood or skin. To date, these include the skin associated proteins keratin-17, LL37, ADAMTSL5, Maspin, and per-oxiredoxin-2 or peptide derivatives (Yunusbaeva et al., Scientific Reports vol. 8, article number 6098 (2018); Lande et al., Nat. Commun. 5:5621 (2014); Arakawa et al, J. Exp. Med. 212(13):2203-12 (2015); and Besgen et al., J. Immunol. 184(9):5392-402 (2010)). Peptides derived from keratin-17, LL37, and ADAMTSL5 have been shown to be part of the repertoire of peptides that HLA-Cw6 may bind, and LL37 peptide-bound HLA-Cw6 tetramers have been used to identify cognate T cells in psoriasis patients. Meanwhile keratin-17 and peroxiredoxin-2-peptides activate T cells to a significantly greater frequency in HLA-C*06:02 positive psoriasis patients versus those that are negative. Evidence of clonal T cell expansion has been reported in psoriasis lesions, and the α and β TCR genes expressed by a few clones have been sequenced and reported (Kim et al., PLoS One 7(5):e37338 (2012)). The cognate peptide-MHC of one of these TCRs was deconvoluted and determined (Arakawa et al, J. Exp. Med. 212(13):2203-12 (2015)). The TCR was HLA-Cw6 restricted and ADAMTSL5(57-65) presented by HLA-Cw6 on melanocytes appeared to be the cognate antigen. Collectively, the data point to a critical role of HLA-Cw6 in presenting autoantigens to autoreactive T cells in psoriasis.

Antibodies to HLA-C that block the development and activation of auto-reactive T cells could be efficacious in addressing the root problem of psoriasis.

BRIEF SUMMARY OF THE INVENTION

In one general aspect, the invention relates to isolated monoclonal antibodies or antigen-binding fragments thereof that bind HLA-C, optionally, HLA-Cw6.

Provided are isolated monoclonal antibody or antigen-binding fragment thereof comprising a heavy chain variable region and a light chain variable region, the heavy chain variable region comprising a heavy chain complementarity determining region 1 (HCDR1), HCDR2, and a HCDR3, the light chain variable region comprising a light chain complementarity determining region 1 (LCDR1), LCDR2, and LCDR3, wherein the HCDR1, HCDR2, HCDR3, LCDR1, LCDR2 and LCDR3 comprise the amino acid sequences of:
  a. SEQ ID NOs: 37, 38, 39, 64, 65, and 66, respectively;
  b. SEQ ID NOs: 40, 41, 42, 67, 68, and 69, respectively;
  c. SEQ ID NOs: 43, 44, 45, 70, 71, and 72, respectively;
  d. SEQ ID NOs: 46, 47, 48, 73, 74, and 75, respectively;
  e. SEQ ID NOs: 49, 50, 51, 76, 77, and 78, respectively;
  f. SEQ ID NOs: 52, 53, 54, 79, 80, and 81, respectively;
  g. SEQ ID NOs: 55, 56, 57, 82, 83, and 84, respectively;
  h. SEQ ID NOs: 58, 59, 60, 85, 86, and 87, respectively; or
  i. SEQ ID NOs: 61, 62, 63, 88, 89, and 90, respectively;
wherein the antibody or antigen-binding fragment thereof specifically binds HLA-C, preferably HLA-Cw6.

Also provided are isolated monoclonal antibody or antigen-binding fragment thereof comprising a heavy chain variable region and a light chain variable region, the heavy chain variable region comprising a heavy chain complementarity determining region 1 (HCDR1), HCDR2, and a HCDR3, the light chain variable region comprising a light chain complementarity determining region 1 (LCDR1), LCDR2, and LCDR3, wherein the HCDR1, HCDR2, HCDR3, LCDR1, LCDR2 and LCDR3 comprise the amino acid sequences of:
  a. SEQ ID NOs: 91, 92, 93, 118, 119, and 120, respectively;
  b. SEQ ID NOs: 94, 95, 96, 121, 122, and 123, respectively;
  c. SEQ ID NOs: 97, 98, 99, 124, 125, and 126, respectively;
  d. SEQ ID NOs: 100, 101, 102, 127, 128, and 129, respectively;
  e. SEQ ID NOs: 103, 104, 105, 130, 131, and 132, respectively;
  f. SEQ ID NOs: 106, 107, 108, 133, 134, and 135, respectively;
  g. SEQ ID NOs: 109, 110, 111, 136, 137, and 138, respectively;
  h. SEQ ID NOs: 112, 113, 114, 139, 140, and 141, respectively; or
  i. SEQ ID NOs: 115, 116, 117, 142, 143, and 144, respectively;
wherein the antibody or antigen-binding fragment thereof specifically binds HLA-C, preferably HLA-Cw6.

Also provided are isolated monoclonal antibody or antigen-binding fragment thereof comprising a heavy chain variable region and a light chain variable region, the heavy chain variable region comprising a heavy chain complementarity determining region 1 (HCDR1), HCDR2, and a HCDR3, the light chain variable region comprising a light chain complementarity determining region 1 (LCDR1), LCDR2, and LCDR3, wherein the HCDR1, HCDR2, HCDR3, LCDR1, LCDR2 and LCDR3 comprise the amino acid sequences of:
  a. SEQ ID NOs: 145, 146, 147, 172, 173, and 174, respectively;
  b. SEQ ID NOs: 148, 149, 150, 175, 176, and 177, respectively;
  c. SEQ ID NOs: 151, 152, 153, 178, 179, and 180, respectively;
  d. SEQ ID NOs: 154, 155, 156, 181, 182, and 183, respectively;
  e. SEQ ID NOs: 157, 158, 159, 184, 185, and 186, respectively;
  f. SEQ ID NOs: 160, 161, 162, 187, 188, and 189, respectively;
  g. SEQ ID NOs: 163, 164, 165, 190, 191, and 192, respectively;
  h. SEQ ID NOs: 166, 167, 168, 193, 194, and 195, respectively; or
  i. SEQ ID NOs: 169, 170, 171, 196, 197, and 198, respectively;
wherein the antibody or antigen-binding fragment thereof specifically binds HLA-C, preferably HLA-Cw6.

In certain embodiments, the isolated monoclonal antibody or antigen-binding fragment thereof comprises a heavy chain variable region having a polypeptide sequence at least 95%, at least 96%, at least 97%, at least 98%, or at least 99% identical to SEQ ID NO:1, 3, 5, 7, 9, 11, 13, 15, or 17, or a light chain variable region having a polypeptide sequence at least 95%, at least 96%, at least 97%, at least 98%, or at least 99% identical SEQ ID NO:2, 4, 6, 8, 10, 12, 14, 16, or 18.

In certain embodiments, the isolated monoclonal antibody or antigen-binding fragment thereof comprises:
  a. a heavy chain variable region having the polypeptide sequence of SEQ ID NO:1, and a light chain variable region having the polypeptide sequence of SEQ ID NO:2;
  b. a heavy chain variable region having the polypeptide sequence of SEQ ID NO:3, and a light chain variable region having the polypeptide sequence of SEQ ID NO:4;
  c. a heavy chain variable region having the polypeptide sequence of SEQ ID NO:5, and a light chain variable region having the polypeptide sequence of SEQ ID NO:6;
  d. a heavy chain variable region having the polypeptide sequence of SEQ ID NO:7, and a light chain variable region having the polypeptide sequence of SEQ ID NO:8;

e. a heavy chain variable region having the polypeptide sequence of SEQ ID NO:9, and a light chain variable region having the polypeptide sequence of SEQ ID NO:10;
f. a heavy chain variable region having the polypeptide sequence of SEQ ID NO:11, and a light chain variable region having the polypeptide sequence of SEQ ID NO:12;
g. a heavy chain variable region having the polypeptide sequence of SEQ ID NO:13, and a light chain variable region having the polypeptide sequence of SEQ ID NO:14;
h. a heavy chain variable region having the polypeptide sequence of SEQ ID NO:15, and a light chain variable region having the polypeptide sequence of SEQ ID NO:16; or
i. a heavy chain variable region having the polypeptide sequence of SEQ ID NO:17, and a light chain variable region having the polypeptide sequence of SEQ ID NO:18.

In certain embodiments, the isolated monoclonal antibody or antigen-binding fragment thereof is chimeric.

In certain embodiments, the isolated monoclonal antibody or antigen-binding fragment thereof is human or humanized.

In certain embodiments, the isolated monoclonal antibody or antigen-binding blocks development and activation of T cells, through binding and inhibition of antigen presentation by HLA-Cw6.

Also provided are isolated nucleic acids encoding the monoclonal antibodies or antigen-binding fragments thereof of the invention.

Also provided are vectors comprising the isolated nucleic acids encoding the monoclonal antibodies or antigen-binding fragments thereof of the invention.

Also provided are host cells comprising the vectors comprising the isolated nucleic acids encoding the monoclonal antibodies or antigen-binding fragments thereof of the invention.

In certain embodiments, provided is a pharmaceutical composition comprising the isolated monoclonal antibody or antigen-binding fragment thereof of the invention and a pharmaceutically acceptable carrier.

Also provided are methods of treating or preventing an autoimmune disease in a subject in need thereof. The methods comprise administering to the subject the pharmaceutical compositions of the invention. The autoimmune disease can be selected from, but not limited to, psoriasis, plaque psoriasis, guttate psoriasis, and psoriatic arthritis.

Also provided are methods of inhibiting activation of auto-reactive T cells in a subject in need thereof. The methods comprise administering to the subject the pharmaceutical compositions of the invention, wherein administration of the pharmaceutical composition inhibits activation of the auto-reactive T cells in the subject.

Also provided are methods of inhibiting the functional binding of a T cell receptor (TCR) to a peptide-bound HLA-C (e.g., HLA-Cw6) in a HLA-C (e.g., HLA-Cw6) expressing cell. The methods comprise contacting the cell with an isolated monoclonal antibody or antigen-binding fragment thereof of the invention, wherein the monoclonal antibody or antigen-binding fragment thereof of the invention binds the peptide-bound HLA-C and inhibits the functional binding of the TCR. In certain embodiments, the cell is contacted in vitro. In certain embodiments, the cell is contacted in vivo.

Also provided are methods of producing the monoclonal antibody or antigen-binding fragment thereof of the invention. The methods comprise culturing a cell comprising a nucleic acid encoding the monoclonal antibody or antigen-binding fragment thereof under conditions to produce the monoclonal antibody or antigen-binding fragment thereof and recovering the antibody or antigen-binding fragment thereof from the cell or culture.

Also provided are methods of producing a pharmaceutical composition comprising the monoclonal antibody or antigen-binding fragment thereof of the invention. The methods comprise combining the monoclonal antibody or antigen-binding fragment thereof with a pharmaceutically acceptable carrier to obtain the pharmaceutical composition.

BRIEF DESCRIPTION OF THE DRAWINGS

The foregoing summary, as well as the following detailed description of preferred embodiments of the present application, will be better understood when read in conjunction with the appended drawings. It should be understood, however, that the application is not limited to the precise embodiments shown in the drawings.

DETAILED DESCRIPTION OF THE INVENTION

Figure 1:
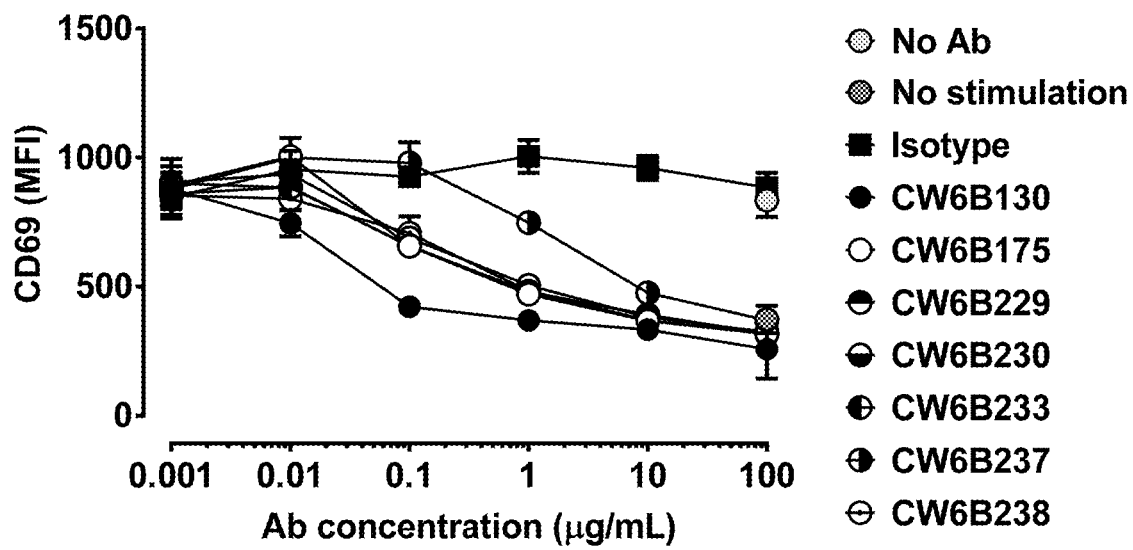
FIG. 1 shows a graph demonstrating the inhibition of HLA-Cw6/ADAMTSL5-Abu dependent CD69 up-regulation on a T cell line by anti-HLA-C antibodies.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize or be able to ascertain using no more than routine experimentation, many equivalents to the specific embodiments of the invention described herein. Such equivalents are intended to be encompassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, the term "consists of," or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition. See M.P.E.P. § 2111.03.

As used herein, "subject" means any animal, preferably a mammal, most preferably a human. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

It should also be understood that the terms "about," "approximately," "generally," "substantially," and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

The terms "identical" or percent "identity," in the context of two or more nucleic acids or polypeptide sequences (e.g., anti-HLA-C antibodies and polynucleotides that encode them, HLA-C polypeptides and HLA-C polynucleotides that encode them), refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1997) Nucleic Acids Res. 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased.

Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions.

As used herein, the terms "inhibit," "inhibiting," and "inhibition," mean to decrease an activity, response, condition, disease or other biological parameter. This can include, but is not limited to, complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between, as compared to native or control levels. By way of a non-limiting example, an antibody of the invention can inhibit the activation of an auto-reactive T cell by binding HLA-C (e.g., HLA-Cw6).

Antibodies

The invention generally relates to isolated anti-HLA-C antibodies (e.g., HLA-Cw6 antibodies), nucleic acids and expression vectors encoding the antibodies, recombinant cells containing the vectors, and compositions comprising the antibodies. Methods of making the antibodies, and methods of using the antibodies to treat diseases including autoimmune diseases (e.g., psoriasis) are also provided. The antibodies of the invention possess one or more desirable functional properties, including but not limited to high-affinity binding to HLA-C, high specificity to HLA-C, the ability to inhibit activation of auto-reactive T cells, the ability to inhibit the functional binding of a TCR to a peptide-bound HLA-Cw6, and the ability to treat or prevent an autoimmune disorder in a subject in need thereof.

In a general aspect, the invention relates to isolated monoclonal antibodies or antigen-binding fragments thereof that specifically bind HLA-C (e.g., HLA-Cw6).

As used herein, the term "antibody" is used in a broad sense and includes immunoglobulin or antibody molecules including human, humanized, composite and chimeric antibodies and antibody fragments that are monoclonal or polyclonal. In general, antibodies are proteins or peptide chains that exhibit binding specificity to a specific antigen. Antibody structures are well known. Immunoglobulins can be assigned to five major classes (i.e., IgA, IgD, IgE, IgG and IgM), depending on the heavy chain constant domain amino acid sequence. IgA and IgG are further sub-classified as the isotypes IgA1, IgA2, IgG1, IgG2, IgG3 and IgG4. Accordingly, the antibodies of the invention can be of any of the five major classes or corresponding sub-classes. Preferably, the antibodies of the invention are IgG1, IgG2, IgG3 or IgG4. Antibody light chains of vertebrate species can be assigned to one of two clearly distinct types, namely kappa and lambda, based on the amino acid sequences of their constant domains. Accordingly, the antibodies of the invention can contain a kappa or lambda light chain constant domain. According to particular embodiments, the antibodies of the invention include heavy and/or light chain constant regions from rat or human antibodies. In addition to the heavy and light constant domains, antibodies contain an antigen-binding region that is made up of a light chain variable region and a heavy chain variable region, each of which contains three domains (i.e., complementarity determining regions 1-3; CDR1, CDR2, and CDR3). The light chain variable region domains are alternatively referred to as LCDR1, LCDR2, and LCDR3, and the heavy chain variable region domains are alternatively referred to as HCDR1, HCDR2, and HCDR3.

As used herein, the term an "isolated antibody" refers to an antibody which is substantially free of other antibodies having different antigenic specificities (e.g., an isolated antibody that specifically binds to HLA-Cw6 is substantially free of antibodies that do not bind to HLA-Cw6). In addition, an isolated antibody is substantially free of other cellular material and/or chemicals.

As used herein, the term "monoclonal antibody" refers to an antibody obtained from a population of substantially homogeneous antibodies, i.e., the individual antibodies comprising the population are identical except for possible naturally occurring mutations that may be present in minor amounts. The monoclonal antibodies of the invention can be made by the hybridoma method, phage display technology, single lymphocyte gene cloning technology, or by recombinant DNA methods. For example, the monoclonal antibodies can be produced by a hybridoma which includes a B cell obtained from a transgenic nonhuman animal, such as a transgenic mouse or rat, having a genome comprising a human heavy chain transgene and a light chain transgene.

As used herein, the term "antigen-binding fragment" refers to an antibody fragment such as, for example, a diabody, a Fab, a Fab', a F(ab')2, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), a single domain antibody (sdab) an scFv dimer (bivalent diabody), a multispecific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment binds. According to particular embodiments, the antigen-binding fragment comprises a light chain variable region, a light chain constant region, and an Fd segment of the heavy chain. According to other particular embodiments, the antigen-binding fragment comprises Fab and F(ab').

As used herein, the term "single-chain antibody" refers to a conventional single-chain antibody in the field, which comprises a heavy chain variable region and a light chain variable region connected by a short peptide of about 15 to about 20 amino acids. As used herein, the term "single domain antibody" refers to a conventional single domain antibody in the field, which comprises a heavy chain variable region and a heavy chain constant region or which comprises only a heavy chain variable region.

As used herein, the term "human antibody" refers to an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide.

As used herein, the term "humanized antibody" refers to a non-human antibody that is modified to increase the sequence homology to that of a human antibody, such that the antigen-binding properties of the antibody are retained, but its antigenicity in the human body is reduced.

As used herein, the term "chimeric antibody" refers to an antibody wherein the amino acid sequence of the immunoglobulin molecule is derived from two or more species. The variable region of both the light and heavy chains often corresponds to the variable region of an antibody derived from one species of mammal (e.g., mouse, rat, rabbit, etc.) having the desired specificity, affinity, and capability, while the constant regions correspond to the sequences of an antibody derived from another species of mammal (e.g., human) to avoid eliciting an immune response in that species.

As used herein, the term "multispecific antibody" refers to an antibody that comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, the first and second epitopes are on the same antigen, e.g., the same protein (or subunit of a multimeric protein). In an embodiment, the first and second epitopes overlap or substantially overlap. In an embodiment, the first and second epitopes do not overlap or do not substantially overlap. In an embodiment, the first and second epitopes are on different antigens, e.g., the different proteins (or different subunits of a multimeric protein). In an embodiment, a multispecific antibody comprises a third, fourth, or fifth immunoglobulin variable domain. In an embodiment, a multispecific antibody is a bispecific antibody molecule, a trispecific antibody molecule, or a tetraspecific antibody molecule.

As used herein, the term "bispecifc antibody" refers to a multispecific antibody that binds no more than two epitopes or two antigens. A bispecific antibody is characterized by a first immunoglobulin variable domain sequence which has binding specificity for a first epitope and a second immunoglobulin variable domain sequence that has binding specificity for a second epitope. In an embodiment, the first and second epitopes are on the same antigen, e.g., the same protein (or subunit of a multimeric protein). In an embodiment, the first and second epitopes overlap or substantially overlap. In an embodiment, the first and second epitopes are on different antigens, e.g., the different proteins (or different subunits of a multimeric protein). In an embodiment, a bispecific antibody comprises a heavy chain variable domain sequence and a light chain variable domain sequence which have binding specificity for a first epitope and a heavy chain variable domain sequence and a light chain variable domain sequence which have binding specificity for a second epitope. In an embodiment, a bispecific antibody comprises a half antibody, or fragment thereof, having binding specificity for a first epitope and a half antibody, or fragment thereof, having binding specificity for a second epitope. In an embodiment, a bispecific antibody comprises a scFv, or fragment thereof, having binding specificity for a first epitope, and a scFv, or fragment thereof, having binding specificity for a second epitope. In an embodiment, the first epitope is located on HLA-Cw6 and the second epitope is located on other autoimmune associated surface antigens.

As used herein, the term "HLA-Cw6" refers to a MHC class I heavy chain receptor. HLA-Cw6 is one of the serotypes of the HLA-C class I heavy chain receptors. The HLA-C receptor is a heterodimer consisting of a HLA-C mature gene product and the b2-microglobulin. The mature C chain is anchored in the cell membrane. HLA-C are expressed in nearly all cells and serve to present small peptides to the immune system, which acts to determine if the small peptide is a self or non-self peptide. HLA-C is a locus on chromosome 6, which encodes for a large number of HLA-C alleles that are Class-I-MHC receptors. Serotypes of HLA-C proteins include, but are not limited to, HLA-Cw1, HLA-Cw2, HLA-Cw3, HLA-Cw4, HLA-Cw5, HLA-Cw6, HLA-Cw6, HLA-Cw7, HLA-Cw8, HLA-Cw12, HLA-Cw14, HLA-Cw15, HLA-Cw-16, HLA-Cw17, and HLA-Cw18. An exemplary amino acid sequence of a human HLA-Cw6 is represented by GenBank Accession No. Q29963.

As used herein, an antibody that "specifically binds to HLA-Cw6" refers to an antibody that binds to a HLA-Cw6, preferably a human HLA-Cw6, with a KD of $1 \times 10^{-7}$ M or less, preferably $1 \times 10^{-8}$ M or less, more preferably $5 \times 10^{-9}$ M or less, $1 \times 10^{-9}$ M or less, $5 \times 10^{-10}$ M or less, or $1 \times 10^{-10}$ M or less. The term "KD" refers to the dissociation constant, which is obtained from the ratio of Kd to Ka (i.e., Kd/Ka) and is expressed as a molar concentration (M). KD values for antibodies can be determined using methods in the art in view of the present disclosure. For example, the KD of an antibody can be determined by using surface plasmon resonance, such as by using a biosensor system, e.g., a Biacore® system, or by using bio-layer interferometry technology, such as an Octet RED96 system.

The smaller the value of the KD of an antibody, the higher affinity that the antibody binds to a target antigen.

According to a particular aspect, the invention relates to an isolated monoclonal antibody or antigen-binding fragment thereof comprising a heavy chain complementarity determining region 1 (HCDR1), a HCDR2, a HCDR3, a light chain complementarity determining region 1 (LCDR1), a LCDR2, and a LCDR3, having the polypeptide sequences of:
  a. SEQ ID NOs: 37, 38, 39, 64, 65, and 66, respectively;
  b. SEQ ID NOs: 40, 41, 42, 67, 68, and 69, respectively;
  c. SEQ ID NOs: 43, 44, 45, 70, 71, and 72, respectively;
  d. SEQ ID NOs: 46, 47, 48, 73, 74, and 75, respectively;
  e. SEQ ID NOs: 49, 50, 51, 76, 77, and 78, respectively;
  f. SEQ ID NOs: 52, 53, 54, 79, 80, and 81, respectively;
  g. SEQ ID NOs: 55, 56, 57, 82, 83, and 84, respectively;
  h. SEQ ID NOs: 58, 59, 60, 85, 86, and 87, respectively; or
  i. SEQ ID NOs: 61, 62, 63, 88, 89, and 90, respectively;
wherein the antibody or antigen-binding fragment thereof specifically binds HLA-C, preferably HLA-Cw6.

According to another particular aspect, the invention relates to an isolated monoclonal antibody or antigen-binding fragment thereof comprising a heavy chain complementarity determining region 1 (HCDR1), HCDR2, HCDR3, a light chain complementarity determining region 1 (LCDR1), LCDR2, and LCDR3, having the polypeptide sequence of:
  a. SEQ ID NOs: 91, 92, 93, 118, 119, and 120, respectively;
  b. SEQ ID NOs: 94, 95, 96, 121, 122, and 123, respectively;
  c. SEQ ID NOs: 97, 98, 99, 124, 125, and 126, respectively;
  d. SEQ ID NOs: 100, 101, 102, 127, 128, and 129, respectively;
  e. SEQ ID NOs: 103, 104, 105, 130, 131, and 132, respectively;
  f. SEQ ID NOs: 106, 107, 108, 133, 134, and 135, respectively;
  g. SEQ ID NOs: 109, 110, 111, 136, 137, and 138, respectively;
  h. SEQ ID NOs: 112, 113, 114, 139, 140, and 141, respectively; or
  i. SEQ ID NOs: 115, 116, 117, 142, 143, and 144, respectively;
wherein the antibody or antigen-binding fragment thereof specifically binds HLA-C, preferably HLA-Cw6.

According to another particular aspect, the invention relates to an isolated monoclonal antibody or antigen-binding fragment thereof comprising a heavy chain complementarity determining region 1 (HCDR1), HCDR2, HCDR3, a light chain complementarity determining region 1 (LCDR1), LCDR2, and LCDR3, having the polypeptide sequence of:
  a. SEQ ID NOs: 145, 146, 147, 172, 173, and 174, respectively;
  b. SEQ ID NOs: 148, 149, 150, 175, 176, and 177, respectively;
  c. SEQ ID NOs: 151, 152, 153, 178, 179, and 180, respectively;
  d. SEQ ID NOs: 154, 155, 156, 181, 182, and 183, respectively;
  e. SEQ ID NOs: 157, 158, 159, 184, 185, and 186, respectively;
  f. SEQ ID NOs: 160, 161, 162, 187, 188, and 189, respectively;
  g. SEQ ID NOs: 163, 164, 165, 190, 191, and 192, respectively;
  h. SEQ ID NOs: 166, 167, 168, 193, 194, and 195, respectively; or
  i. SEQ ID NOs: 169, 170, 171, 196, 197, and 198, respectively;
wherein the antibody or antigen-binding fragment thereof specifically binds HLA-C, preferably HLA-Cw6.

According to another particular aspect, the invention relates to an isolated monoclonal antibody or antigen-binding fragment thereof comprising a heavy chain variable region having a polypeptide sequence at least 85%, preferably 90%, more preferably 95% or more, such as 95%, 96%, 97%, 98%, or 99% identical to SEQ ID NO:1, 3, 5, 7, 9, 11, 13, 15, or 17, or a light chain variable region having a polypeptide sequence at least 85%, preferably 90%, more preferably 95% or more, such as 95%, 96%, 97%, 98%, or 99% identical to SEQ ID NO:2, 4, 6, 8, 10, 12, 14, 16, or 18.

According to one preferred embodiment, the isolated monoclonal antibody or antigen-binding fragment thereof of the invention comprises a heavy chain variable region having the polypeptide sequence at least 85%, preferably 90%, more preferably 95% or more, such as 95%, 96%, 97%, 98%, or 99/a identical to SEQ ID NO:1, 3, 5, 7, 9, 11, 13, 15, or 17, and a light chain variable region having a polypeptide sequence at least 85%, preferably 90%, more preferably 95% or more, such as 95%, 96%, 97%, 98%, or 99% identical to SEQ ID NO:2, 4, 6, 8, 10, 12, 14, 16, or 18, respectively.

According to another particular aspect, the invention relates to an isolated monoclonal antibody or antigen-binding fragment thereof of the invention, comprising:
  a. a heavy chain variable region having the polypeptide sequence of SEQ ID NO:1, and a light chain variable region having the polypeptide sequence of SEQ ID NO:2;
  b. a heavy chain variable region having the polypeptide sequence of SEQ ID NO:3, and a light chain variable region having the polypeptide sequence of SEQ ID NO:4;
  c. a heavy chain variable region having the polypeptide sequence of SEQ ID NO:5, and a light chain variable region having the polypeptide sequence of SEQ ID NO:6;
  d. a heavy chain variable region having the polypeptide sequence of SEQ ID NO:7, and a light chain variable region having the polypeptide sequence of SEQ ID NO:8;
  e. a heavy chain variable region having the polypeptide sequence of SEQ ID NO:9, and a light chain variable region having the polypeptide sequence of SEQ ID NO:10;
  f. a heavy chain variable region having the polypeptide sequence of SEQ ID NO:11, and a light chain variable region having the polypeptide sequence of SEQ ID NO:12;
  g. a heavy chain variable region having the polypeptide sequence of SEQ ID NO:13, and a light chain variable region having the polypeptide sequence of SEQ ID NO:14;
  h. a heavy chain variable region having the polypeptide sequence of SEQ ID NO:15, and a light chain variable region having the polypeptide sequence of SEQ ID NO:16; or i. a heavy chain variable region having the polypeptide sequence of SEQ ID NO:17, and a light chain variable region having the polypeptide sequence of SEQ ID NO:18.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:37, 38, 39, 64, 65, and 66, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:1, and a light chain variable region having a polypeptide sequence at least 85%, preferably 90%, more preferably 95% or more, such as 95%, 96%, 97%, 98%, or 99% identical to SEQ ID NO:2. Preferably, the isolated monoclonal antibody or antigen-binding fragment thereof comprises a heavy chain variable region having the polypeptide sequence of SEQ ID NO:1; and a light chain variable region having the polypeptide sequence of SEQ ID NO:2.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:40, 41, 42, 67, 68, and 69, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:3, and a light chain variable region having a polypeptide sequence at least 85%, preferably 90%, more preferably 95% or more, such as 95%, 96%, 97%, 98%, or 99% identical to SEQ ID NO:4. Preferably, the isolated monoclonal antibody or antigen-binding fragment thereof comprises a heavy chain variable region having the polypeptide sequence of SEQ ID NO:3; and a light chain variable region having the polypeptide sequence of SEQ ID NO:4.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:43, 44, 45, 70, 71, and 72, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:5, and a light chain variable region having a polypeptide sequence at least 85%, preferably 90%, more preferably 95% or more, such as 95%, 96%, 97%, 98%, or 99% identical to SEQ ID NO:6. Preferably, the isolated monoclonal antibody or antigen-binding fragment thereof comprises a heavy chain variable region having the polypeptide sequence of SEQ ID NO:5; and a light chain variable region having the polypeptide sequence of SEQ ID NO:6.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:46, 47, 48, 73, 74, and 75, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:7, and a light chain variable region having a polypeptide sequence at least 85%, preferably 90%, more preferably 95% or more, such as 95%, 96%, 97%, 98%, or 99% identical to SEQ ID NO:8. Preferably, the isolated monoclonal antibody or antigen-binding fragment thereof comprises a heavy chain variable region having the polypeptide sequence of SEQ ID NO:7; and a light chain variable region having the polypeptide sequence of SEQ ID NO:8.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:49, 50, 51, 76, 77, and 78, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:9, and a light chain variable region having a polypeptide sequence at least 85%, preferably 90%, more preferably 95% or more, such as 95%, 96%, 97%, 98%, or 99% identical to SEQ ID NO:10. Preferably, the isolated monoclonal antibody or antigen-binding fragment thereof comprises a heavy chain variable region having the polypeptide sequence of SEQ ID NO:9; and a light chain variable region having the polypeptide sequence of SEQ ID NO:10.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:52, 53, 54, 79, 80, and 81, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:11, and a light chain variable region having a polypeptide sequence at least 85%, preferably 90%, more preferably 95% or more, such as 95%, 96%, 97%, 98%, or 99% identical to SEQ ID NO:12. Preferably, the isolated monoclonal antibody or antigen-binding fragment thereof comprises a heavy chain variable region having the polypeptide sequence of SEQ ID NO:11; and a light chain variable region having the polypeptide sequence of SEQ ID NO:12.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:55, 56, 57, 82, 83, and 84, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:13, and a light chain variable region having a polypeptide sequence at least 85%, preferably 90%, more preferably 95% or more, such as 95%, 96%, 97%, 98%, or 99% identical to SEQ ID NO:14. Preferably, the isolated monoclonal antibody or antigen-binding fragment thereof comprises a heavy chain variable region having the polypeptide sequence of SEQ ID NO:13; and a light chain variable region having the polypeptide sequence of SEQ ID NO:14.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:58, 59, 60, 85, 86, and 87, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:15, and a light chain variable region having a polypeptide sequence at least 85%, preferably 90%, more preferably 95% or more, such as 95%, 96%, 97%, 98%, or 99% identical to SEQ ID NO:16. Preferably, the isolated monoclonal antibody or antigen-binding fragment thereof comprises a heavy chain variable region having the polypeptide sequence of SEQ ID NO:15; and a light chain variable region having the polypeptide sequence of SEQ ID NO:16.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:61, 62, 63, 88, 89, and 90, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:17, and a light chain variable region having a polypeptide sequence at least 85%, preferably 90%, more preferably 95% or more, such as 95%, 96%, 97%, 98%, or 99% identical to SEQ ID NO:18. Preferably, the isolated monoclonal antibody or antigen-binding fragment thereof comprises a heavy chain variable region having the polypeptide sequence of SEQ ID NO:17; and a light chain variable region having the polypeptide sequence of SEQ ID NO:18.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:91, 92, 93, 118, 119, and 120, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:1, and a light chain variable region having a polypeptide sequence at least 85%, preferably 90%, more preferably 95% or more, such as 95%, 96%, 97%, 98%, or 99% identical to SEQ ID NO:2. Preferably, the isolated monoclonal antibody or antigen-binding fragment thereof comprises a heavy chain variable region having the polypeptide sequence of SEQ ID NO:1; and a light chain variable region having the polypeptide sequence of SEQ ID NO:2.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:94, 95, 96, 121, 122, and 123, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:3, and a light chain variable region having a polypeptide sequence at least 85%, preferably 90%, more preferably 95% or more, such as 95%, 96%, 97%, 98%, or 99% identical to SEQ ID NO:4. Preferably, the isolated monoclonal antibody or antigen-binding fragment thereof comprises a heavy chain variable region having the polypeptide sequence of SEQ ID NO:3; and a light chain variable region having the polypeptide sequence of SEQ ID NO:4.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:97, 98, 99, 124, 125, and 126, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:5, and a light chain variable region having a polypeptide sequence at least 85%, preferably 90%, more preferably 95% or more, such as 95%, 96%, 97%, 98%, or 99% identical to SEQ ID NO:6. Preferably, the isolated monoclonal antibody or antigen-binding fragment thereof comprises a heavy chain variable region having the polypeptide sequence of SEQ ID NO:5; and a light chain variable region having the polypeptide sequence of SEQ ID NO:6.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:100, 101, 102, 127, 128, and 129, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:7, and a light chain variable region having a polypeptide sequence at least 85%, preferably 90%, more preferably 95% or more, such as 95%, 96%, 97%, 98%, or 99% identical to SEQ ID NO:8. Preferably, the isolated monoclonal antibody or antigen-binding fragment thereof comprises a heavy chain variable region having the polypeptide sequence of SEQ ID NO:7; and a light chain variable region having the polypeptide sequence of SEQ ID NO:8.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:103, 104, 105, 130, 131, and 132, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:9, and a light chain variable region having a polypeptide sequence at least 85%, preferably 90%, more preferably 95% or more, such as 95%, 96%, 97%, 98%, or 99% identical to SEQ ID NO:10. Preferably, the isolated monoclonal antibody or antigen-binding fragment thereof comprises a heavy chain variable region having the polypeptide sequence of SEQ ID NO:9; and a light chain variable region having the polypeptide sequence of SEQ ID NO:10.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:106, 107, 108, 133, 134, and 135, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:11, and a light chain variable region having a polypeptide sequence at least 85%, preferably 90%, more preferably 95% or more, such as 95%, 96%, 97%, 98%, or 99% identical to SEQ ID NO:12. Preferably, the isolated monoclonal antibody or antigen-binding fragment thereof comprises a heavy chain variable region having the polypeptide sequence of SEQ ID NO:11; and a light chain variable region having the polypeptide sequence of SEQ ID NO:12.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:109, 110, 111, 136, 137, and 138, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:13, and a light chain variable region having a polypeptide sequence at least 85%, preferably 90%, more preferably 95% or more, such as 95%, 96%, 97%, 98%, or 99% identical to SEQ ID NO:14. Preferably, the isolated monoclonal antibody or antigen-binding fragment thereof comprises a heavy chain variable region having the polypeptide sequence of SEQ ID NO:13; and a light chain variable region having the polypeptide sequence of SEQ ID NO:14.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:112, 113, 114, 139, 140, and 141, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:15, and a light chain variable region having a polypeptide sequence at least 85%, preferably 90%, more preferably 95% or more, such as 95%, 96%, 97%, 98%, or 99% identical to SEQ ID NO:16. Preferably, the isolated monoclonal antibody or antigen-binding fragment thereof comprises a heavy chain variable region having the polypeptide sequence of SEQ ID NO:15; and a light chain variable region having the polypeptide sequence of SEQ ID NO:16.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:115, 116, 117, 142, 143, and 144, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:17, and a light chain variable region having a polypeptide sequence at least 85%, preferably 90%, more preferably 95% or more, such as 95%, 96%, 97%, 98%, or 99% identical to SEQ ID NO:18. Preferably, the isolated monoclonal antibody or antigen-binding fragment thereof comprises a heavy chain variable region having the polypeptide sequence of SEQ ID NO:17; and a light chain variable region having the polypeptide sequence of SEQ ID NO:18.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:145, 146, 147, 172, 173, and 174, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:1, and a light chain variable region having a polypeptide sequence at least 85%, preferably 90%, more preferably 95% or more, such as 95%, 96%, 97%, 98%, or 99% identical to SEQ ID NO:2. Preferably, the isolated monoclonal antibody or antigen-binding fragment thereof comprises a heavy chain variable region having the polypeptide sequence of SEQ ID NO:1; and a light chain variable region having the polypeptide sequence of SEQ ID NO:2.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:148, 149, 150, 175, 176, and 177, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:3, and a light chain variable region having a polypeptide sequence at least 85%, preferably 90%, more preferably 95% or more, such as 95%, 96%, 97%, 98%, or 99% identical to SEQ ID NO:4. Preferably, the isolated monoclonal antibody or antigen-binding fragment thereof comprises a heavy chain variable region having the polypeptide sequence of SEQ ID NO:3; and a light chain variable region having the polypeptide sequence of SEQ ID NO:4.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:151, 152, 153, 178, 179, and 180, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:5, and a light chain variable region having a polypeptide sequence at least 85%, preferably 90%, more preferably 95% or more, such as 95%, 96%, 97%, 98%, or 99% identical to SEQ ID NO:6. Preferably, the isolated monoclonal antibody or antigen-binding fragment thereof comprises a heavy chain variable region having the polypeptide sequence of SEQ ID NO:5; and a light chain variable region having the polypeptide sequence of SEQ ID NO:6.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:154, 155, 156, 181, 182, and 183, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:7, and a light chain variable region having a polypeptide sequence at least 85%, preferably 90%, more preferably 95% or more, such as 95%, 96%, 97%, 98%, or 99% identical to SEQ ID NO:8. Preferably, the isolated monoclonal antibody or antigen-binding fragment thereof comprises a heavy chain variable region having the polypeptide sequence of SEQ ID NO:7; and a light chain variable region having the polypeptide sequence of SEQ ID NO:8.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:157, 158, 159, 184, 185, and 186, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:9, and a light chain variable region having a polypeptide sequence at least 85%, preferably 90%, more preferably 95% or more, such as 95%, 96%, 97%, 98%, or 99% identical to SEQ ID NO:10. Preferably, the isolated monoclonal antibody or antigen-binding fragment thereof comprises a heavy chain variable region having the polypeptide sequence of SEQ ID NO:9; and a light chain variable region having the polypeptide sequence of SEQ ID NO:10.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:160, 161, 162, 187, 188, and 189, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:11, and a light chain variable region having a polypeptide sequence at least 85%, preferably 90%, more preferably 95% or more, such as 95%, 96%, 97%, 98%, or 99% identical to SEQ ID NO:12. Preferably, the isolated monoclonal antibody or antigen-binding fragment thereof comprises a heavy chain variable region having the polypeptide sequence of SEQ ID NO:11; and a light chain variable region having the polypeptide sequence of SEQ ID NO:12.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:163, 164, 165, 190, 191, and 192, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:13, and a light chain variable region having a polypeptide sequence at least 85%, preferably 90%, more preferably 95% or more, such as 95%, 96%, 97%, 98%, or 99% identical to SEQ ID NO:14. Preferably, the isolated monoclonal antibody or antigen-binding fragment thereof comprises a heavy chain variable region having the polypeptide sequence of SEQ ID NO:13; and a light chain variable region having the polypeptide sequence of SEQ ID NO:14.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:166, 167, 168, 193, 194, and 195, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:15, and a light chain variable region having a polypeptide sequence at least 85%, preferably 90%, more preferably 95% or more, such as 95%, 96%, 97%, 98%, or 99% identical to SEQ ID NO:16. Preferably, the isolated monoclonal antibody or antigen-binding fragment thereof comprises a heavy chain variable region having the polypeptide sequence of SEQ ID NO:15; and a light chain variable region having the polypeptide sequence of SEQ ID NO:16.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:169, 170, 171, 196, 197, and 198, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:17, and a light chain variable region having a polypeptide sequence at least 85%, preferably 90%, more preferably 95% or more, such as 95%, 96%, 97%, 98%, or 99% identical to SEQ ID NO:18. Preferably, the isolated monoclonal antibody or antigen-binding fragment thereof comprises a heavy chain variable region having the polypeptide sequence of SEQ ID NO:17; and a light chain variable region having the polypeptide sequence of SEQ ID NO:18.

According to another particular aspect, the invention relates to an isolated monoclonal antibody or antigen-binding fragment thereof, wherein the antibody or antigen-binding fragment thereof is chimeric.

According to another particular aspect, the invention relates to an isolated monoclonal antibody or antigen-binding fragment thereof, wherein the antibody or antigen-binding fragment thereof is human or humanized.

In another general aspect, the invention relates to an isolated nucleic acid encoding a monoclonal antibody or antigen-binding fragment thereof of the invention. It will be appreciated by those skilled in the art that the coding sequence of a protein can be changed (e.g., replaced, deleted, inserted, etc.) without changing the amino acid sequence of the protein. Accordingly, it will be understood by those skilled in the art that nucleic acid sequences encoding monoclonal antibodies or antigen-binding fragments thereof of the invention can be altered without changing the amino acid sequences of the proteins.

In another general aspect, the invention relates to a vector comprising an isolated nucleic acid encoding a monoclonal antibody or antigen-binding fragment thereof of the invention. Any vector known to those skilled in the art in view of the present disclosure can be used, such as a plasmid, a cosmid, a phage vector or a viral vector. In some embodiments, the vector is a recombinant expression vector such as a plasmid. The vector can include any element to establish a conventional function of an expression vector, for example, a promoter, ribosome binding element, terminator, enhancer, selection marker, and origin of replication. The promoter can be a constitutive, inducible or repressible promoter. A number of expression vectors capable of delivering nucleic acids to a cell are known in the art and can be used herein for production of an antibody or antigen-binding fragment thereof in the cell. Conventional cloning techniques or artificial gene synthesis can be used to generate a recombinant expression vector according to embodiments of the invention.

In another general aspect, the invention relates to a host cell comprising an isolated nucleic acid encoding a monoclonal antibody or antigen-binding fragment thereof of the invention. Any host cell known to those skilled in the art in view of the present disclosure can be used for recombinant expression of antibodies or antigen-binding fragments thereof of the invention. In some embodiments, the host cells are *E. coli* TG1 or BL21 cells (for expression of, e.g., an scFv or Fab antibody), CHO-DG44 or CHO-K1 cells or HEK293 cells (for expression of, e.g., a full-length IgG antibody). According to particular embodiments, the recombinant expression vector is transformed into host cells by conventional methods such as chemical transfection, heat shock, or electroporation, where it is stably integrated into the host cell genome such that the recombinant nucleic acid is effectively expressed.

In another general aspect, the invention relates to a method of producing a monoclonal antibody or antigen-binding fragment thereof of the invention, comprising culturing a cell comprising a nucleic acid encoding the monoclonal antibody or antigen-binding fragment thereof under conditions to produce a monoclonal antibody or antigen-binding fragment thereof of the invention, and recovering the antibody or antigen-binding fragment thereof from the cell or cell culture (e.g., from the supernatant). Expressed antibodies or antigen-binding fragments thereof can be harvested from the cells and purified according to conventional techniques known in the art and as described herein.

Pharmaceutical Compositions

In another general aspect, the invention relates to a pharmaceutical composition, comprising an isolated monoclonal antibody or antigen-binding fragment thereof of the invention and a pharmaceutically acceptable carrier. The term "pharmaceutical composition" as used herein means a product comprising an antibody of the invention together with a pharmaceutically acceptable carrier. Antibodies of the invention and compositions comprising them are also useful in the manufacture of a medicament for therapeutic applications mentioned herein.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness of a composition according to the invention or the biological activity of a composition according to the invention. According to particular embodiments, in view of the present disclosure, any pharmaceutically acceptable carrier suitable for use in an antibody pharmaceutical composition can be used in the invention.

The formulation of pharmaceutically active ingredients with pharmaceutically acceptable carriers is known in the art, e.g., Remington: The Science and Practice of Pharmacy (e.g. 21st edition (2005), and any later editions). Non-limiting examples of additional ingredients include: buffers, diluents, solvents, tonicity regulating agents, preservatives, stabilizers, and chelating agents. One or more pharmaceutically acceptable carrier can be used in formulating the pharmaceutical compositions of the invention.

In one embodiment of the invention, the pharmaceutical composition is a liquid formulation. A preferred example of a liquid formulation is an aqueous formulation, i.e., a formulation comprising water. The liquid formulation can comprise a solution, a suspension, an emulsion, a microemulsion, a gel, and the like. An aqueous formulation typically comprises at least 50% w/w water, or at least 60%, 70%, 75%, 80%, 85%, 90%, or at least 95% w/w of water.

In one embodiment, the pharmaceutical composition can be formulated as an injectable which can be injected, for example, via an injection device (e.g., a syringe or an infusion pump). The injection can be delivered subcutaneously, intramuscularly, intraperitoneally, intravitreally, or intravenously, for example.

In another embodiment, the pharmaceutical composition is a solid formulation, e.g., a freeze-dried or spray-dried composition, which can be used as is, or whereto the physician or the patient adds solvents, and/or diluents prior to use. Solid dosage forms can include tablets, such as compressed tablets, and/or coated tablets, and capsules (e.g., hard or soft gelatin capsules). The pharmaceutical composition can also be in the form of sachets, dragees, powders, granules, lozenges, or powders for reconstitution, for example.

The dosage forms can be immediate release, in which case they can comprise a water-soluble or dispersible carrier, or they can be delayed release, sustained release, or modified release, in which case they can comprise water-insoluble polymers that regulate the rate of dissolution of the dosage form in the gastrointestinal tract or under the skin.

In other embodiments, the pharmaceutical composition can be delivered intranasally, intrabuccally, or sublingually.

The pH in an aqueous formulation can be between pH 3 and pH 10. In one embodiment of the invention, the pH of the formulation is from about 7.0 to about 9.5. In another embodiment of the invention, the pH of the formulation is from about 3.0 to about 7.0.

In another embodiment of the invention, the pharmaceutical composition comprises a buffer. Non-limiting examples of buffers include: arginine, aspartic acid, bicine, citrate, disodium hydrogen phosphate, fumaric acid, glycine, glycylglycine, histidine, lysine, maleic acid, malic acid, sodium acetate, sodium carbonate, sodium dihydrogen phosphate, sodium phosphate, succinate, tartaric acid, tricine, and tris(hydroxymethyl)-aminomethane, and mixtures thereof. The buffer can be present individually or in the aggregate, in a concentration from about 0.01 mg/ml to about 50 mg/ml, for example from about 0.1 mg/ml to about 20 mg/ml. Pharmaceutical compositions comprising each one of these specific buffers constitute alternative embodiments of the invention.

In another embodiment of the invention, the pharmaceutical composition comprises a preservative. Non-limiting examples of preservatives include: benzethonium chloride, benzoic acid, benzyl alcohol, bronopol, butyl 4-hydroxybenzoate, chlorobutanol, chlorocresol, chlorohexidine, chlorphenesin, o-cresol, m-cresol, p-cresol, ethyl 4-hydroxybenzoate, imidurea, methyl 4-hydroxybenzoate, phenol, 2-phenoxyethanol, 2-phenylethanol, propyl 4-hydroxybenzoate, sodium dehydroacetate, thiomerosal, and mixtures thereof. The preservative can be present individually or in the aggregate, in a concentration from about 0.01 mg/ml to about 50 mg/ml, for example from about 0.1 mg/ml to about 20 mg/ml. Pharmaceutical compositions comprising each one of these specific preservatives constitute alternative embodiments of the invention.

In another embodiment of the invention, the pharmaceutical composition comprises an isotonic agent. Non-limiting examples of the embodiment include a salt (such as sodium chloride), an amino acid (such as glycine, histidine, arginine, lysine, isoleucine, aspartic acid, tryptophan, and threonine), an alditol (such as glycerol, 1,2-propanediol propyleneglycol), 1,3-propanediol, and 1,3-butanediol), polyethyleneglycol (e.g. PEG400), and mixtures thereof. Another example of an isotonic agent includes a sugar. Non-limiting examples of sugars can be mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alpha and beta-HPCD, soluble starch, hydroxyethyl starch, and sodium carboxymethylcellulose. Another example of an isotonic agent is a sugar alcohol, wherein the term "sugar alcohol" is defined as a C(4-8) hydrocarbon having at least one —OH group. Non-limiting examples of sugar alcohols include mannitol, sorbitol, inositol, galactitol, dulcitol, xylitol, and arabitol. The isotonic agent can be present individually or in the aggregate, in a concentration from about 0.01 mg/ml to about 50 mg/ml, for example from about 0.1 mg/ml to about 20 mg/ml. Pharmaceutical compositions comprising each one of these specific isotonic agents constitute alternative embodiments of the invention.

In another embodiment of the invention, the pharmaceutical composition comprises a chelating agent. Non-limiting examples of chelating agents include citric acid, aspartic acid, salts of ethylenediaminetetraacetic acid (EDTA), and mixtures thereof. The chelating agent can be present individually or in the aggregate, in a concentration from about 0.01 mg/ml to about 50 mg/ml, for example from about 0.1 mg/ml to about 20 mg/ml. Pharmaceutical compositions comprising each one of these specific chelating agents constitute alternative embodiments of the invention.

In another embodiment of the invention, the pharmaceutical composition comprises a stabilizer. Non-limiting examples of stabilizers include one or more aggregation inhibitors, one or more oxidation inhibitors, one or more surfactants, and/or one or more protease inhibitors.

In another embodiment of the invention, the pharmaceutical composition comprises a stabilizer, wherein said stabilizer is carboxy-/hydroxycellulose and derivates thereof (such as HPC, HPC-SL, HPC-L and HPMC), cyclodextrins, 2-methylthioethanol, polyethylene glycol (such as PEG 3350), polyvinyl alcohol (PVA), polyvinyl pyrrolidone, salts (such as sodium chloride), sulphur-containing substances such as monothioglycerol), or thioglycolic acid. The stabilizer can be present individually or in the aggregate, in a concentration from about 0.01 mg/ml to about 50 mg/ml, for example from about 0.1 mg/ml to about 20 mg/ml. Pharmaceutical compositions comprising each one of these specific stabilizers constitute alternative embodiments of the invention.

In further embodiments of the invention, the pharmaceutical composition comprises one or more surfactants, preferably a surfactant, at least one surfactant, or two different surfactants. The term "surfactant" refers to any molecules or ions that are comprised of a water-soluble (hydrophilic) part, and a fat-soluble (lipophilic) part. The surfactant can, for example, be selected from the group consisting of anionic surfactants, cationic surfactants, nonionic surfactants, and/or zwitterionic surfactants. The surfactant can be present individually or in the aggregate, in a concentration from about 0.1 mg/ml to about 20 mg/ml. Pharmaceutical compositions comprising each one of these specific surfactants constitute alternative embodiments of the invention.

In a further embodiment of the invention, the pharmaceutical composition comprises one or more protease inhibitors, such as, e.g., EDTA, and/or benzamidine hydrochloric acid (HCl). The protease inhibitor can be present individually or in the aggregate, in a concentration from about 0.1 mg/ml to about 20 mg/ml. Pharmaceutical compositions comprising each one of these specific protease inhibitors constitute alternative embodiments of the invention.

In another general aspect, the invention relates to a method of producing a pharmaceutical composition comprising a monoclonal antibody or antigen-binding fragment thereof of the invention, comprising combining a monoclonal antibody or antigen-binding fragment thereof with a pharmaceutically acceptable carrier to obtain the pharmaceutical composition.

Methods of Use

In another general aspect, the invention relates to a method of treating or preventing an autoimmune disease in a subject in need thereof. The method comprises administering to the subject an isolated monoclonal antibody or antigen binding fragment thereof that specifically binds HLA-Cw6 or a pharmaceutical composition of the invention. The HLA-Cw6 monoclonal antibody or antigen-binding fragment thereof is capable of binding HLA-Cw6 on cells in the subject. Binding of the anti-HLA-Cw6 monoclonal antibody or antigen-binding fragment thereof to a peptide-bound HLA-Cw6 on the cell surface can allow for inhibition of activation of the auto-reactive T cell, and/or can allow for the inhibition of functional binding of the peptide-bound HLA-Cw6 to a T cell receptor (TCR). The anti-HLA-Cw6 monoclonal antibody can, for example, form a bispecific antibody with another monoclonal antibody or antigen-binding fragment that can also inhibit activation of an auto-reactive T cell in the subject.

The functional activity of antibodies and antigen-binding fragments thereof that bind HLA-Cw6 can be characterized by methods known in the art and as described herein. Methods for characterizing antibodies and antigen-binding fragments thereof that bind HLA-Cw6 include, but are not limited to, affinity and specificity assays including Biacore, ELISA, and OctetRed analysis; binding assays to detect the binding of antibodies to HLA-Cw6 on T cells by FACS. According to particular embodiments, the methods for characterizing antibodies and antigen-binding fragments thereof that bind HLA-Cw6 include those described below.

In another general aspect, the invention relates to a method of treating or preventing an autoimmune disease in a subject in need thereof, comprising administering to the subject an isolated monoclonal antibody or antigen binding fragment thereof that specifically binds HLA-Cw6 or a pharmaceutical composition of the invention. The autoimmune disease can, for example, be selected from but not limited to, psoriasis, plaque psoriasis, guttate psoriasis, and psoriatic arthritis.

According to embodiments of the invention, the pharmaceutical composition comprises a therapeutically effective amount of an anti-HLA-Cw6 antibody or antigen-binding fragment thereof. As used herein, the term "therapeutically effective amount" refers to an amount of an active ingredient or component that elicits the desired biological or medicinal response in a subject. A therapeutically effective amount can be determined empirically and in a routine manner, in relation to the stated purpose.

As used herein with reference to anti-HLA-Cw6 antibodies or antigen-binding fragments thereof, a therapeutically effective amount means an amount of the anti-HLA-Cw6 antibody or antigen-binding fragment thereof that modulates an immune response in a subject in need thereof.

According to particular embodiments, a therapeutically effective amount refers to the amount of therapy which is sufficient to achieve one, two, three, four, or more of the following effects: (i) reduce or ameliorate the severity of the disease, disorder or condition to be treated or a symptom associated therewith; (ii) reduce the duration of the disease, disorder or condition to be treated, or a symptom associated therewith; (iii) prevent the progression of the disease, disorder or condition to be treated, or a symptom associated therewith; (iv) cause regression of the disease, disorder or condition to be treated, or a symptom associated therewith; (v) prevent the development or onset of the disease, disorder or condition to be treated, or a symptom associated therewith; (vi) prevent the recurrence of the disease, disorder or condition to be treated, or a symptom associated therewith; (vii) reduce hospitalization of a subject having the disease, disorder or condition to be treated, or a symptom associated therewith; (viii) reduce hospitalization length of a subject having the disease, disorder or condition to be treated, or a symptom associated therewith; (ix) increase the survival of a subject with the disease, disorder or condition to be treated, or a symptom associated therewith; (xi) inhibit or reduce the disease, disorder or condition to be treated, or a symptom associated therewith in a subject; and/or (xii) enhance or improve the prophylactic or therapeutic effect(s) of another therapy.

The therapeutically effective amount or dosage can vary according to various factors, such as the disease, disorder or condition to be treated, the means of administration, the target site, the physiological state of the subject (including, e.g., age, body weight, health), whether the subject is a human or an animal, other medications administered, and whether the treatment is prophylactic or therapeutic. Treatment dosages are optimally titrated to optimize safety and efficacy.

According to particular embodiments, the compositions described herein are formulated to be suitable for the intended route of administration to a subject. For example, the compositions described herein can be formulated to be suitable for intravenous, subcutaneous, or intramuscular administration.

As used herein, the terms "treat," "treating," and "treatment" are all intended to refer to an amelioration or reversal of at least one measurable physical parameter related to an autoimmune disease or disorder (e.g., psoriasis), which is not necessarily discernible in the subject, but can be discernible in the subject. The terms "treat," "treating," and "treatment," can also refer to causing regression, preventing the progression, or at least slowing down the progression of the disease, disorder, or condition. In a particular embodiment, "treat," "treating," and "treatment" refer to an alleviation, prevention of the development or onset, or reduction in the duration of one or more symptoms associated with the disease, disorder, or condition, such as an autoimmune disorder (e.g., psoriasis). In a particular embodiment, "treat," "treating," and "treatment" refer to prevention of the recurrence of the disease, disorder, or condition. In a particular embodiment, "treat," "treating," and "treatment" refer to an increase in the survival of a subject having the disease, disorder, or condition. In a particular embodiment, "treat," "treating," and "treatment" refer to elimination of the disease, disorder, or condition in the subject.

According to particular embodiments, provided are compositions used in the treatment or prevention of an autoimmune disease. For an autoimmune therapy, the compositions can be used in combination with another treatment including, but not limited to, a chemotherapy, an anti-IL-23 mAb, an anti-TNF-alpha mAb, an anti-IL17A mAb, other autoimmune disease drugs, an antibody-drug conjugate (ADC), or a targeted therapy. Anti-HLA-Cw6 antibodies can be used to construct bispecific antibodies with partner mAbs against IL-23, TNF-alpha, IL17A, and/or other T cell surface antigens to treat autoimmune diseases that express both HLA-Cw6 and the specific T cell surface antigen.

As used herein, the term "in combination," in the context of the administration of two or more therapies to a subject, refers to the use of more than one therapy. The use of the term "in combination" does not restrict the order in which therapies are administered to a subject. For example, a first therapy (e.g., a composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

Embodiments

This invention provides the following non-limiting embodiments.

Embodiment 1 is an isolated monoclonal antibody or antigen-binding fragment thereof comprising a heavy chain variable region and a light chain variable region, the heavy chain variable region comprising a heavy chain complementarity determining region 1 (HCDR1), HCDR2, and a HCDR3, the light chain variable region comprising a light chain complementarity determining region 1 (LCDR1), LCDR2, and LCDR3, wherein the HCDR1, HCDR2, HCDR3, LCDR1, LCDR2 and LCDR3 comprise the amino acid sequences of:
  a. SEQ ID NOs: 37, 38, 39, 64, 65, and 66, respectively;
  b. SEQ ID NOs: 40, 41, 42, 67, 68, and 69, respectively;
  c. SEQ ID NOs: 43, 44, 45, 70, 71, and 72, respectively;
  d. SEQ ID NOs: 46, 47, 48, 73, 74, and 75, respectively;
  e. SEQ ID NOs: 49, 50, 51, 76, 77, and 78, respectively;
  f. SEQ ID NOs: 52, 53, 54, 79, 80, and 81, respectively;
  g. SEQ ID NOs: 55, 56, 57, 82, 83, and 84, respectively;
  h. SEQ ID NOs: 58, 59, 60, 85, 86, and 87, respectively; or
  i. SEQ ID NOs: 61, 62, 63, 88, 89, and 90, respectively;
wherein the antibody or antigen-binding fragment thereof specifically binds HLA-C, preferably HLA-Cw6.

Embodiment 2 is an isolated monoclonal antibody or antigen-binding fragment thereof comprising a heavy chain variable region and a light chain variable region, the heavy chain variable region comprising a heavy chain complementarity determining region 1 (HCDR1), HCDR2, and a HCDR3, the light chain variable region comprising a light chain complementarity determining region 1 (LCDR1), LCDR2, and LCDR3, wherein the HCDR1, HCDR2, HCDR3, LCDR1, LCDR2 and LCDR3 comprise the amino acid sequences of:
  a. SEQ ID NOs: 91, 92, 93, 118, 119, and 120, respectively;
  b. SEQ ID NOs: 94, 95, 96, 121, 122, and 123, respectively;
  c. SEQ ID NOs: 97, 98, 99, 124, 125, and 126, respectively;
  d. SEQ ID NOs: 100, 101, 102, 127, 128, and 129, respectively;
  e. SEQ ID NOs: 103, 104, 105, 130, 131, and 132, respectively;
  f. SEQ ID NOs: 106, 107, 108, 133, 134, and 135, respectively;
  g. SEQ ID NOs: 109, 110, 111, 136, 137, and 138, respectively;
  h. SEQ ID NOs: 112, 113, 114, 139, 140, and 141, respectively; or i. SEQ ID NOs: 115, 116, 117, 142, 143, and 144, respectively;

wherein the antibody or antigen-binding fragment thereof specifically binds HLA-C, preferably HLA-Cw6.

Embodiment 3 is an isolated monoclonal antibody or antigen-binding fragment thereof comprising a heavy chain variable region and a light chain variable region, the heavy chain variable region comprising a heavy chain complementarity determining region 1 (HCDR1), HCDR2, and a HCDR3, the light chain variable region comprising a light chain complementarity determining region 1 (LCDR1), LCDR2, and LCDR3, wherein the HCDR1, HCDR2, HCDR3, LCDR1, LCDR2 and LCDR3 comprise the amino acid sequences of:
  a. SEQ ID NOs: 145, 146, 147, 172, 173, and 174, respectively;
  b. SEQ ID NOs: 148, 149, 150, 175, 176, and 177, respectively;
  c. SEQ ID NOs: 151, 152, 153, 178, 179, and 180, respectively;
  d. SEQ ID NOs: 154, 155, 156, 181, 182, and 183, respectively;
  e. SEQ ID NOs: 157, 158, 159, 184, 185, and 186, respectively;
  f. SEQ ID NOs: 160, 161, 162, 187, 188, and 189, respectively;
  g. SEQ ID NOs: 163, 164, 165, 190, 191, and 192, respectively;
  h. SEQ ID NOs: 166, 167, 168, 193, 194, and 195, respectively; or
  i. SEQ ID NOs: 169, 170, 171, 196, 197, and 198, respectively;

wherein the antibody or antigen-binding fragment thereof specifically binds HLA-C, preferably HLA-Cw6.

Embodiment 4 is the isolated monoclonal antibody or antigen-binding fragment thereof of any one of embodiments 1-3, comprising a heavy chain variable region having a polypeptide sequence at least 95%, at least 96%, at least 97%, at least 98%, or at least 99% identical to SEQ ID NO:1, 3, 5, 7, 9, 11, 13, 15, or 17, or a light chain variable region having a polypeptide sequence at least 95%, at least 96%, at least 97%, at least 98%, or at least 99% identical to SEQ ID NO:2, 4, 6, 8, 10, 12, 14, 16, or 18. Embodiment 5 is the isolated monoclonal antibody or antigen-binding fragment thereof of any one of embodiments 1-4, comprising:
  a. a heavy chain variable region having the polypeptide sequence of SEQ ID NO:1, and a light chain variable region having the polypeptide sequence of SEQ ID NO:2;
  b. a heavy chain variable region having the polypeptide sequence of SEQ ID NO:3, and a light chain variable region having the polypeptide sequence of SEQ ID NO:4;
  c. a heavy chain variable region having the polypeptide sequence of SEQ ID NO:5, and a light chain variable region having the polypeptide sequence of SEQ ID NO:6;
  d. a heavy chain variable region having the polypeptide sequence of SEQ ID NO:7, and a light chain variable region having the polypeptide sequence of SEQ ID NO:8;
  e. a heavy chain variable region having the polypeptide sequence of SEQ ID NO:9, and a light chain variable region having the polypeptide sequence of SEQ ID NO:10;
  f. a heavy chain variable region having the polypeptide sequence of SEQ ID NO:11, and a light chain variable region having the polypeptide sequence of SEQ ID NO:12;
  g. a heavy chain variable region having the polypeptide sequence of SEQ ID NO:13, and a light chain variable region having the polypeptide sequence of SEQ ID NO:14;
  h. a heavy chain variable region having the polypeptide sequence of SEQ ID NO:15, and a light chain variable region having the polypeptide sequence of SEQ ID NO:16; or
  i. a heavy chain variable region having the polypeptide sequence of SEQ ID NO:17, and a light chain variable region having the polypeptide sequence of SEQ ID NO:18.

Embodiment 6 is the isolated monoclonal antibody or antigen-binding fragment thereof of any one of embodiments 1-5, wherein the antibody or antigen-binding fragment thereof is chimeric.

Embodiment 7 is the isolated monoclonal antibody or antigen-binding fragment thereof of any one of embodiments 1-6, wherein the antibody or antigen-binding fragment thereof is human or humanized.

Embodiment 8 is the isolated monoclonal antibody or antigen-binding fragment thereof of any one of embodiments 1-8, wherein the antibody or antigen-binding fragment thereof blocks development and activation of T cells, through binding and inhibition of antigen presentation by HLA-Cw6.

Embodiment 9 is an isolated nucleic acid encoding the monoclonal antibody or antigen-binding fragment thereof of any one of embodiments 1-8.

Embodiment 10 is a vector comprising the isolated nucleic acid of embodiment 9.

Embodiment 11 is a host cell comprising the vector of embodiment 10.

Embodiment 12 is a pharmaceutical composition, comprising the isolated monoclonal antibody or antigen-binding fragment thereof of any one of embodiments 1-8 and a pharmaceutically acceptable carrier.

Embodiment 13 is a method of treating or preventing an autoimmune disease in a subject in need thereof, comprising administering to the subject the pharmaceutical composition of embodiment 12.

Embodiment 14 is the method of embodiment 13, wherein the autoimmune disease is selected from the group consisting of psoriasis, plaque psoriasis, guttate psoriasis, and psoriatic arthritis.

Embodiment 15 is a method of inhibiting the activation of an auto-reactive T cell in a subject in need thereof, comprising administering to the subject the pharmaceutical composition of embodiment 12.

Embodiment 16 is a method of inhibiting the functional binding of a T cell receptor (TCR) to a peptide-bound HLA-Cw6 complex in a HLA-Cw6 expressing cell, the method comprising contacting the cell with an isolated monoclonal antibody or antigen-binding fragment thereof of any one of embodiments 1-8, wherein the monoclonal antibody or antigen-binding fragment thereof binds the peptide-bound HLA-Cw6 and inhibits functional binding the TCR to the peptide-bound HLA-Cw6 complex.

Embodiment 17 is the method of embodiment 16, wherein the cell is contacted in vitro.

Embodiment 18 is the method of embodiment 16, wherein the cell is contacted in vivo.

Embodiment 19 is a method of producing the monoclonal antibody or antigen-binding fragment thereof of any one of embodiments 1-8, comprising culturing a cell comprising a nucleic acid encoding the monoclonal antibody or antigen-binding fragment thereof under conditions to produce the monoclonal antibody or antigen-binding fragment thereof and recovering the antibody or antigen-binding fragment thereof from the cell or culture.

Embodiment 20 is a method of producing a pharmaceutical composition comprising the monoclonal antibody or antigen-binding fragment of any one of embodiments 1-8, comprising combining the monoclonal antibody or antigen-binding fragment thereof with a pharmaceutically acceptable carrier to obtain the pharmaceutical composition.

EXAMPLES

Materials and Methods
Generation of Proteins Used

Recombinant HLA-Cw6 with peptides were expressed in both mammalian and bacterial expression systems. For counter-screening, recombinant A2PW23 (rhHLA-A2) (SEQ ID NO:199), MHGW2 (rhHLA-G5) (SEQ ID NO:200) and MO1W6 (β2-microglobulin) (SEQ ID NO:201) antigens were used to identify antibodies with high selectivity to HLA-Cw6. Cell lines stably expressing target antigens were generated using standard cloning, expression and clonal selection methods.

Screening of Hybridoma Supernatants from OmniRat Immunizadon Campaign: Primary Screen of Hybridoma Fusions Against Recombinant Antigens (Immunogens).

96-Well Nunc F96 MaxiSorp plates were coated with a 50 μl/well of a 1 μg/ml solution (PBS) containing a 1:1 mixture of CW6W32 (rhHLA-Cw6/TRAT) (SEQ ID NO:202) and CW6W3.ECO.PP.002/.003 (rhHLA-Cw6 (SEQ ID NO:203)/ARF (SEQ ID NO:219)) antigens for a minimum of 2.5 hours prior to aspiration of the coating solution. The plates were blocked with 200 μl/well blocking solution (0.4% BSA/PBS) for 3-4 days at 4° C. On the day of the assay, the plates were washed 3×300 μl/well with 1×PBST and 50 μl/well of culture supernatants, including control samples, were added and the plate incubated for 1 hour at RT. The plates were washed, as described above, and 50 μl/well of a goat anti-rat IgG Fc-HRP (diluted 1:10K) (Jackson Immunoresearch; West Grove, Pa., #112-036-071) secondary detection reagent, prepared in blocking buffer, was added to each well. The plate was incubated for 30 minutes at RT and then washed as described above. Each well received 50 μl/well of TMB (Thermo Fisher Scientific; Waltham, Mass., #34022) substrate solution and was incubated for 10 minutes prior to the addition of 50 μl/well 1 M HCl (stop solution) (VWR; Radnor, Pa., #3004.324-2.5L). The plates were then read on an EnVision plate reader and the absorbance at $\lambda=450$ nm recorded.

Confirmatory and Selectivity Screen of Hybridoma Fusions Against Recombinant Antigens The hits (880) arising from the primary screen of hybridoma fusions were screened against additional antigens to confirm binding selectivity and specificity.

Six sets of 96-Well Nunc F96 MaxiSorp plates were coated with a single antigen: (1) CW6W3.ECO.PP.002/.003 (rhHLA-Cw6 (SEQ ID NO:203)/ARF (SEQ ID NO:219)), (2) CW6W32 (rhHLA-Cw6/TRAT) (SEQ ID NO:202), (3) CW6W36 (rhHLA-Cw6/ADAMTSL5) (SEQ ID NO:204), (4) A2PW23 (rhHLA-A2) (SEQ ID NO:199), (5) MHGW2 (rhHLA-G5) (SEQ ID NO:200), and (6) MO1W6 (β2-microglobulin) (SEQ ID NO:201). After an overnight incubation at 4° C. with 50 μl/well of a 1 μg/ml antigen coating solution (PBS), the solutions were discarded, and the plates were blocked with 250 μl/well blocking solution (0.4% BSA/PBS) for 3 hours at RT. The plates were washed 3×300 μl/well with 1×PBST and 50 μl/well of culture supernatants, including control samples, were added, and the plates were incubated for 1 hour at RT. The plates were washed, as described above, and 50 μl/well of a goat anti-rat IgG Fc-HRP (diluted 1:10K) (Jackson #112-036-071) secondary detection reagent, prepared in blocking buffer, was added to each well. The plate was incubated for 30 minutes at RT, and then washed as described above. Each well received 50 μl/well of TMB (Thermo #34022) substrate solution and incubated for 10 minutes prior to the addition of 50 μl/well 1 M HCl (stop solution) (VWR #3004.324-2.5L). The plates were then read on an EnVision plate reader and the absorbance at $\lambda=450$ nm recorded.

Confirmatory MSD Cell Binding Screen of HLA-Cw6 Hybridoma Output Hits.

The hits (880) arising from the primary screen of hybridoma fusions were screened against additional antigens to confirm binding selectivity and specificity.

Supernatants from all clones from the fusion of HLA-Cw6 immunized OmniRat lymphocytes with FO myeloma cells were tested for presence of anti-HLA-Cw6 antibodies. Binding was tested against K562 parent and K562 cell lines stably expressing rhHLA-Cw6 (K562-rhHLA-Cw6) (SEQ ID NO:211) and rhHLA-A1 (K562-rhHLA-A1) (SEQ ID NO:212). The cells were seeded at 65000 cells/well into 96-well MSD High Bind plates (MSD #L15XB) and incubated for 1 hour in an incubator set at 37° C. and 5% $CO_2$. The coating solutions were discarded, and the plates blocked with 150 μl/well blocking buffer (20% FBS and 0.18% $NaN_3$ in PBS) for 30 minutes at RT. The blocking solution was discarded, and 50 μl/well of supernatant was added to the assay plates and incubated for 1 hour at RT before washing the plates with 3×300 μl/well PBS. The secondary SulfoTag labeled anti-rat IgG detection antibody (Meso Scale Discovery (MSD); Rockville, Md., #R32AH-1), prepared as a 0.5 mg/ml solution, was then added to the plates at 50 μl/well and incubated for 1 hour at RT before washing the plates as described above. The plates then received 150 μl of a 1×MSD Read Buffer T (surfactant free) (MSD #R92TD-1), and the plates were read on an MSD Sector Plate Reader.

Primary Screen of Antibodies Expressed by Single B Cells from Immunized Ablexis Mice Against Recombinant Antigens.

Supernatants from cultured single B cells were tested for presence of mouse IgG and for anti-HLA-Cw6 antibodies using 384-well MSD High Bind assay plates (MSD #L21XB-4). The 384-well High Bind MSD plates were coated with 10 μl/well of a 1 pg/ml of a goat anti-mouse IgG Fcγ antibody (Jackson #115-006-071) or with CW6W3.ECO.PP.002/.003 (rhHLA-Cw6 (SEQ ID NO:203)/ARF (SEQ ID NO:219)) for 6 hours at RT. The coated plates were washed with 75 μl 1×PBST and 60 μl/well of blocking buffer (0.4% BSA/PBS) were added to all plates. The plates were sealed and incubated overnight at 4° C. On the following day, the plates were washed, as described above, and 10 μl/well of harvested supernatants from the single B cell cultures were incubated in the plates for 2 hours at RT. The plates were washed and 15 μl/well of a 1 pg/ml goat SulfoTag anti-mouse secondary detection antibody (MSD #R32AC-5) was added to the assay plate, and the plate was incubated for 1 hour at RT. The plates were washed and 35 µl/well of 1×MSD Read Buffer T (MSD #R92TC-1) added and the plates read on a MSD Sector Imager 6000.

Primary Screen of Antibodies Expressed by Single B Cells from Immunized Ablexis Mice Against Cell Lines.

Supernatants from cultured single B cells were tested for selective binding to K562 cell line stably expressing rhHLA-Cw6 (SEQ ID NO:211), but not to K562 cell lines stably expressing rhHLA-A1 (K562-rhHLA-A1) (SEQ ID NO:212) or rhHLA-B7 (K562-rhHLA-B7) (SEQ ID NO:213), or to K562 parent cell line. High Bind 384-well MSD plates (MSD #L21XB-4) were coated with 5000 cells/well in 10 µl volume for 1.5 hours in an incubator set at 37° C. and 5% $CO_2$. To block the plates, 60 µl/well of a 20% FBS/0.18% $NaN_3$/PBS solution was added and the plates were incubated for 30 minutes in a 37° C. incubator supplemented with 5% $CO_2$. The blocking solution was discarded and 10 µl/well of harvested supernatants from the single B cell cultures were incubated in the plates for 1.5 hours at RT. The plates were washed with 60 µl/well 1×PBS and 15 µl/well of a 1 µg/ml goat SulfoTag anti-mouse secondary detection antibody (MSD #R32AC-5) was added to the assay plate, and the plate was incubated for 30 minutes at RT. The plates were washed and 35 µl/well of 1×MSD Read Buffer T (surfactant free) (MSD #R92TD-1) was added, and the plates were read on a MSD Sector Imager 6000.

Primary Monoclonal Antibody Screen/Counter-Screen.

K562 parent and K562 cell lines stably expressing rhHLA-Cw6 (K562-rhHLA-Cw6) (SEQ ID NO:211) and rhHLA-B7 (K562-rhHLA-B7) (SEQ ID NO:213) were seeded into 384-well MSD High Bind assay plates (MSD #L21XB-4) at 12000 cells/well density. After a 1-hour incubation at 37° C. and 5% $CO_2$ in an incubator, the plate was aspirated, 50 µl of Starting Block blocking buffer (Thermo Fisher #37542) was added to each well, and the plate was incubated further for 30 minutes at RT. The blocking buffer was aspirated, 20 µl of prepared test antibodies were added to appropriate wells, and the plate was incubated further for 1 hour at RT. The plate was washed three times with 80 µl PBS, and then each well received 20 µl/well of a 1 µg/ml SulfoTag labeled secondary detection antibody solution. After a 1-hour incubation at RT, the plate was washed three times with 80 µl PBS, and 50 µl/well of a 1×MSD Read Buffer T (surfactant free) (MSD #R92TD-1) was added and the plate was read on an MSD Sector 600 Plate Reader.

T Cell Line Activation Assay—Inhibition of IL-2 Release

A Jurkat T cell clone stably expressing both CD8 (SEQ ID NO:216 and SEQ ID NO:217) and TCR-ADAMTSL5 (SEQ ID NO:214 and SEQ ID NO:215) (clone E11) (Jurkat-rhCD8/rhTCR-ADAMTSL5) are stimulated with a LCL.721.221 clone stably expressing rhHLA-Cw6 (LCL.721.221-rhHLA-Cw6) (SEQ ID NO:211) to induce an IL-2 cytokine release response. The cytokine release response is dependent on the ADAM-Abu peptide loading on the LCL.721.221-rhHLA-Cw6 due to the specificity of the TCR-ADAMTSL5 response from the Jurkat cell clone. LCL.721.221-rhHLA-Cw6 were loaded with 0.2 mg/ml ADAM-Abu (SEQ ID NO:218) peptide for 1 hour in a humidified incubator set at 37° C. and supplemented with 5% $CO_2$. The peptide-loaded LCL.721.221-rhHLA-Cw6 cells were plated into a 384-well assay plate at 20 µl/well and incubated with 20 µl of 4× test antibodies for 1 hour in a humidified incubator set at 37° C. and supplemented with 5% $CO_2$. The Jurkat-rhCD8$^+$/rhTCR-ADAMTSL5 cells were then added to the assay plate at 40 µl/well, and the assay plate was incubated for 16-20 hours in a humidified incubator set at 37° C. and supplemented with 5% $CO_2$. At the end of the incubation time, 20 µl/well were harvested and analyzed using a 384-well MSD IL-2 Cytokine assay kit (MSD #K211AHB-2) using the manufacturers recommended protocol.

T Cell Line Activation Assay—Inhibition of CD69 Up-Regulation

Jurkat T cell clones stably expressing TCR-ADAMTSL5 (clone E11) (SEQ ID NO:214 and SEQ ID NO:215) (Jurkat-rhTCR-ADAMTSL5) and TCR-TRAT (SEQ ID NO:225 and SEQ ID NO:226) (clone C5) (Jurkat-rhTCR-TRAT) were stimulated with K562 cell line stably expressing HLA-Cw6 (clone 16) (K562-rhHLA-Cw6) (SEQ ID NO:211) in the presence of cognate peptide to activate the Jurkat T cell clones as measured by up-regulation of CD69 using flow cytometry. In a 96-well assay plate, 50 µl of the K562-rhHLA-Cw6 cells (100 K cells/well) were added and incubated with 50 µl of a 100 µg/ml ADAM-Abu (SEQ ID NO:218) or TRAT (SEQ ID NO:220) peptide solution prepared in assay medium (RPMI 1640+10% FBS) for 1 hour at 37° C. Serially diluted antibodies were then added to the peptide loaded K562-rhHLA-Cw6 cells in the 96-well assay plate and incubated for 1 hour at 37° C. The appropriate Jurkat T cell clones were added at 50 µl/well (50K cells/well) to the assay plates containing the cognate peptide loaded K562-HLA-Cw6 cells, and the plates were incubated at 37° C. for 14-15 hours. After the treatment period was complete, the cells were transferred to a 96-well round-bottom plate (Costar #3799), and the plate was centrifuged at 1300 RPM for 5 minutes at RT. The supernatants were carefully removed, and the cell pellets were resuspended in 50 µl/well with a solution containing FcR Block (Miltenyi Biotec; Bergisch Gladbach, Germany, #130-059-901) and Live/Dead (Ghost Dye Red, APC-Cy7, Tonbo #13-0865-T100) dye in FACS Stain Buffer (BD Pharmingen; San Jose, Calif., #554657). Then the plate was incubated in the dark for 5 minutes on ice. The cells were then incubated for 30 minutes on ice with 50 µl/well with a staining cocktail, prepared with FACS Stain Buffer, containing Cell Trace CFSE (ThermoFisher #C34554) and BV421 anti-human CD69 antibody (mIgG1, clone FN50, BD Pharmingen #562883). At the end of the incubation period, 150 µl/well of FACS Stain Buffer was added to each well, and the plate spun down at 1300 RPM for 5 minutes at RT. The supernatant was removed, and the cells were resuspended in 200 µl/well FACS Stain Buffer for acquisition on a BD FACSCanto flow cytometer. The data was analyzed with FlowJo v10.

LABScreen Assay—Allele Specificity Screen

The LABScreen (One Lambda) assay investigates antibody binding to a panel of 97 Class I HLA alleles (HLA-A, -B, and -C) using a bead-based fluorescent flow technology (Luminex 100; Luminex; Austin, Tex.). In a 96-well assay plate, 5 µl of the LABScreen (One Lambda #LS1A04) beads were incubated with 20 µl of each test antibody (10 µg/ml) for 30 minutes in the dark at RT with gentle shaking. After the incubation was complete, 150 µl of the supplied 1× wash buffer was added to each well, and the plate was centrifuged at 1300×g for 5 minutes at RT. The wash solution was removed by flicking, and the plates were washed one more time. A 1×PE-conjugated anti-human IgG (One Lambda #LSAB-2) solution was prepared and 100 µl/well added to the assay plate. The plate was incubated for 30 minutes in the dark at RT with gentle shaking. The beads were then washed twice as described above, and then 80 µl/well of 1×PBS was added to each well. The plate was analyzed on a Luminex 100 instrument, and the data was analyzed using the Fusion 3.0 Software (One Lambda).

Analysis of Anti-HLA-Cw6 mAbs Binding to HLA-Cw6 Antigen Constructs

Binding of anti-HLA-Cw6 mAbs to multiple HLA-Cw6 antigens was measured on a ProteOn XPR36 protein interaction array system (Bio-Rad; Hercules, Calif.) using GLC sensor chips (Bio-Rad #176-5011). Goat anti-human Fc antibody (Jackson ImmunoResearch (Jackson #109-005-098)) was conjugated to the chip by standard amine coupling in the horizontal orientation for the subsequent capture of anti-HLA-Cw6 mAbs ("ligands") in the vertical orientation. Anti-HLA-Cw6 mAbs were captured at ligand densities ranging from 100 to 200 response units. Binding to each HLA-Cw6 antigen ("analyte") was measured by flowing five antigen concentrations (100 nM diluted down to 1.23 nM in a 3-fold concentration series) in the horizontal orientation over captured mAbs, with a sixth analyte channel containing only buffer (PBST—phosphate-buffered saline supplemented with 0.005% Tween20, pH 7). All analyses were conducted in PBST at 100 μL/min flow rate with association and dissociation times of 180 and 900 seconds, respectively. Chip surface regeneration (release of captured ligand) was achieved by 2 short pulses of 0.85% phosphoric acid (18s contact time at 100 μL/min). Analyte raw data was double referenced by subtraction of the blank surface response at "interspots" (to correct for refractive index changes and any non-specific interactions with the chip surface) and of the buffer blank response (to correct for any baseline drift resulting from mAb dissociation over time). Referenced data were globally fit to a 1:1 simple Langmuir binding model. Kinetic parameters were calculated for each mAb/antigen combination or interaction using Bio-Rad ProteOn Manager software (version 3.1.0.6) with parameter (kon, koff, Rmax) scope and type set to "Grouped" and "Fitted," respectively.

Affinity Measurements of Binding to Recombinant Class I MHC Molecules by Biacore 8K.

Series S CM4 sensor chips (GE Healthcare #BR-1005-34) were prepared by coupling goat anti-human IgG Fc antibody (Jackson #109-005-098) to the chip surface using an amine coupling kit (GE Healthcare #BR-1000-50). The running buffer for all kinetic measurements was 1×HBSP+100 μg/ml BSA and all measurements were obtained at 25° C. Single-cycle kinetic analysis was performed by immobilizing 75-225 RU of test antibodies followed by injections of antigens at three concentrations (3.7-100 nM) with a contact time of 60 seconds and dissociation time of 900 seconds at 60 μl/min flow rate. Resulting sensorgrams were fitted using the 1:1 kinetic model with global $k_a$, $k_d$ and Rmax and RI set to 0.

Epitope Binning—Surface Plasmon Resonance Imaging (SPRi) and Continuous Flow Microspotter (CFM) Method A CFM 2 (Wasatch Microfluidics; Salt Lake City, Utah) was used to create a microarray of 96 mAbs. It draws forty-eight 70-μl plugs of sample from a 96-well microplate into a fluidic manifold which focuses the solutions into an array of 48 micro flow cells on the surface of the SPR substrate (a G-COOH coated prism from Ssens, NL) and cycles the solutions back and forth at 60 μl/min. A 96-well microplate was prepared with 100 μl of each mAb at 30 μg/ml in MES coupling buffer pH 4.5 and loaded into bay 2 of the CFM. A second plate of freshly mixed activating reagents (150 μl 0.4 M EDC and 150 μl 0.1 M sulfo-NHS in a total of 5 ml of MES coupling buffer pH 4.5) was loaded into bay 1. The CFM was then primed with system buffer (PBS+0.01% T20). The anti-HLA-DR4 mAb plate contained 89 mAbs. Once docked, the activating reagents were cycled over the surface for 7 minutes and followed immediately by the first set of mAbs (top half of the mAb plate) and cycled for 15 minutes. Without undocking, the spots were rinsed with the system buffer. Since the CFM prints 48 solutions at a time, it needs to address the surface twice to create the full array of 89 mAbs. After the first print, the CFM was paused to load fresh activation reagents, and the same cycle of 7-minute activation and 15-minute coupling was repeated for the second half of the mAb plate. The printed prism was then loaded into the SPRi reader (MX96, IBIS Technologies; Netherlands), which uses a single flow cell and autosampler configured to address the array with back-and-forth cycled injections of 80 μl per analyte. Once loaded, 1 M ethanolamine (GE Healthcare) was injected across the chip for 15 minutes to quench the excess reactive esters. The chip was then washed with system buffer and the chip image was used to define the reaction spots (i.e., the 96-ligand array) and the interstitial reference spots (two local reference spots per reaction spot). For classical (Sandwich) binning, a co-injection was used, where both antigen and mAb analyte were transported to the flow cell in parallel lines and injected immediately after one another before continuing with regeneration. Antigen (CW6W3.ECO.PP.002/.003 (rhHLA-Cw6 (SEQ ID NO:203)/ARF (SEQ ID NO:219)) was injected for 3 minutes, followed by 20 μg/ml mAb for a further 3 minutes, and then the surfaces were regenerated. All SPRi experiments were conducted in a 96×96 analyte-on-ligand format.

TABLE 12

Surface Plasmon Resonance imaging (SPRi) and Continuous Flow Microspotter (CFM) method

| Group 1 | Group 2 | | Group 3 | Group 4 | Group 5 | Group 6 |
|---|---|---|---|---|---|---|
| CW6B127 | CW6B128 | CW6B329 | CW6B118 | CW6B198 | CW6B150 | CW6B186 |
| CW6B134 | CW6B139 | CW6B332 | CW6B123 | CW6B225 | CW6B231 | CW6B237 |
| CW6B153 | CW6B143 | CW6B334 | CW6B124 | CW6B228 | CW6B232 | |
| | CW6B157 | CW6B337 | CW6B130 | CW6B229 | CW6B384 | |
| | CW6B158 | CW6B338 | CW6B166 | CW6B230 | CW6B388 | |
| | CW6B164 | CW6B339 | CW6B175 | CW6B233 | CW6B389 | |
| | CW6B176 | CW6B340 | CW6B188 | | CW6B392 | |
| | CW6B177 | CW6B341 | CW6B226 | | CW6B396 | |
| | CW6B185 | CW6B344 | CW6B234 | | | |
| | CW6B274 | CW6B345 | CW6B235 | | | |
| | CW6B277 | CW6B348 | CW6B236 | | | |
| | CW6B279 | CW6B349 | CW6B238 | | | |
| | CW6B282 | CW6B350 | CW6B385 | | | |
| | CW6B290 | CW6B351 | CW6B387 | | | |
| | CW6B292 | CW6B352 | CW6B391 | | | |

TABLE 12-continued

Surface Plasmon Resonance imaging (SPRi) and Continuous Flow Microspotter (CFM) method

| Group 1 | Group 2 | | Group 3 | Group 4 | Group 5 | Group 6 |
|---|---|---|---|---|---|---|
|  | CW6B293 | CW6B353 | CW6B393 |  |  |  |
|  | CW6B296 | CW6B354 | CW6B402 |  |  |  |
|  | CW6B297 | CW6B355 | CW6B404 |  |  |  |
|  | CW6B315 | CW6B356 |  |  |  |  |
|  | CW6B316 | CW6B357 |  |  |  |  |
|  | CW6B317 | CW6B359 |  |  |  |  |
|  | CW6B320 | CW6B360 |  |  |  |  |
|  | CW6B321 | CW6B375 |  |  |  |  |
|  | CW6B322 | CW6B376 |  |  |  |  |
|  | CW6B323 | CW6B377 |  |  |  |  |
|  | CW6B325 | CW6B378 |  |  |  |  |
|  | CW6B326 | CW6B383 |  |  |  |  |
|  | CW6B327 | CW6B390 |  |  |  |  |
|  | CW6B328 |  |  |  |  |  |
| 3 | 57 | | 18 | 6 | 8 | 2 |

Epitope Mapping of Anti-HLA-Cw6 mAbs Using H/D Exchange Studies.

Pepsin/Protease XIII Digestion and LC-MS. 5 pg of CW6W3.ECO.PP.002/.003 (rhHLA-Cw6 (SEQ ID NO:203)/ARF (SEQ ID NO:219)) in 130 μL of control buffer (50 mM phosphate, 100 mM sodium chloride at pH 7.4) was denatured by adding 130 μL of 4 M guanidine hydrochloride, 0.85 M TCEP buffer (final pH was 2.5) and incubating the mixture for 3 minutes at 20° C. Then, the mixture was subjected to on-column pepsin/protease XIII digestion using a packed pepsin/protease XIII (w/w, 1:1) column (2.1×30 mm). The resultant peptides were analyzed using an UPLC-MS system comprised of a Waters Acquity UPLC coupled to a Q Exactive™ Hybrid Quadrupole-Orbitrap Mass Spectrometer (Thermo). The peptides were separated on a 50×1 mm C8 column with a 16.5 min gradient from 2-32% solvent B (0.2% formic acid in acetonitrile). Solvent A was 0.2% formic acid in water. The injection valve and pepsin/protease XIII column and their related connecting tubing were inside a cooling box maintained at 16° C. The second switching valve, C8 column and their related connecting stainless steel tubing were inside another chilled circulating box maintained at −6° C. Peptide identification was done through searching MS/MS data against the W6 sequence with Mascot. The mass tolerance for the precursor and product ions were 7 ppm and 0.02 Da, respectively. 100% sequence coverage was achieved for CW6W3.

Hydrogen Deuterium Exchange (HDX). 10 μL of CW6W3.ECO.PP.002/.003 (rhHLA-Cw6 (SEQ ID NO:203)/ARF (SEQ ID NO:219)) (5 pg), 10 μL of CW6W3.ECO.PP.002/.003 (rhHLA-Cw6 (SEQ ID NO:203)/ARF (SEQ ID NO:219)) & CW6B175 mixture or 10 μL of CW6W3.ECO.PP.002/.003 (rhHLA-Cw6 (SEQ ID NO:203)/ARF (SEQ ID NO:219)) & CW6B130 mixture (5 pg: 15 pg), was incubated with 120 μL deuterium oxide labeling buffer (50 mM sodium phosphate, 100 mM sodium chloride at pD 7.4) for 0 s, 60 s, 300 s, 1800 s, or 7200 s at 20° C. Hydrogen/Deuterium (H/D) exchange at each time point was performed in duplicates. The exchange was quenched by adding 130 μL of 4 M guanidine hydrochloride, 0.85 M TCEP buffer (final pH was 2.5). Subsequently, the quenched samples were subjected to on column pepsin/protease XIII digestion and LC-MS analysis as described above. The mass spectra were recorded in MS only mode. Raw MS data was processed using HDX WorkBench, software for the analysis of H/D exchange MS data (J. Am. Soc. Mass Spectrom. 2012, 23 (9), 1512-1521). The deuterium levels were calculated using the average mass difference between the deuterated peptide and its native form (t0).

Example 1: Generation of Antibodies

All lead candidate and tool antibodies were identified from two independent immunization campaigns: (1) OMT OmniRat, and (2) Ablexis mice immunizations.

OmniRats were immunized twice weekly for a total of 12 immunization boosts by following a Repetitive Immunizations Multiple Sites (RIMS) and final cell immunization boost protocol. Recombinant human CW6W3.ECO.PP.002/.003 (rhHLA-Cw6 (SEQ ID NO:203)/ARF (SEQ ID NO:219)) and CW6W32 (rhHLA-Cw6/TRAT) (SEQ ID NO:202) proteins were used for generating antibodies to HLA-Cw6. For the final boost, a HLA-Cw6 overexpressing K562 cell line was inoculated. Sera was collected and assessed for circulating IgG specific antibodies to rhHLA-Cw6 and titers were determined via a solid phase ELISA with antigen coated directly on the plate. Lymph nodes were harvested for B lymphocytes fusion and the supernatants from the hybridomas were screened for binding to target antigens.

In a second approach, Ablexis mice were immunized three different ways: Intraperitoneal injection (IP), a 30 day protocol, and IP/RIMS with mixture of CW6W3.ECO.PP.002/.003 (rhHLA-Cw6 (SEQ ID NO:203)/ARF (SEQ ID NO:219)) and CW6W32 (rhHLA-Cw6/TRAT) (SEQ ID NO:202) for a total of 8 injections over the course of the immunization protocol. A final boost with K562 cells overexpressing hHLA-Cw6 (K562-rhHLA-Cw6) (SEQ ID NO:211) was not performed. At the end of the immunization protocol, B cells were enriched from splenocytes by using AutoMACS MicroBeads to deplete T cells and IgM+ B cells. A portion of cells were fused for hybridoma generation. The remainder of B cells were stained with bt-HLA-CW6 antigen, anti-mouse IgG (Fcy-specific)-AlexaFluor647, anti-human Kappa-PE/Cy7 and sorted by FACS Aria III. Single antigen-specific B cells (positive for msFc, huKappa, and HLA-CW6) were deposited into a 384-well tissue culture plate containing media (Medium E+20% Jurkat conditioned media+0.1 μg/ml msMegaCD40L (Enzo)+5 μg/ml msCpG ODN1826+25 ng/ml msIL-2 (Peprotech)+10 ng/ml msIL-6 (R&D Systems)+17 ng/ml msIL-10 (R&D Systems)+10 μg/ml LPS 026:B6 (Sigma)+1 μg/ml PWM (Sigma)+1800 iMEF feeder cells/well) and a single cell was deposited per well. Sorted cells were incubated for 4 days in 90 μl media and culture supernatants were screened by MSD for presence of mouse IgG antibodies against CW6W3.ECO.PP.002/.003 (rhHLA-Cw6 (SEQ ID NO:203)/ARF (SEQ ID NO:219)) protein and various cell lines (parental, HLA-CW6, HLA-A, and HLA-B-overexpressing).

The supernatants from the OMT hybridomas were tested for binding to multiple recombinant antigens to select for antibodies selective to HLA-Cw6 by standard ELISA. The six target antigens that were coated on the ELISA plate were (1) CW6W3.ECO.PP.002/.003 (rhHLA-Cw6 (SEQ ID NO:203)/ARF (SEQ ID NO:219)), (2) CW6W32 (rhHLA-Cw6/TRAT) (SEQ ID NO:202), (3) CW6W36 (rhHLA-Cw6/ADAMTSL5) (SEQ ID NO:204), (4) A2PW23 (rhHLA-A2) (SEQ ID NO:199), (5) MHGW2 (rhHLA-G5) (SEQ ID NO:200), and (6) M01W6 (β2-microglobulin (SEQ ID NO:201). In addition, supernatants were screened for binding to K562 cells stably expressing HLA-Cw6 (K562-rhHLA-Cw6) (SEQ ID NO:211) and HLA-A1 (K562-rhHLA-A1) (SEQ ID NO:212) and to parent K562 cell line by MSD Cell Binding format. The clones that had specific binding to rhHLA-Cw6, but not to rhHLA-A2, rhHLA-G5, β2-microglobulin, K562-rhHLA-A2 and parent K562 cell line were cloned and expressed as fully human hIgG1-sigma monoclonal antibodies.

The supernatants from the single B cells were screened by coating MSD plates with CW6W3.ECO.PP.002/.003 (rhHLA-Cw6 (SEQ ID NO:203)/ARF (SEQ ID NO:219)) and detecting bound mouse IgG with a SulfoTag anti-mouse IgG secondary antibody. The supernatants were also screened for binding to K562 cell lines stably expressing human HLA-Cw6 (K562-rhHLA-Cw6) (SEQ ID NO:211), HLA-A1 (K562-rhHLA-A1) (SEQ ID NO:212) and HLA-B7 (K562-rhHLA-B7) (SEQ ID NO:213); parent K562 cells were included to exclude non-specific binders.

All antibodies from both antibody discovery campaigns that were identified as HLA-Cw6 specific binders were initially cloned and expressed as hIgG1-sigma monoclonal antibodies. Antibodies meeting Target Molecule Profile criteria were cloned and expressed as hIgG4-PAA monoclonal antibodies.

Example 2: Characterization of Antibodies

Antibodies were identified from the supernatants of hybridoma fusion clones, from the OMT OmniRat immunization, and B cell sorting from Ablexis mice immunizations. From the characterization experiments discussed below, nine (9) unique antibodies that represent 8 antagonist and 1 non-antagonist anti-HLA-Cw6 antibodies with differing combined properties of epitope binding group, antagonist potency, binding selectivity and affinity were identified. In the sections below, the results from each in vitro characterization study is discussed for all 9 antibodies.

Primary Screening of Supernatants from OMT Hybridoma Fusions

Hybridoma supernatants from the OMT OmniRat immunizations were initially screened in a 232×96-Well ELISA to identify clones expressing anti-HLA-Cw6 antibodies that bind CW6W32 (rhHLA-Cw6/TRAT) (SEQ ID NO:202) and CW6W3.ECO.PP.002/.003 (rhHLA-Cw6 (SEQ ID NO:203)/ARF (SEQ ID NO:219)), the immunogens used for immunization. A total of 880 hits were identified from the primary screen. To identify hybridoma clone supernatants with selectivity to rhHLA-Cw6, a confirmatory ELISA screen was performed against multiple recombinant antigens and multiple cell lines stably expressing HLA-I molecules. The antigens in the confirmatory screen were: (1) CW6W3.ECO.PP.002/.003 (rhHLA-Cw6 (SEQ ID NO:203)/ARF (SEQ ID NO:219)), (2) CW6W32 (rhHLA-Cw6RAT) (SEQ ID NO:202), (3) CW6W36 (rhHLA-Cw6/ADAMTSL5) (SEQ ID NO:204), (4) A2PW23 (rhHLA-A2) (SEQ ID NO: 199), (5) MHGW2 (rhHLA-G5) (SEQ ID NO:200), and (6) M01CW6 (rhβ2-macroglobulin) (SEQ ID NO:201). The confirmatory cell binding screen was performed against K562 cell lines stably expressing rhHLA-Cw6 (K562-rhHLA-Cw6) (SEQ ID NO:211) and counter-screened against K562 cells stably expressing rhHLA-A (K562-rAHLA-A) (SEQ ID NO:212), and the K562 parent cell line. A total of 208 hybridoma clone supernatants were selective to HLA-Cw6 based on these screens (Table 1).

TABLE 1

Summary of hits from primary screens against recombinant antigen cell lines
Summary of Confirmatory and Cell Binding Screens of 880 Hybridoma Supernatant Hits

| Screen | Positive Binding Antigens | Negative Binding Antigens | Method | # Hits |
| --- | --- | --- | --- | --- |
| Confirmatory | CW6W3.ECO.PP.002/.003 (rhHLA-Cw6/ARF) CW6W32 (rhHLA-Cw6/TRAT) CW6W36 (rhHLA-Cw6/ADAMTLS5, C6V) | A2PW23 (rhHLA-A2) MHGW2 (rhHLA-G5) M01W6 (β2-macroglobulin) | ELISA | 61 |
| Confirmatory | CW6W3 (rhHLA-Cw6/ARF) CW6W32 (rhHLA-Cw6/TRAT) | CW6W36 (rhHLA-Cw6/ADAMTLS5, C6V) A2PW23 (rhHLA-A) MHGW2 (rhHLA-G5) M01W6 (β2-macroglobulin) | ELISA | 3 |
| Confirmatory | CW6W3.ECO.PP.002/.003 (rhHLA-Cw6/ARF) (negative for CW6W32 and CW6W36) (negative for rhHLA-A, rhHLA-G5 and β2-microglobulin) | CW6W32 (rhHLA-Cw6/TRAT) CW6W36 (rhHLA-Cw6/ADAMTLS5, C6V) A2PW23 (rhHLA-A2) MHGW2 (rhHLA-G5) M01W6(β2-macroglobulin) | ELISA | 21 |
| Cell Binding | K562-rhHLA-Cw6 | K562-rhHLA-A1 K562 Parent | MSD | 123 |
| | | | TOTAL | 208 |

Subsequently, an additional primary cell binding screen was performed on the 208 supernatant hits that included a K562 cell line expressing HLA-B7 (K562-rhHLA-B7) (SEQ ID NO:213) to increase the specificity of the hybridoma clone supernatant panel to HLA-Cw6. From this screen, 49 hybridoma clone supernatants were identified to have selective binding to K562-rhHLA-Cw6 (SEQ ID NO:211) but not to K562-rhHLA-B7 (SEQ ID NO:213) or K562 parent cell lines.

Primary Screens of Single B Cell Supernatants and Purified Antibodies from Ablexis Mice B Cell Sorting Supernatants from 216 cultured single B cells, from an Ablexis mice immunization campaign, that were positive for IgG expression and binding to CW6W3.ECO.PP.002/.003

(rhHLA-Cw6 (SEQ ID NO:203)/ARF (SEQ ID NO:219)) antigen were screened for binding to K562 cells stably expressing HLA-Cw6 (K562-rhHLA-Cw6) (SEQ ID NO:211), HLA-A1 (K562-rhHLA-A1 (SEQ ID NO:212), HLA-B7 (K562-rhHLA-B7) (SEQ ID NO:213) and the parent K562 cell line. From the 216 sorted clones, 11 showed specific binding to K562-HLA-Cw6 but not to K562-HLA-A, -HLA-B or parent cell lines. The 11 hits identified from these screens were cloned into human IgG4-PAA, expressed and purified for further characterizations. Of the 11 supernatant hits identified, 9 were successfully expressed and purified as monoclonal antibodies (Table 2) (6 from Ablexis B-cell (CW6B228, CW6B229, CW6B230, CW6B233, CW6B237, CW6B238) and 3 from OMT Hybridoma (CW6B130, CW6B175, and CW6B188)). The antibodies were sequenced to identify the heavy chain variable regions, light chain variable regions, and heavy and light chain complementarity determining regions (Tables 3-6).

TABLE 2

Identified anti-HLA-Cw6 antibodies

| mAb | DNA ID |
|---|---|
| CW6B130 | CW6M130 |
| CW6B175 | CW6M175 |
| CW6B228 | CW6M228 |
| CW6B229 | CW6M229 |
| CW6B230 | CW6M230 |
| CW6B233 | CW6M233 |
| CW6B237 | CW6M237 |
| CW6B238 | CW6M238 |
| CW6B188 | CW6M188 |

TABLE 3

Anti-HLA-Cw6 heavy chain variable region sequences

| mAb clones | VH | AA SEQ ID NO: | NT SEQ ID NO: |
|---|---|---|---|
| CW6B130 | QLQLQESGPGLVKPSETLSLTCTVSGASISSINYYWGWIRQPPGKGLE WIGSFYYSGNTYYNPSLKSRVTISVDTSKNYFSLKLNSVTAADTAVY YCAREYYDSSGYYPFEPWGQGTLVTVSS | 1 | 19 |
| CW6B175 | EVQLVESGGGLVQPGGSLRLSCAASGFTFTNYWMTWVRQAPGKGLE WVANIKQSGSEKYYVDSVKGRFTISRDNAKNSLYLQMNSLRAEDTAV YYCARTLYEWELEPFDYWGQGTLVTVSS | 3 | 21 |
| CW6B228 | QVQLQESGPGLVKPSETLSLTCTVSGNSIRSYYWSWIRQPAGKGLEWI GRIYISGNTNYNPSLKSRVTMSIDTSKNQFSLKLSSVTAADTAVYYCA RLSGIDAFDIWGQGTMVTVSS | 5 | 23 |
| CW6B229 | QVQLQESGPGLVKPSETLSLTCTVSGNSIRSYYWSWIRQPAGKGLEWI GRIYISGNTNYNPSLKSRVTMSIDTSKNQFSLKLSSVTAADTAVFYCA RLSGIDAFDIWGQGTMVTVSS | 7 | 25 |
| CW6B230 | QVQLQESGPGLVKPSETLSLTCTVSGNSISNYYWSWIRQPAGKGLEWI GRIYITGNTNYNPSLKSRVTMSLDTSKNQFSLKLSSVTAADTAVYYCA RLSGIDAFDIWGQGTMVTVSS | 9 | 27 |
| CW6B233 | QVQLQESGPGLVKPSETLSLTCTVSGNSIRSYYWSWIRQPAGKGLEWI GRIYISGNTNYNPSLKSRVTMSIDTSKNQFSLKLSSVTAADTAVYYCA RLSGIDAFDIWGQGTMVTVSS | 11 | 29 |
| CW6B237 | QVTLKESGPVLVKPTETLTLTCTVSGFSLSNARMGVSWIRQPPG KALEWLAHIFSHDEKFYSTFLKSRLTISKDTSKSQVVLMMTNMD PVDTATYYCARIILSSSGHDAFDIWGQGTMVTVSS | 13 | 31 |
| CW6B238 | QVTLKESGPVLVKPTETLTLTCTVSGFSLNNARMGVSWIRQPPG KALEWLAHMFSSDEKFYRTSLKSRLTISKDTSKSQVVLTMTNMD PVDTATYYCARISLYSSGHDTFDLWGQGTMVTVSS | 15 | 33 |
| CW6B188 | EVQLVESGGGLVQPGGSLRLSCAASGFTFTNYWMTWVRQAPGKG LEWVANIKQSGNEKYYVDSVKGRFTISRDNAKNSLYLQMNSLRAE DTAVYYCARTLYEWELEPFDYWGQGTLVTVSS | 17 | 35 |

VH: heavy chain variable region;
AA: amino acid;
NT: nucleotide (DNA)

TABLE 4

Anti-HLA-Cw6 light chain variable region sequences

| mAb clones | VL | AA SEQ ID NO: | NT SEQ ID NO: |
|---|---|---|---|
| CW6B130 | SYVLTQPPSVSVAPGQTARITCGGDNIGSESVHWYQQKPGQAPVLVV YDDTDRPSGIPERFSGSKSGTTATLTISWVEAGDEADYYCQVWDSSSD HVVFGGGTKLTVL | 2 | 20 |
| CW6B175 | SYVLTQPPSVSVAPGQTARITCGGNRIGSKSVHWYQQKPGQAPVLVV FDDSDRPSGIPERFSGSNSGITATLTISRVEAGDEADYYCQVWDSSNDH VVFGGGTKLTVL | 4 | 22 |
| CW6B228 | DIQMTQSPSSLSASVGDRVTITCQASQDINNYLNWYQQKPGKAPKLLI YDASSLETGVPSRFSGSGSGTDFTFTISSLQPEDFATYYCQQYDDLPITF GQGTRLEIK | 6 | 24 |
| CW6B229 | DIQMTQSPSSLSASVGDRVTITCQASQDISNYLNWYQQKPGKAPKLLI YDASNLETGVPSRFSGSGSGTDFTFTISSLQPEDFATYYCQQYDNLPITF GQGTRLEIK | 8 | 26 |
| CW6B230 | DIQMTQSPSTLSASVGDRVTFTCQASQDITKYLNWYQQKPGKAPKLLI YDASNLETGVPSRFSGSGSGTDFTFTISSLQPEDFATYYCQQYDDLPITF GQGTRLEIK | 10 | 28 |
| CW6B233 | DIQMTQSPSSLSASVGDRVTITCQASQDITNYLNWYQQKPGKAPKLLI YDASNLETGVPSRFSGSGSGTDFTFTISSLQPEDFATYYCQQYDNLPITF GQGTRLEIK | 12 | 30 |
| CW6B237 | AIQMTQSPSSLSASVGDRVTITCRASQDIRHNLGWYQQKPGKAPNLLI YAASSLQSGVPSRFSGSGSGTDFILTISSLQPEDFATFFCLQDYIYPLTFG GGTKVEIK | 14 | 32 |
| CW6B238 | AIQMTQSPSSLSASVGDRVTITCRASQDIRNTLGWYQQKPGKAPNLLI YAASSLQSGVPSRFSGSGSGTDFTLTISSLQPEDFATYYCLQDYDYPLT FGGGTKVEIK | 16 | 34 |
| CW6B188 | SYVLTQPPSVSVAPGQTARITCGGNRIGSKNLHWYQQKPGQAPVLVV YDDSDRPSGIPERFSGSNSGSTATLTISRVEAGDEADYYCQVWDSSRD HVVFGGGTKLTVL | 18 | 36 |

VL: light chain variable region;
AA: amino acid;
NT: nucleotide (DNA).

TABLE 5

Anti-HLA-Cw6 heavy chain complementarity determining regions (HCDR1, HCDR2, and HCDR3)

| mAb | HC CDR1 | ID | HC CDR2 | ID | HC CDR3 | ID |
|---|---|---|---|---|---|---|
| KABAT | | | | | | |
| CW6B130 | SINYYWG | 37 | SFYYSGNTYYNPSLKS | 38 | EYYDSSGYYPFEP | 39 |
| CW6B175 | NYWMT | 40 | NIKQSGSEKYYVDSVKG | 41 | TLYEWELEPFDY | 42 |
| CW6B228 | SYYWS | 43 | RIYISGNTNYNPSLKS | 44 | LS GIDAFDI | 45 |
| CW6B229 | SYYWS | 46 | RIYISGNTNYNPSLKS | 47 | LS GIDAFDI | 48 |
| CW6B230 | NYYWS | 49 | RIYITGNTNYNPSLKS | 50 | LS GIDAFDI | 51 |
| CW6B233 | SYYWS | 52 | RIYISGNTNYNPSLKS | 53 | LS GIDAFDI | 54 |
| CW6B237 | NARMGVS | 55 | HIFSHDEKFYSTFLKS | 56 | IILSSSGHDAFDI | 57 |
| CW6B238 | NARMGVS | 58 | HMFSSDEKFYRTSLKS | 59 | ISLYSSGHDTFDL | 60 |
| CW6B188 | NYWMT | 61 | NIKQSGNEKYYVDSVKG | 62 | TLYEWELEPFDY | 63 |

TABLE 5-continued

Anti-HLA-Cw6 heavy chain complementarity determining regions (HCDR1, HCDR2, and HCDR3)

| mAb | HC CDR1 | ID | HC CDR2 | ID | HC CDR3 | ID |
|---|---|---|---|---|---|---|
| | | | CHOTHIA | | | |
| CW6B130 | GASISSINY | 91 | YYSGN | 92 | EYYDSSGYYPFE | 93 |
| CW6B175 | GFTFTNY | 94 | KQSGSE | 95 | TLYEWELEPFD | 96 |
| CW6B228 | GNSIRSY | 97 | YISGN | 98 | LS GIDAFD | 99 |
| CW6B229 | GNSIRSY | 100 | YISGN | 101 | LS GIDAFD | 102 |
| CW6B230 | GNSISNY | 103 | YITGN | 104 | LS GIDAFD | 105 |
| CW6B233 | GNSIRSY | 106 | YISGN | 107 | LS GIDAFD | 108 |
| CW6B237 | GFSLSNARM | 109 | FSHDE | 110 | IILSSSGHDAFD | 111 |
| CW6B238 | GFSLNNARM | 112 | FS SDE | 113 | ISLYSSGHDTFD | 114 |
| CW6B188 | GFTFTNY | 115 | KQSGNE | 116 | TLYEWELEPFD | 117 |
| | | | IMGT | | | |
| CW6B130 | GASISSINYY | 145 | FYYSGNT | 146 | AREYYDSSGYYPFEP | 147 |
| CW6B175 | GFTFTNYW | 148 | IKQSGSEK | 149 | ARTLYEWELEPFDY | 150 |
| CW6B228 | GNSIRSYY | 151 | IYISGNT | 152 | ARLSGIDAFDI | 153 |
| CW6B229 | GNSIRSYY | 154 | IYISGNT | 155 | ARLSGIDAFDI | 156 |
| CW6B230 | GNSISNYY | 157 | IYITGNT | 158 | ARLSGIDAFDI | 159 |
| CW6B233 | GNSIRSYY | 160 | IYISGNT | 161 | ARLSGIDAFDI | 162 |
| CW6B237 | GFSLSNARMG | 163 | IFSHDEK | 164 | ARIILSSSGHDAFDI | 165 |
| CW6B238 | GFSLNNARMG | 166 | MFSSDEK | 167 | ARISLYSSGHDTFDL | 168 |
| CW6B188 | GFTFTNYW | 169 | IKQSGNEK | 170 | ARTLYEWELEPFDY | 171 |

ID: SEQ ID NO;
HC: Heavy Chain

TABLE 6

Anti-HLA-Cw6 light chain complementarity determining regions (LCDR1, LCDR2, and LCDR3)

| mAb | LC CDR1 | ID | LC CDR2 | ID | LC CDR3 | ID |
|---|---|---|---|---|---|---|
| | | | KABAT | | | |
| CW6B130 | GGDNIGSESVH | 64 | DDTDRPS | 65 | QVWDSSSDHVV | 66 |
| CW6B175 | GGNRIGSKSVH | 67 | DDSDRPS | 68 | QVWDSSNDHVV | 69 |
| CW6B228 | QASQDINNYLN | 70 | DAS SLET | 71 | QQYDDLPIT | 72 |
| CW6B229 | QASQDISNYLN | 73 | DASNLET | 74 | QQYDNLPIT | 75 |
| CW6B230 | QASQDITKYLN | 76 | DASNLET | 77 | QQYDDLPIT | 78 |
| CW6B233 | QASQDITNYLN | 79 | DASNLET | 80 | QQYDNLPIT | 81 |
| CW6B237 | RASQDIRHNLG | 82 | AASSLQS | 83 | LQDYIYPLT | 84 |
| CW6B238 | RASQDIRNTLG | 85 | AASSLQS | 86 | LQDYDYPLT | 87 |
| CW6B188 | GGNRIGSKNLH | 88 | DDSDRPS | 89 | QVWDSSRDHVV | 90 |
| | | | CHOTHIA | | | |
| CW6B130 | DNIGSES | 118 | DDT | 119 | WDSSSDHV | 120 |
| CW6B175 | NRIGSKS | 121 | DDS | 122 | WDSSNDHV | 123 |
| CW6B228 | SQDINNY | 124 | DAS | 125 | YDDLPI | 126 |
| CW6B229 | SQDISNY | 127 | DAS | 128 | YDNLPI | 129 |
| CW6B230 | SQDITKY | 130 | DAS | 131 | YDDLPI | 132 |
| CW6B233 | SQDITNY | 133 | DAS | 134 | YDNLPI | 135 |
| CW6B237 | SQDIRHN | 136 | AAS | 137 | DYIYPL | 138 |
| CW6B238 | SQDIRNT | 139 | AAS | 140 | DYDYPL | 141 |
| CW6B188 | NRIGSKN | 142 | DDS | 143 | WDSSRDHV | 144 |

TABLE 6-continued

Anti-HLA-Cw6 light chain complementarity
determining regions (LCDR1, LCDR2, and LCDR3)

| mAb | LC CDR1 | ID | LC CDR2 | ID | LC CDR3 | ID |
|---|---|---|---|---|---|---|
| | | | IMGT | | | |
| CW6B130 | NIGSES | 172 | DDT | 173 | QVWDSSSDHVV | 174 |
| CW6B175 | RIGSKS | 175 | DDS | 176 | QVWDSSNDHVV | 177 |
| CW6B228 | QDINNY | 178 | DAS | 179 | QQYDDLPIT | 180 |
| CW6B229 | QDISNY | 181 | DAS | 182 | QQYDNLPIT | 183 |
| CW6B230 | QDITKY | 184 | DAS | 185 | QQYDDLPIT | 186 |
| CW6B233 | QDITNY | 187 | DAS | 188 | QQYDNLPIT | 189 |
| CW6B237 | QDIRHN | 190 | AAS | 191 | LQDYIYPLT | 192 |
| CW6B238 | QDIRNT | 193 | AAS | 194 | LQDYDYPLT | 195 |
| CW6B188 | NRIGSKN | 196 | DDS | 197 | WDSSRDHV | 198 |

ID: SEQ ID NO;
LC: Light Chain

The expressed and purified monoclonal antibodies were screened for selective binding to K562-rhHLA-Cw6 cell lines but not to K562-rehHLA-B7 or K562 parent cell lines using the MSD Cell Binding assay format. A total of 7 mAbs met criteria for selectivity in binding K562-rhHLA-Cw6 but not K562-rhHLA-B7 or parent K562 cell line (Table 7).

TABLE 7

HLA-Cw6 selective hits from purified monoclonal
antibodies derived from B cell sorting

| mAb | Source | 1) HLA-B7 Specific (K562-rhHLA-B7/K562 Parent) | 2) HLA-Cw6 Specific (K562-rhHLA-Cw6/K562 Parent) | 3) HLA-Cw6 Selective (K562-rhHLA-Cw6 specific/K562-rhHLA-B7 specific) |
|---|---|---|---|---|
| CW6B228 | Single B Cell | 1.0 | 75 | 78 |
| CW6B229 | Single B Cell | 1.0 | 18 | 18 |
| CW6B230 | Single B Cell | 0.7 | 40 | 61 |
| CW6B232 | Single B Cell | 1.2 | 15 | 13 |
| CW6B233 | Single B Cell | 0.8 | 36 | 44 |
| CW6B237 | Single B Cell | 0.9 | 14 | 16 |
| CW6B238 | Single B Cell | 0.9 | 14 | 15 |

1) HLA-B7 Specific antibodies are those that have a ratio >5 of [K562-rhHLA-B7 binding signal/K562 parent binding signal]
2) HLA-Cw6 Specific antibodies are those that have a ratio >5 of [K562-rhHLA-Cw6 binding signal/K562 parent binding signal]
3) HLA-Cw6 Selective antibodies are those that have a ratio >4 of [K562-rhHLA-Cw6 specific/K562-rhHLA-B7 specific]

Functional Activity Screening of Purified Monoclonal Antibodies (IL-2 & CD69)

The purified antibodies identified from the primary screening of OMT OmniRat hybridoma and Ablexis B cell sorting were characterized for functional activity in two separate, but orthogonal, assays: (1) inhibition of HLA-Cw6/ADAMTSL5-Abu dependent IL-2 release in a T cell line, and (2) inhibition of HLA-Cw6/ADAM-TSL5 and HLA-Cw6/TRAT dependent CD69 up-regulation in T cell lines.

The IL-2 inhibition functional screen was performed at 3 antibody concentrations to rank-order the antibodies based on % inhibition of IL-2 release. Briefly, LCL-721.221-rhHLA-Cw6 cells (clone 28) (SEQ ID NO:211), which were loaded with ADAMTSL5-Abu peptide (SEQ ID NO:218), were co-cultured with a Jurkat T cell clone expressing human TCR-ADAMTSL5 receptor (SEQ ID NO:214 and SEQ ID NO:215) (Jurkat-rhTCR-ADAMTSL5) (HLA-Cw6/ADAMTSL5-Abu peptide is a cognate ligand). In the absence of antagonist anti-HLA-Cw6 antibodies, or in the presence of negative controls, the stimulated Jurkat T cell clone secretes measurable IL-2. However, treatment of the co-culture with anti-HLA-Cw6 antagonist antibodies inhibit the secretion of IL-2 and provides a method for screening HLA-Cw6 specific antibodies for antagonist activities. From a panel of HLA-Cw6 specific antibodies, seven (7) possess good efficacy in antagonizing HLA-Cw6 dependent IL-2 release by the Jurkat T cell line that is comparable to positive control anti-HLA-Cw6 antibodies (CW6B123 and CW6B124). An antibody with high specificity to HLA-C, which did not show antagonist activity was also included in the panel of antibodies (Table 8).

TABLE 8

% Inhibition of IL-2 Secretion

| | | | IL-2 % Inhibition (8.5 nM mAb) | |
|---|---|---|---|---|
| No. | mAb | Source | HLA-Cw6-00290 | HLA-Cw6-00254 |
| 1 | CW6B130 | OMT, Hybridoma | 100 | 100 |
| 2 | CW6B175 | OMT, Hybridoma | 96 | 85 |
| 3 | CW6B228 | Ablexis Single B cells | 100 | n/a |
| 4 | CW6B229 | Ablexis Single B cells | 86 | n/a |
| 5 | CW6B230 | Ablexis Single B cells | 93 | n/a |
| 6 | CW6B233 | Ablexis Single B cells | 91 | n/a |
| 7 | CW6B237 | Ablexis Single B cells | 59 | n/a |
| 8 | CW6B238 | Ablexis Single B cells | 86 | n/a |
| 9 | CW6B188 | OMT, Hybridoma | n/a | 9 |
| 10 | CNTO9412 | Isotype Ctrl | 21 | 9 |
| 11 | CW6B123 | Positive Ctrl | 99 | 98 | n/a indicates that sample was not included in experiment

Figure 2:
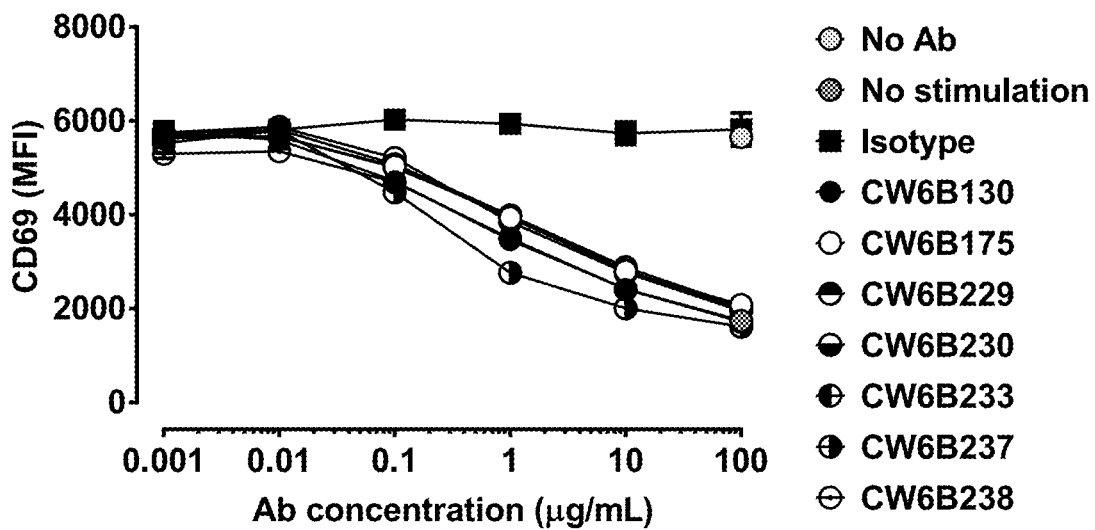
FIG. 2 shows a graph demonstrating the inhibition of HLA-Cw6/TRAT dependent CD69 up-regulation on T cell line by anti-HLA-C antibodies.
Figure 3A:
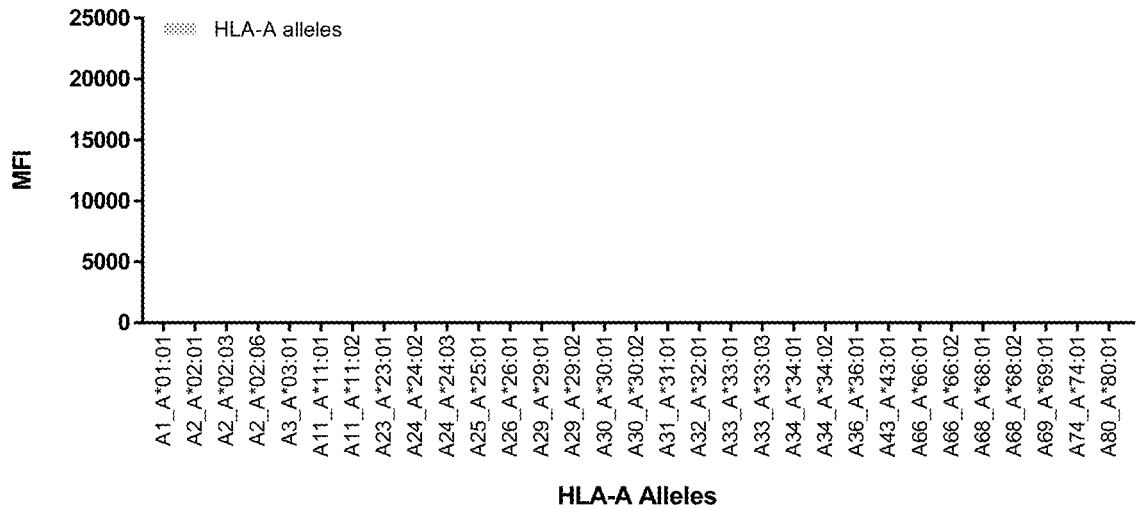
FIGS. 3A-3C show graphs demonstrating LabScreen Class I MHC allele binding profiles for the CW6B130.001 Anti-HLA-C antibody.
Figure 3B:
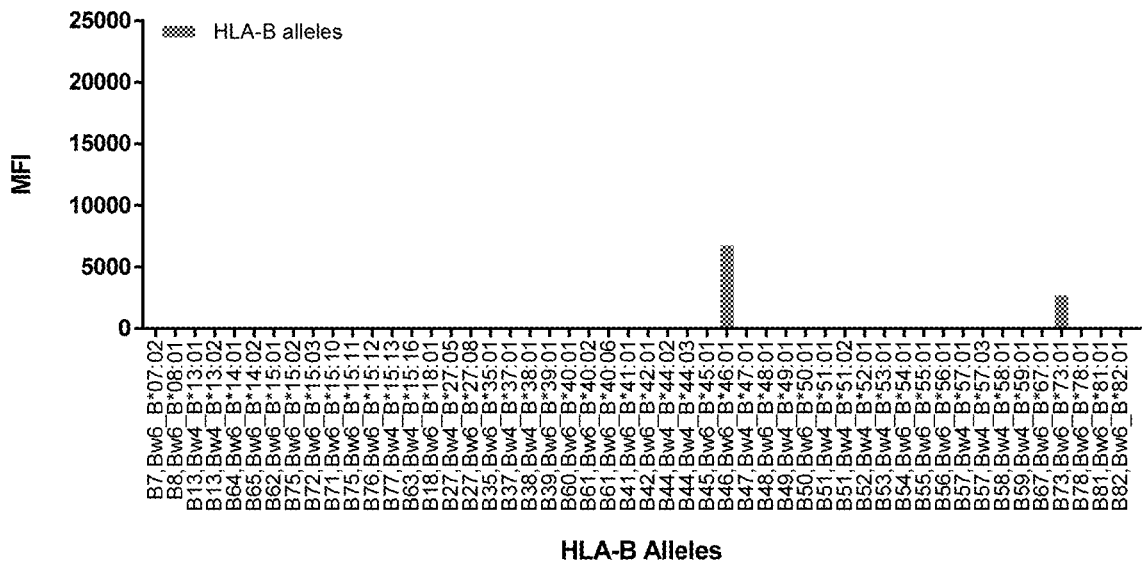
Figure 3C:
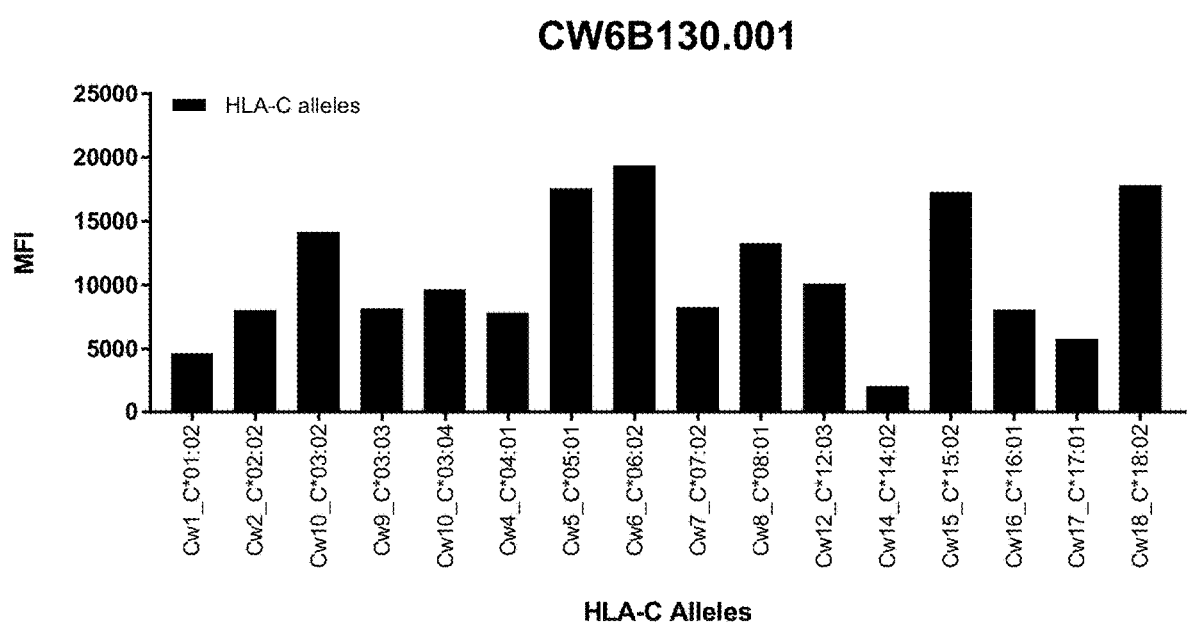
Figure 4A:
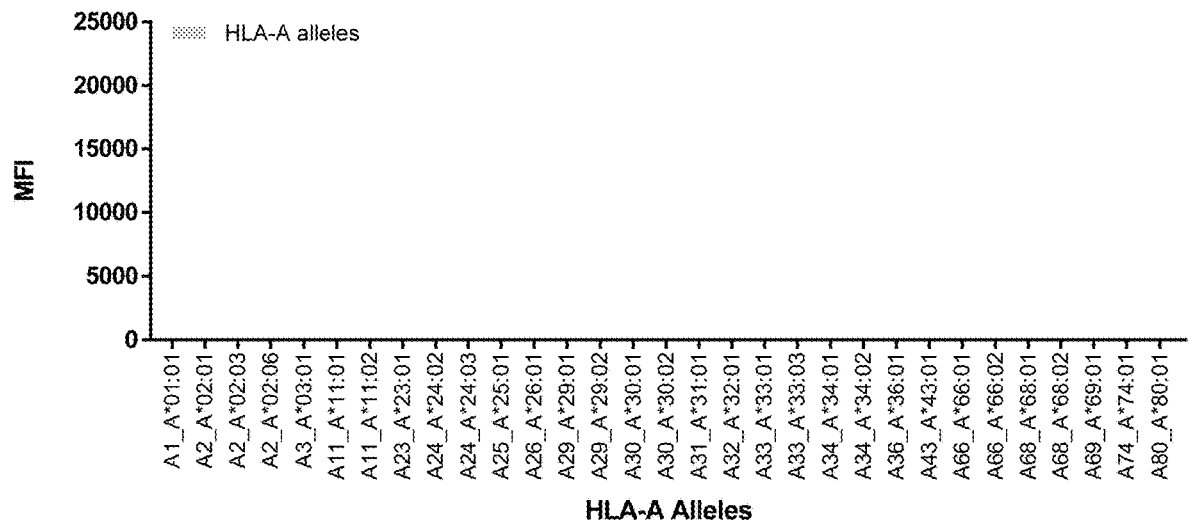
FIGS. 4A-4C show graphs demonstrating LabScreen Class I MHC allele binding profiles for the CW6B175.001 Anti-HLA-C antibody.
Figure 4B:
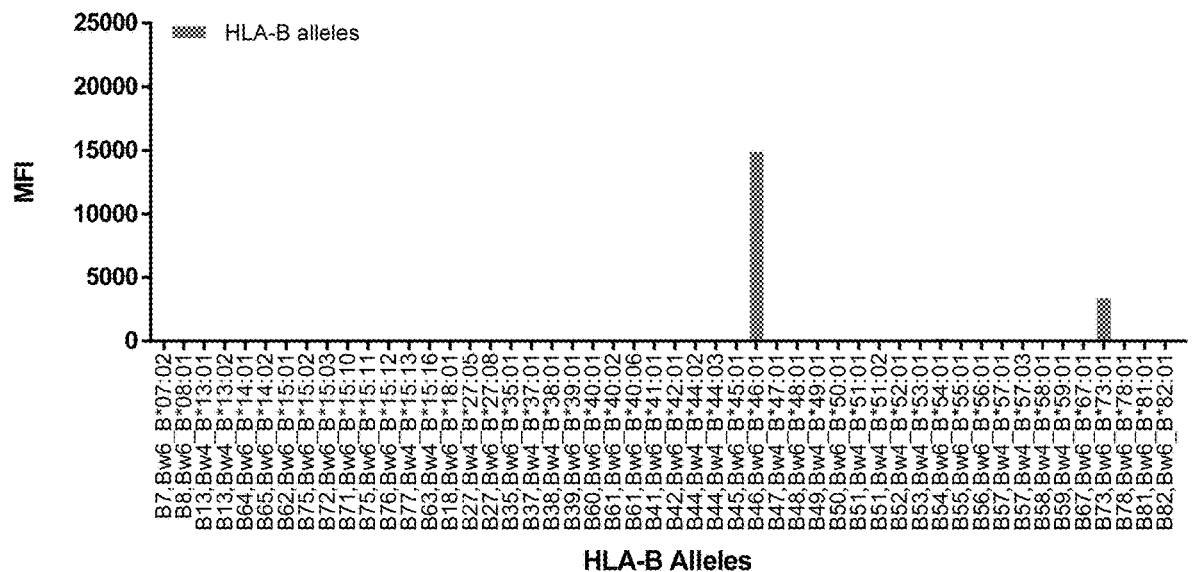
Figure 4C:
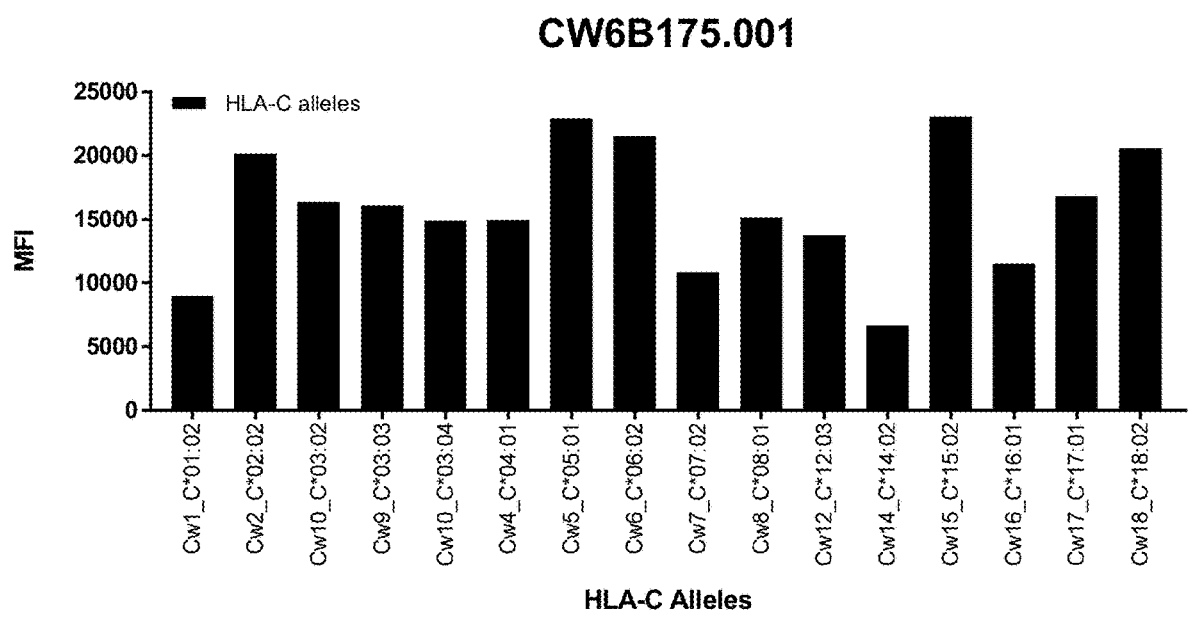
Figure 5A:
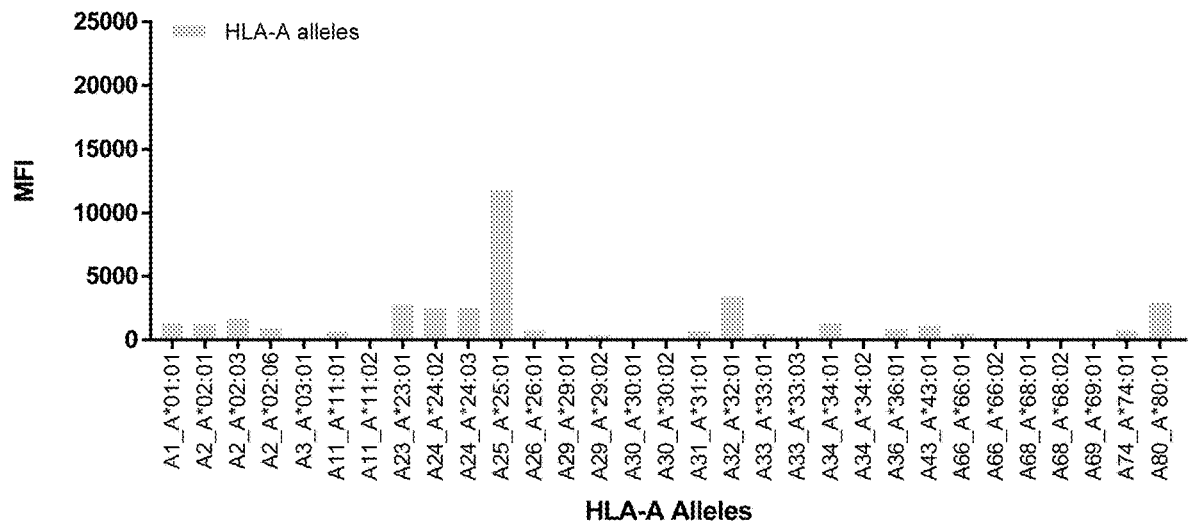
FIGS. 5A-5C show graphs demonstrating LabScreen Class I MHC allele binding profiles for the CW6B228.001 Anti-HLA-C antibody.
Figure 5B:
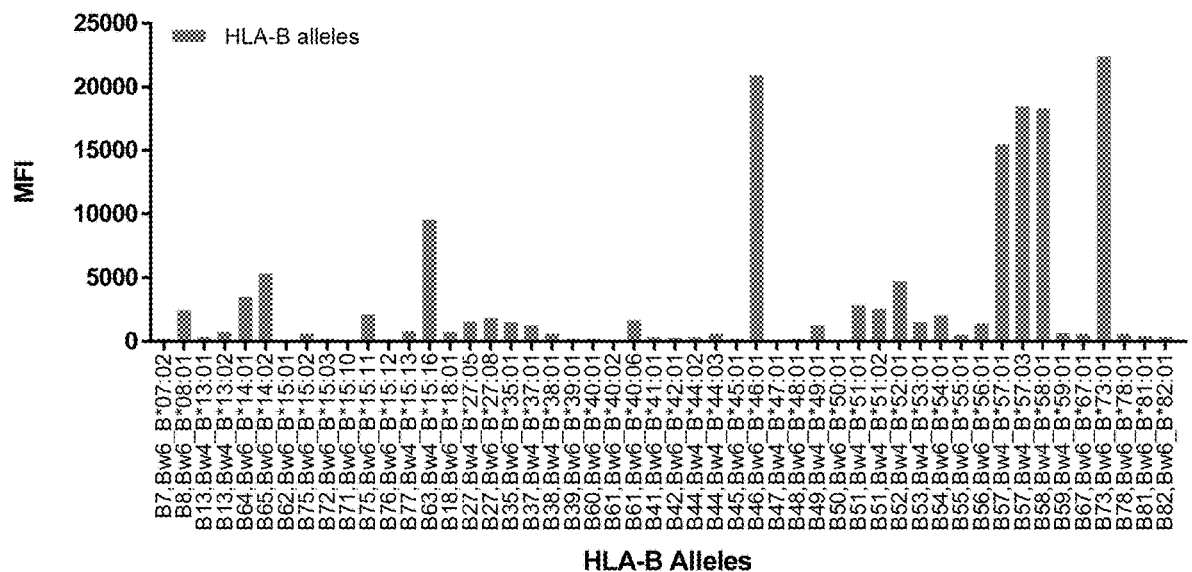
Figure 5C:
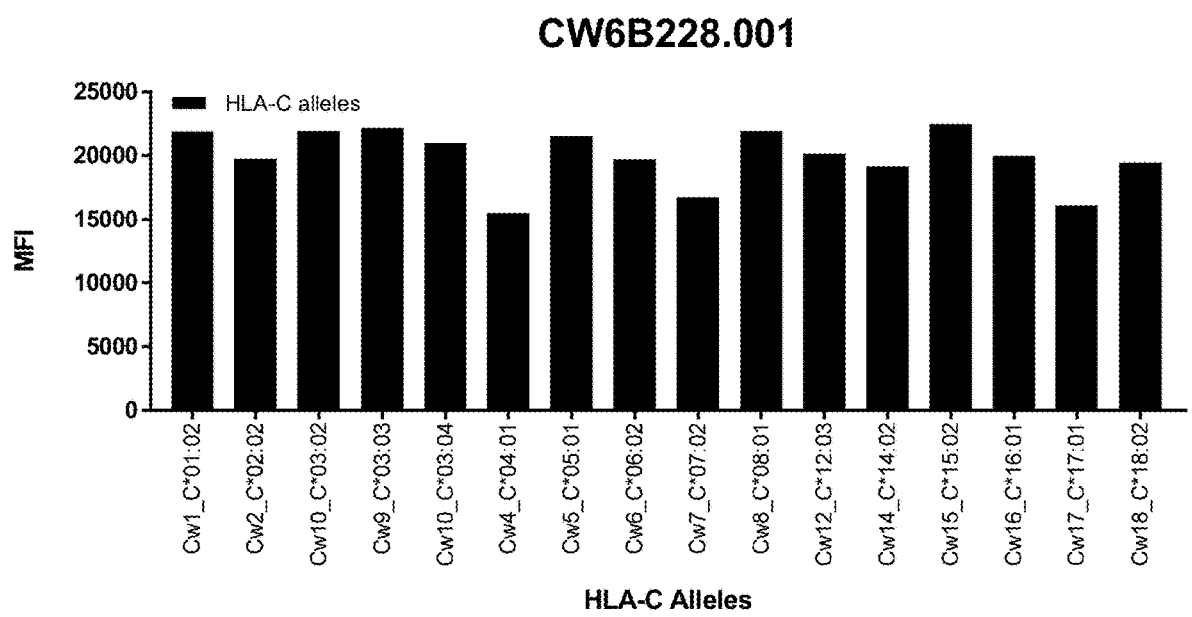
Figure 6A:
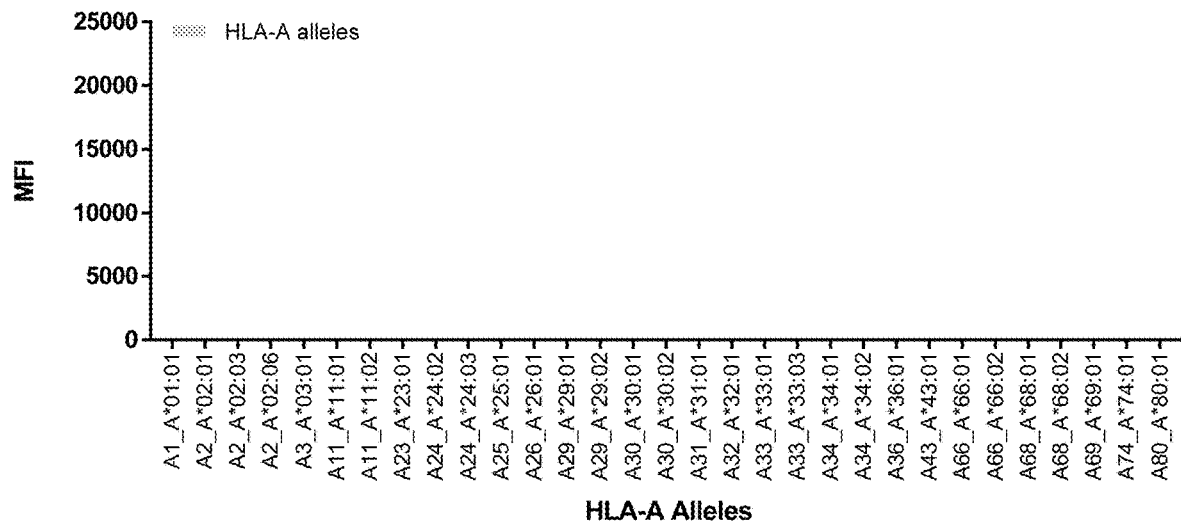
FIGS. 6A-6C show graphs demonstrating LabScreen Class I MHC allele binding profiles for the CW6B229.001 Anti-HLA-C antibody.
Figure 6B:
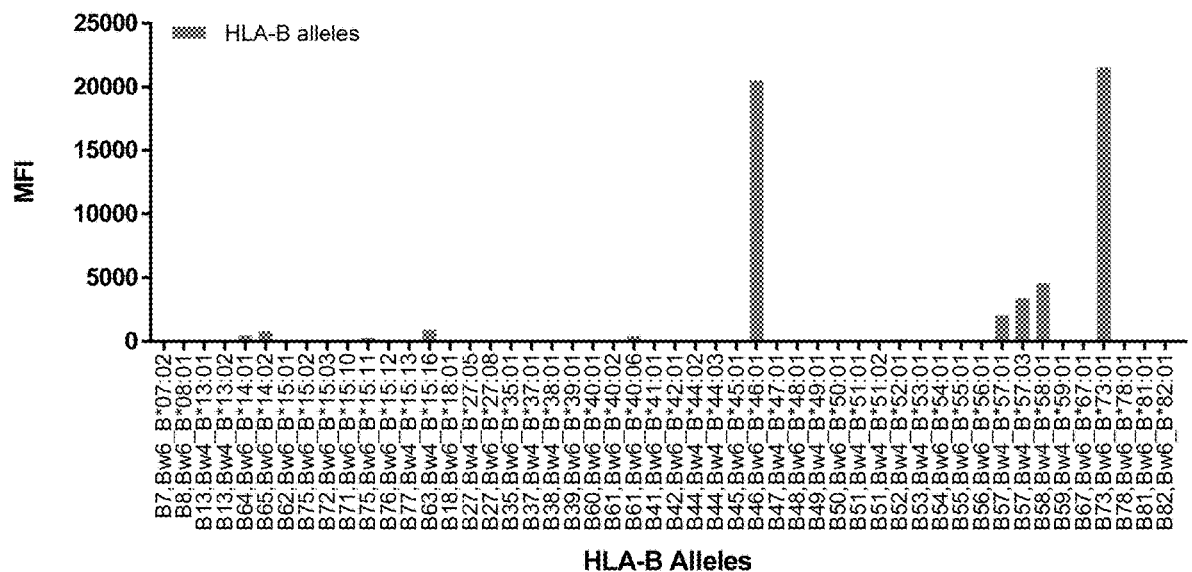
Figure 6C:
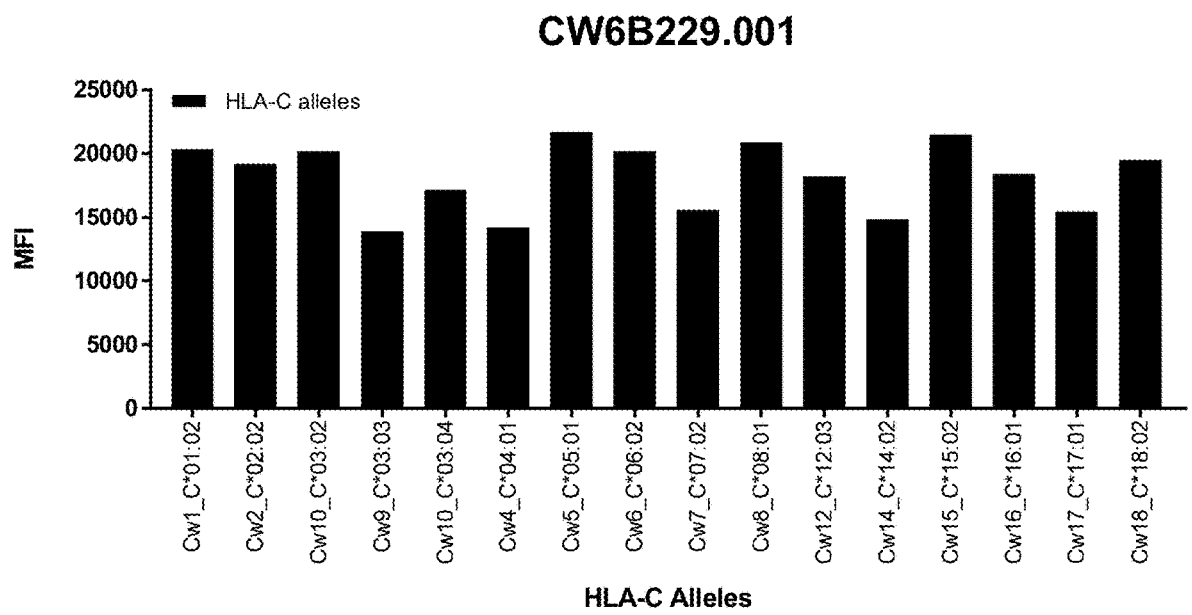
Figure 7A:
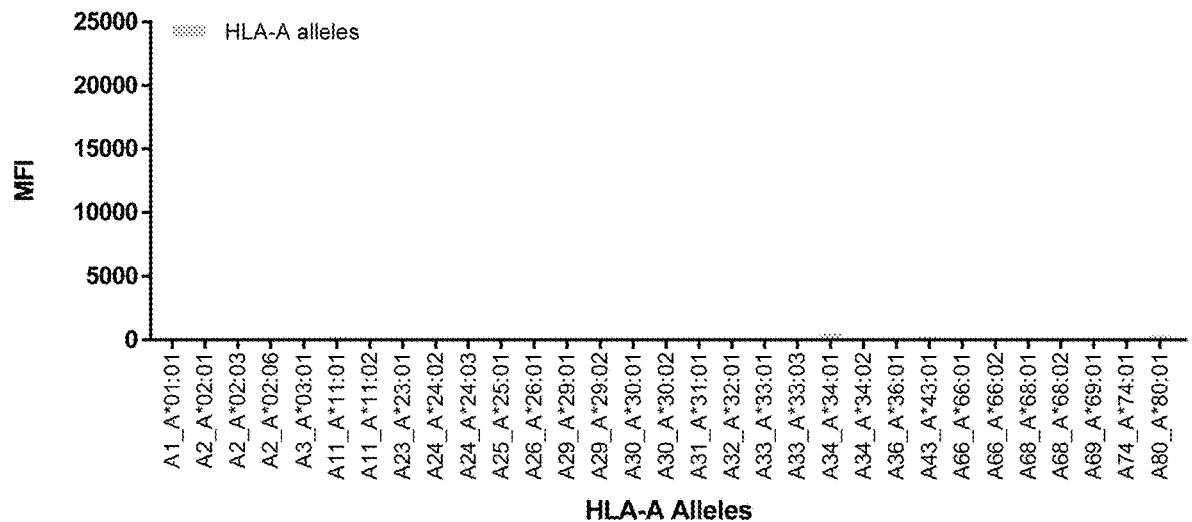
FIGS. 7A-7C show graphs demonstrating LabScreen Class I MHC allele binding profiles for the CW6B230.001 Anti-HLA-C antibody.
Figure 7B:
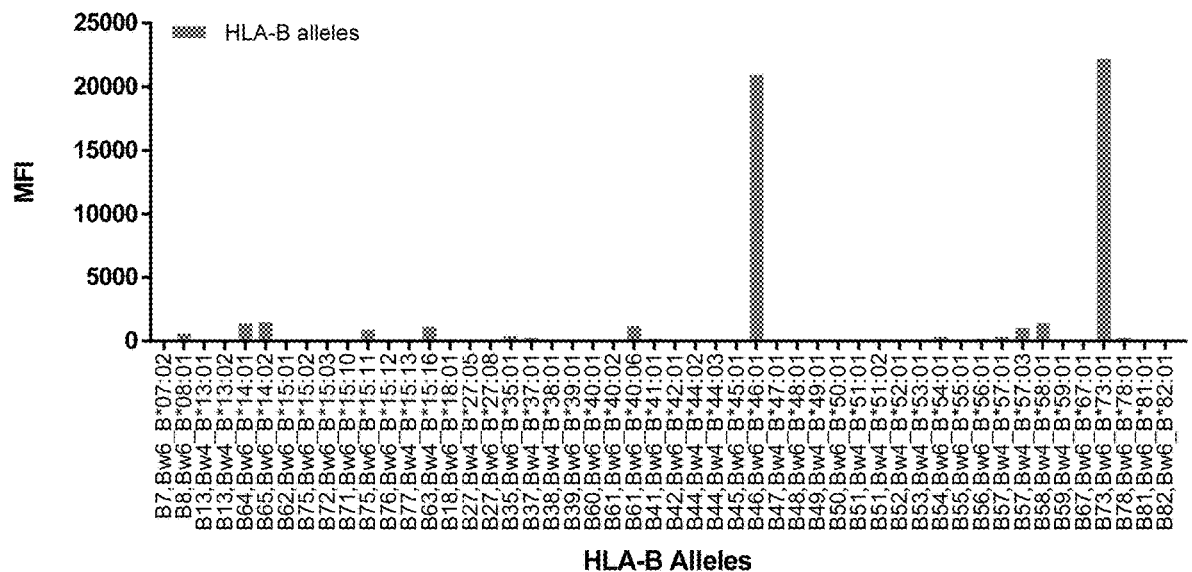
Figure 7C:
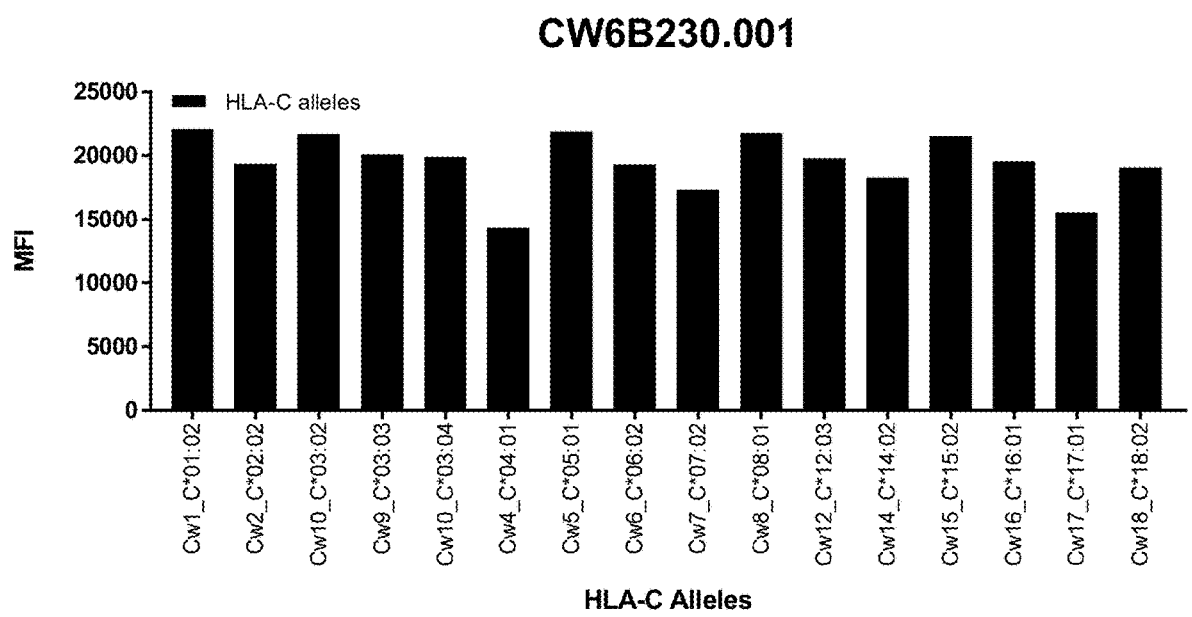
Figure 8A:
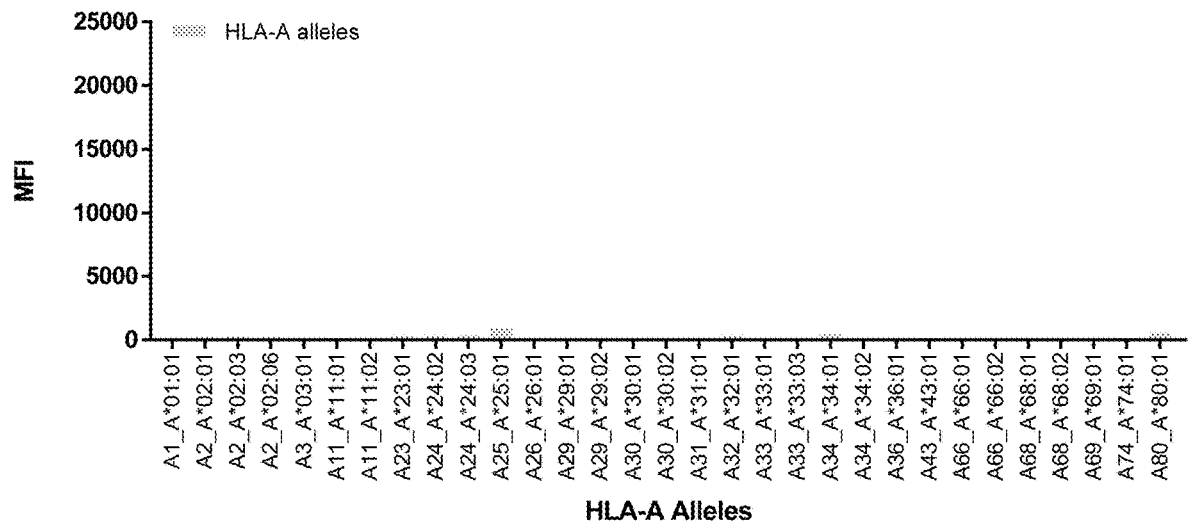
FIGS. 8A-8C show graphs demonstrating LabScreen Class I MHC allele binding profiles for the CW6B233.001 Anti-HLA-C antibody.
Figure 8B:
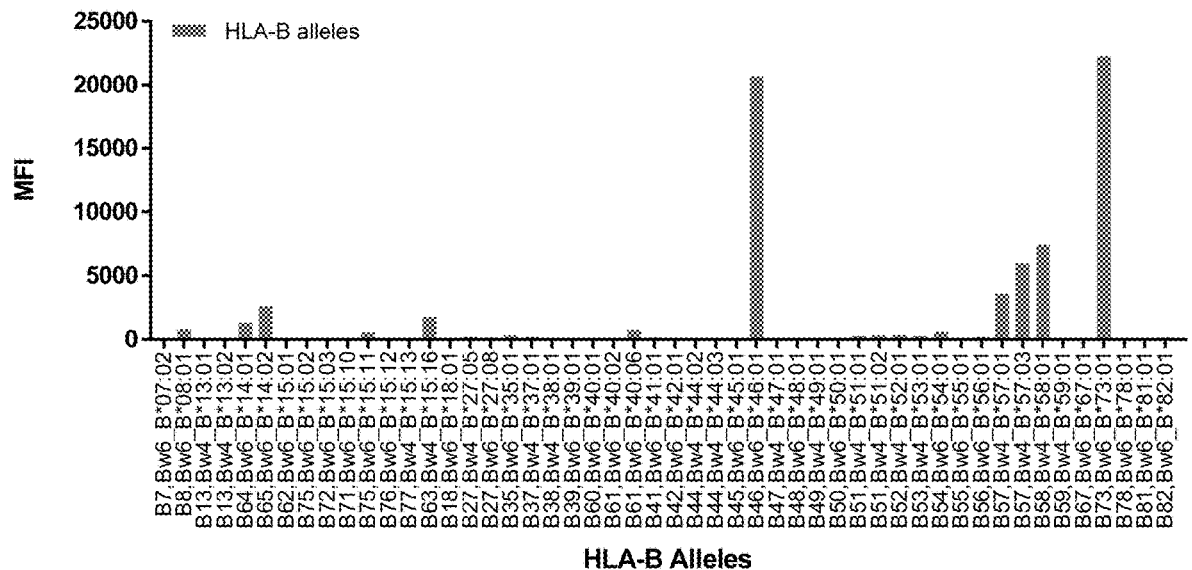
Figure 8C:
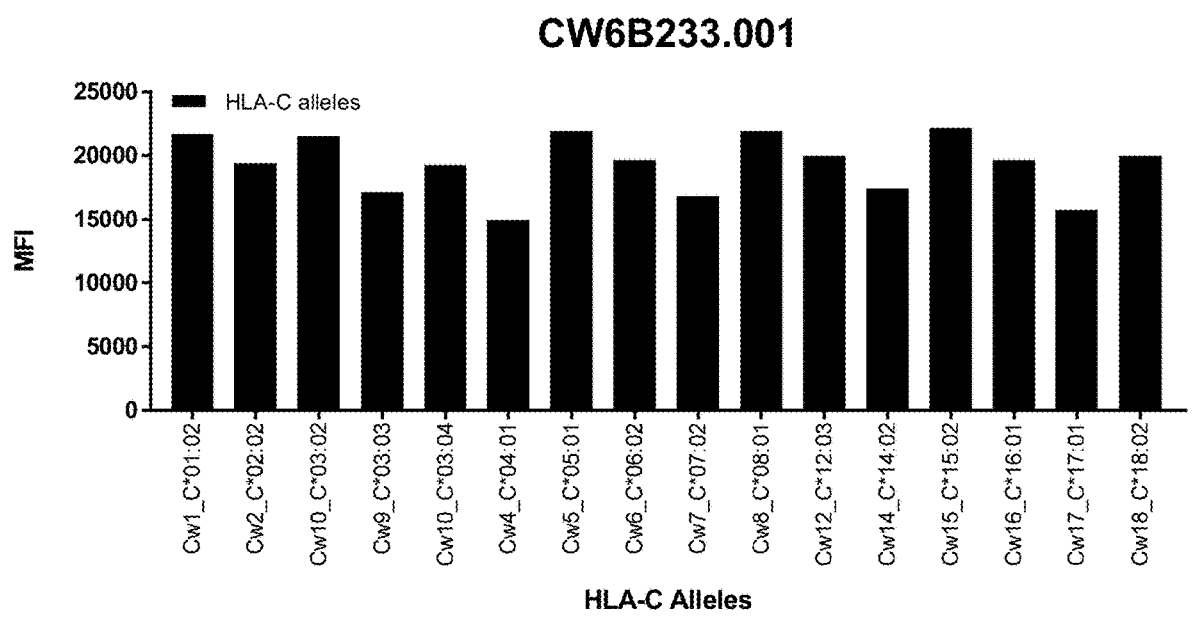
Figure 9A:
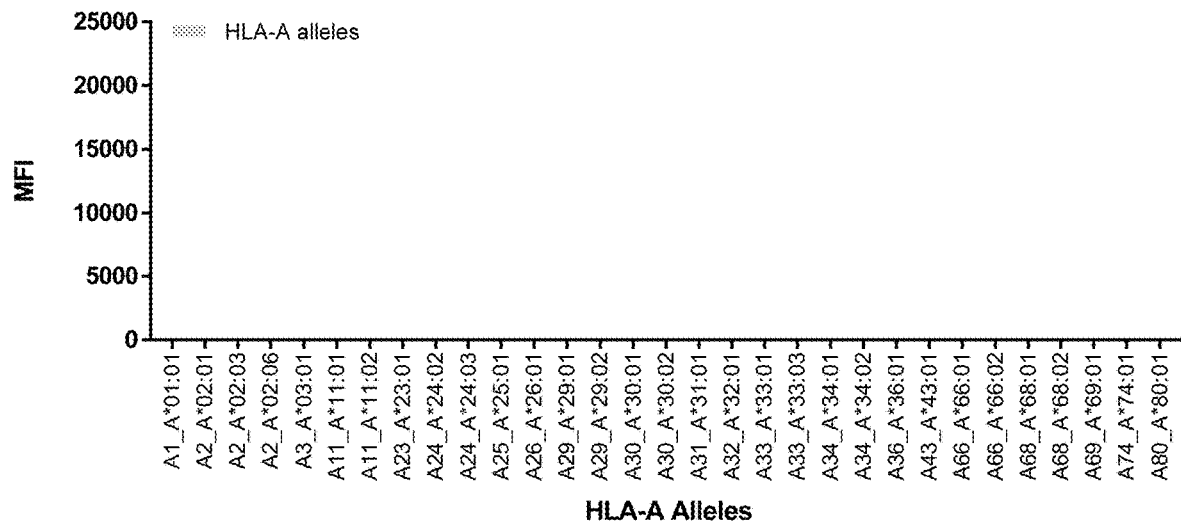
FIGS. 9A-9C show graphs demonstrating LabScreen Class I MHC allele binding profiles for the CW6B237.001 Anti-HLA-C antibody.
Figure 9B:
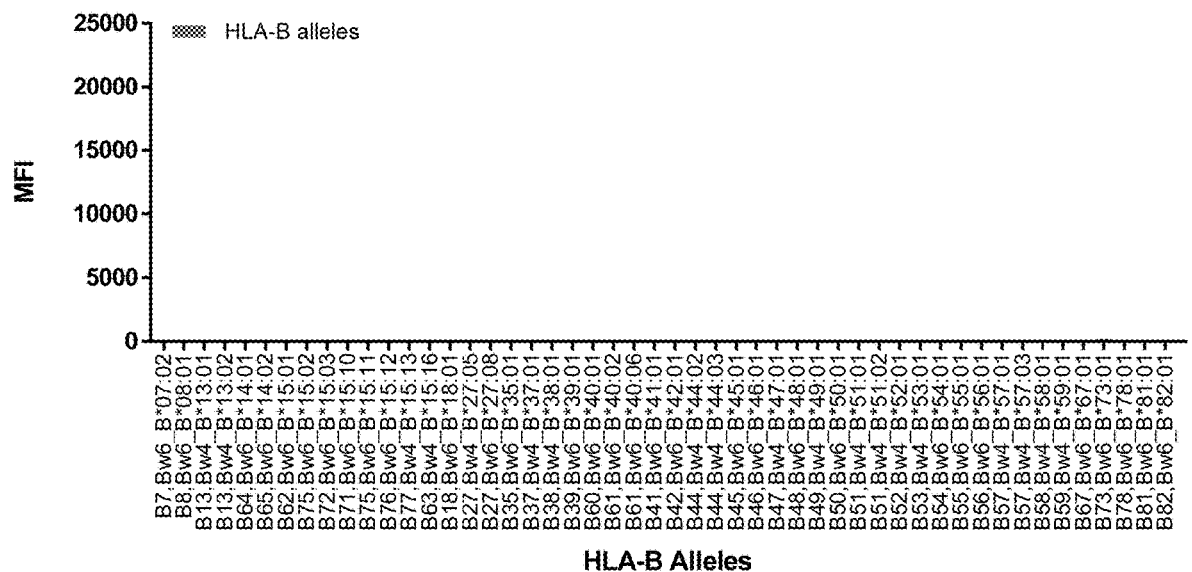
Figure 9C:
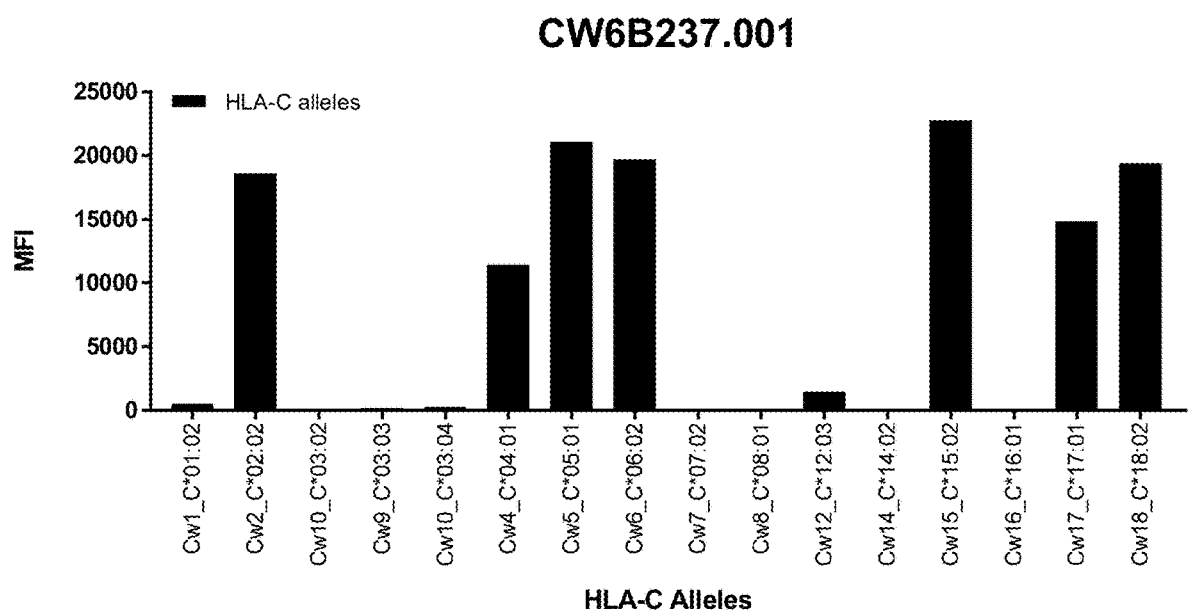
Figure 10A:
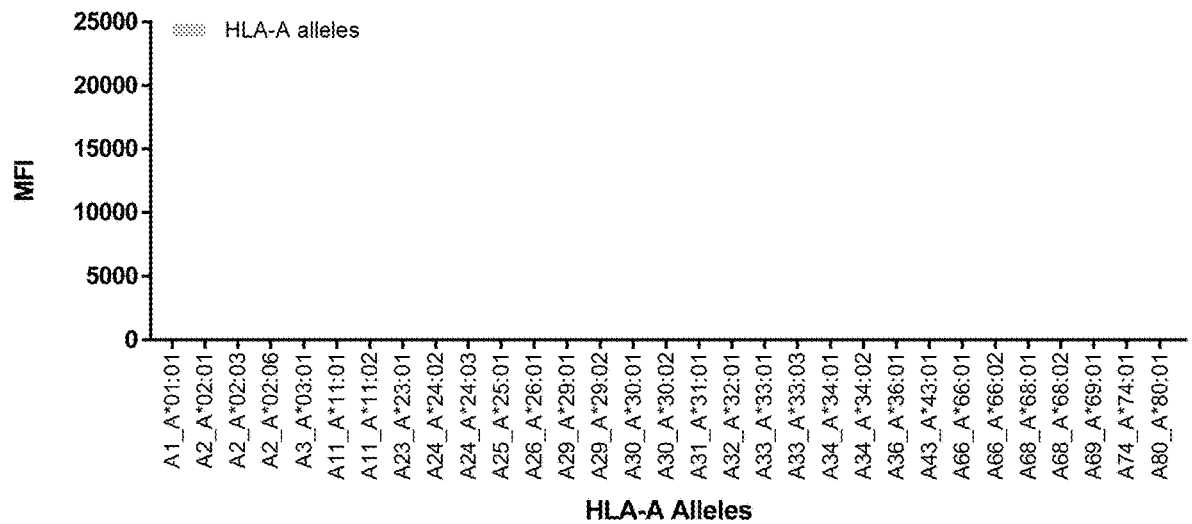
FIGS. 10A-10C show graphs demonstrating LabScreen Class I MHC allele binding profiles for the CW6B238.001 Anti-HLA-C antibody.
Figure 10B:
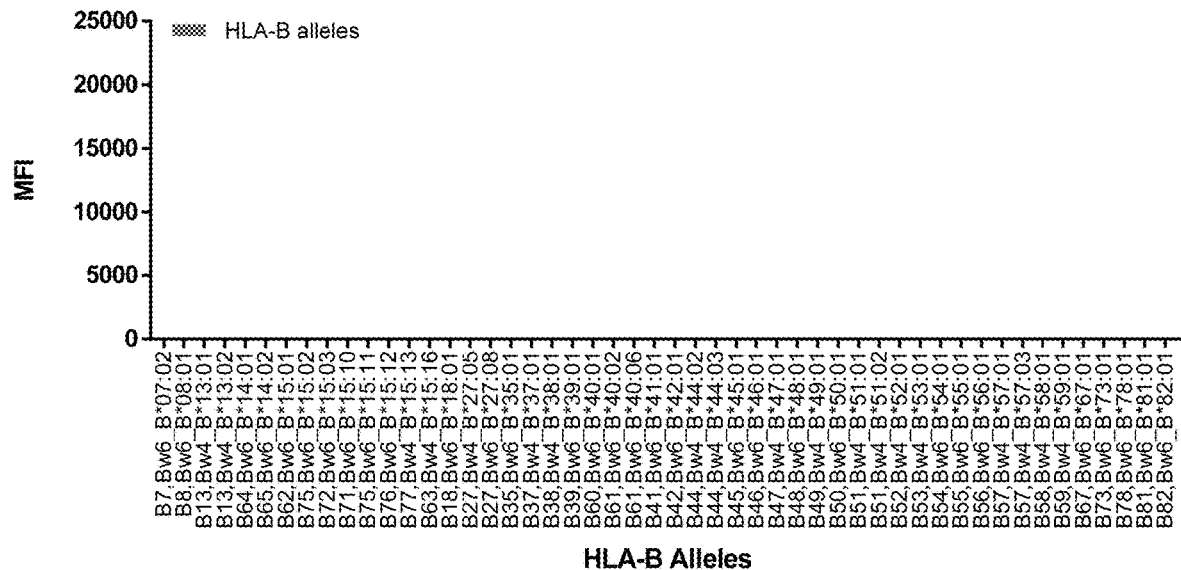
Figure 10C:
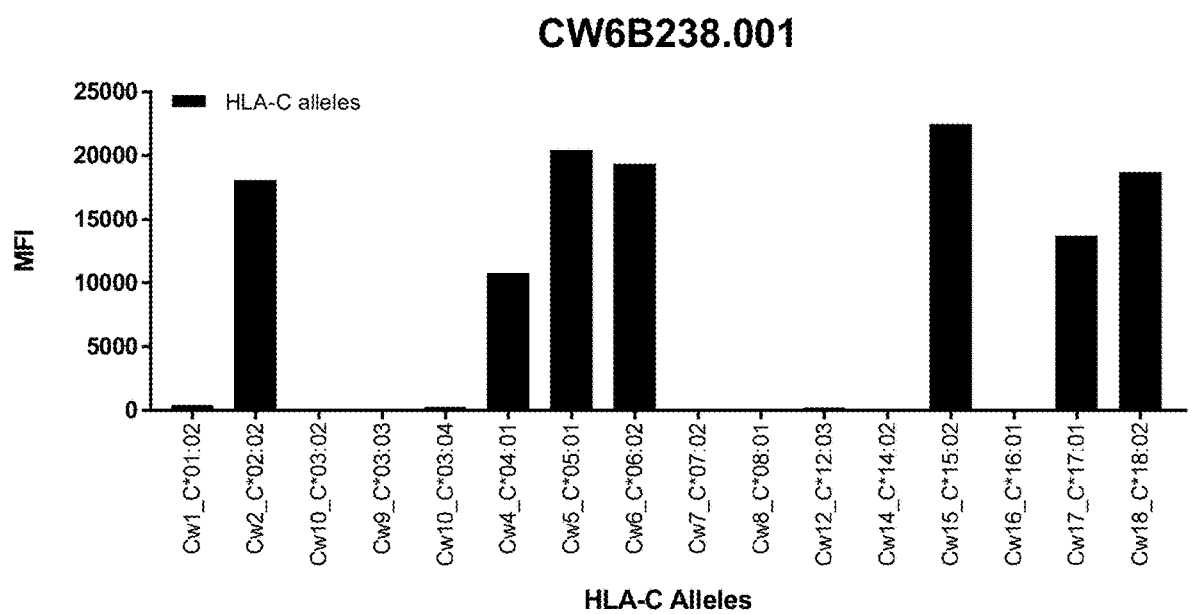
Figure 11A:
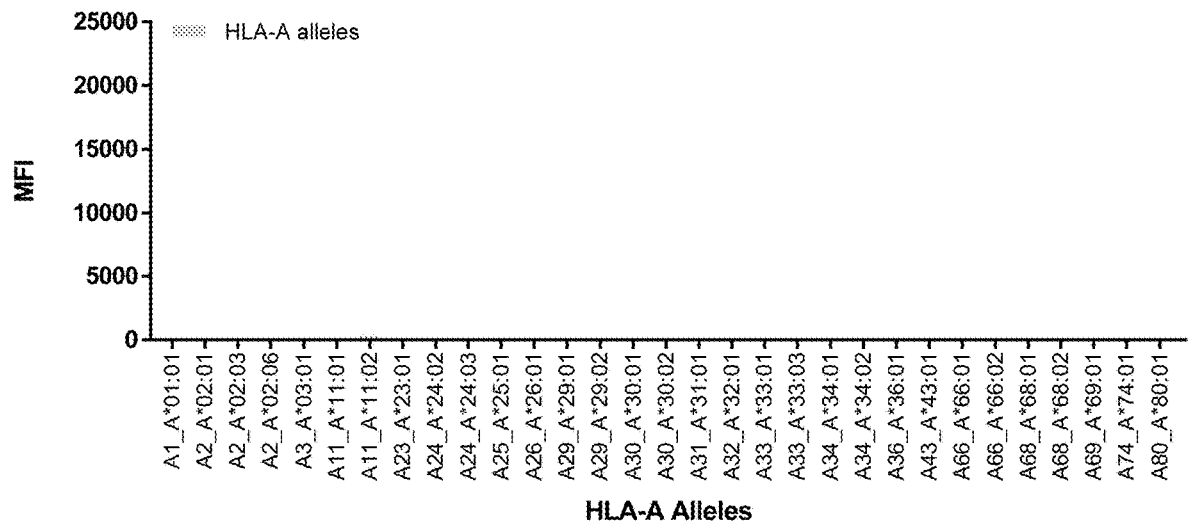
FIGS. 11A-11C show graphs demonstrating LabScreen Class I MHC allele binding profiles for the CW6B188.001 Anti-HLA-C antibody.
Figure 11B:
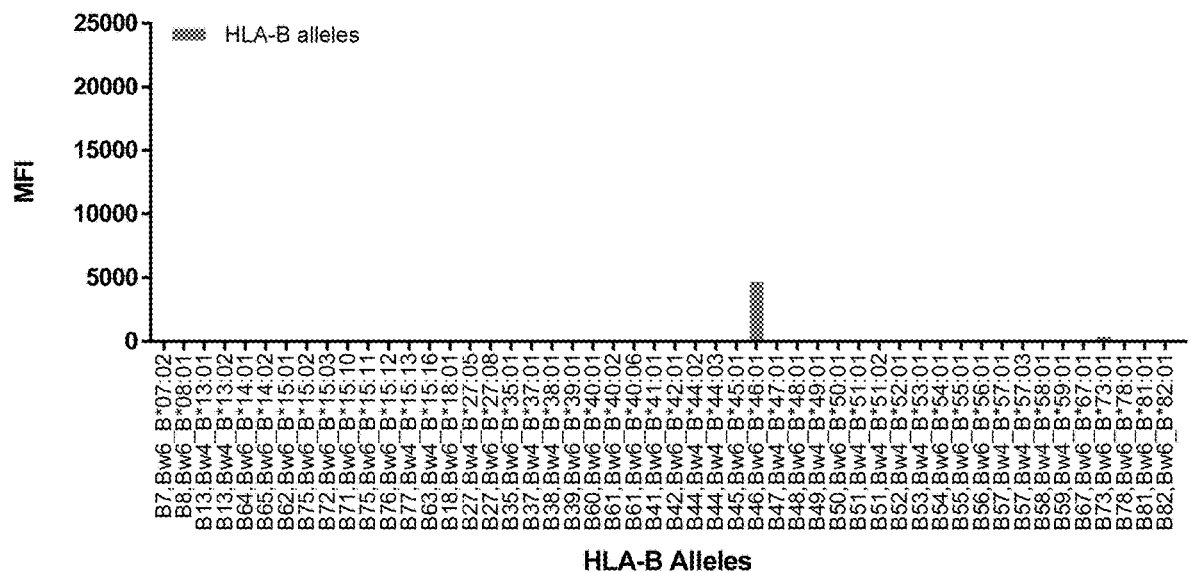
Figure 11C:
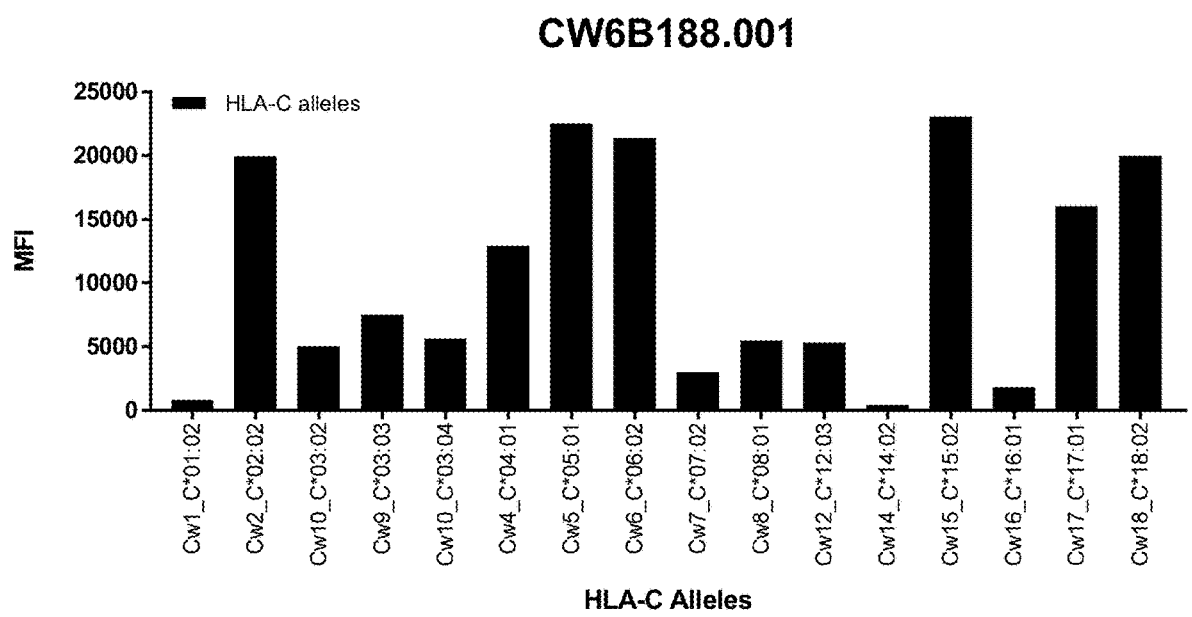
Figure 12A:
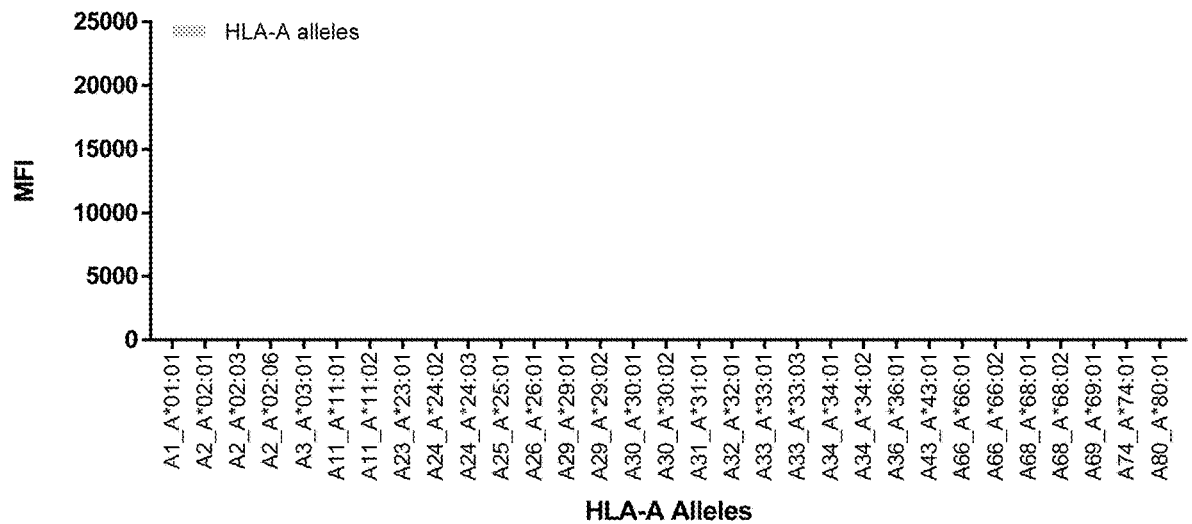
FIGS. 12A-12C show graphs demonstrating LabScreen Class I MHC allele binding profiles for the CW6B123.001 Anti-HLA-C antibody.
Figure 12B:
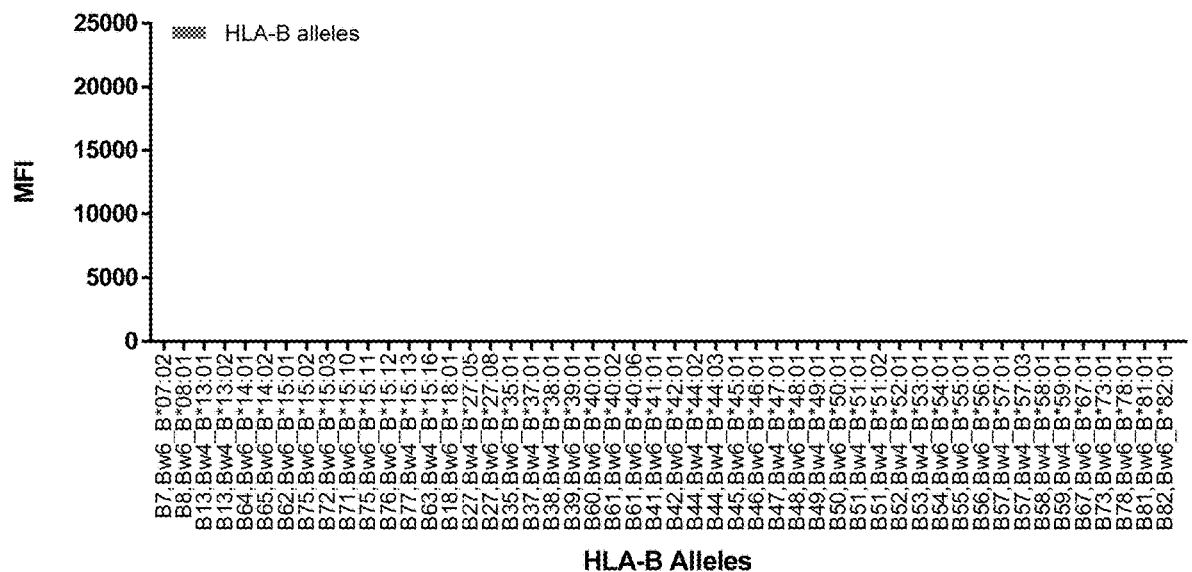
Figure 12C:
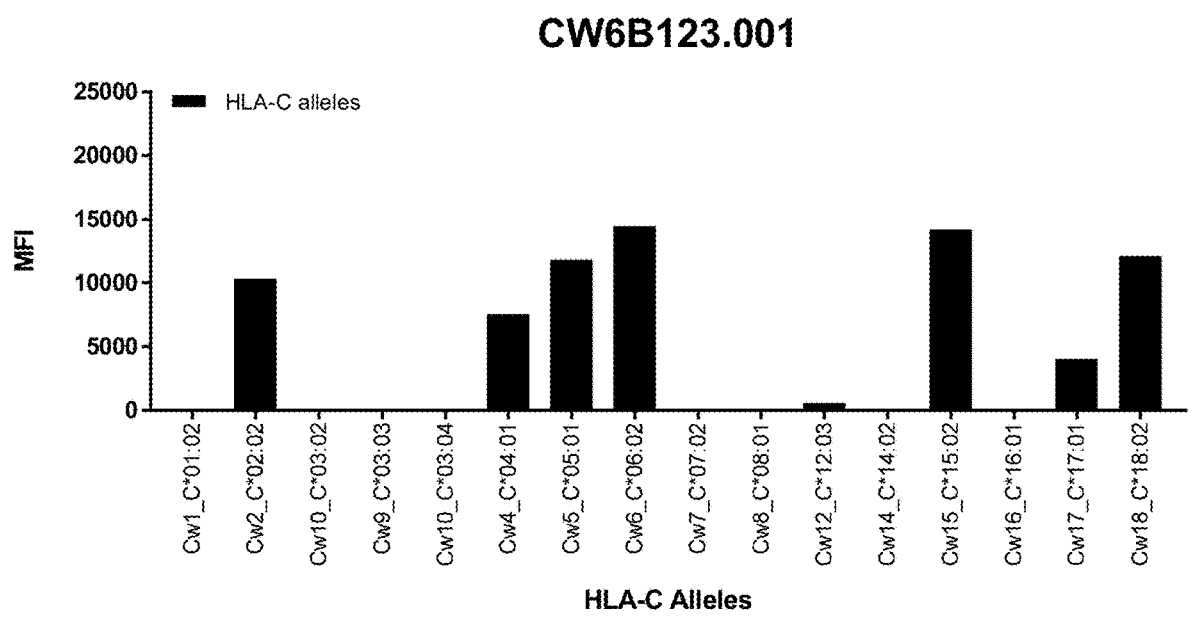
Figure 13A:
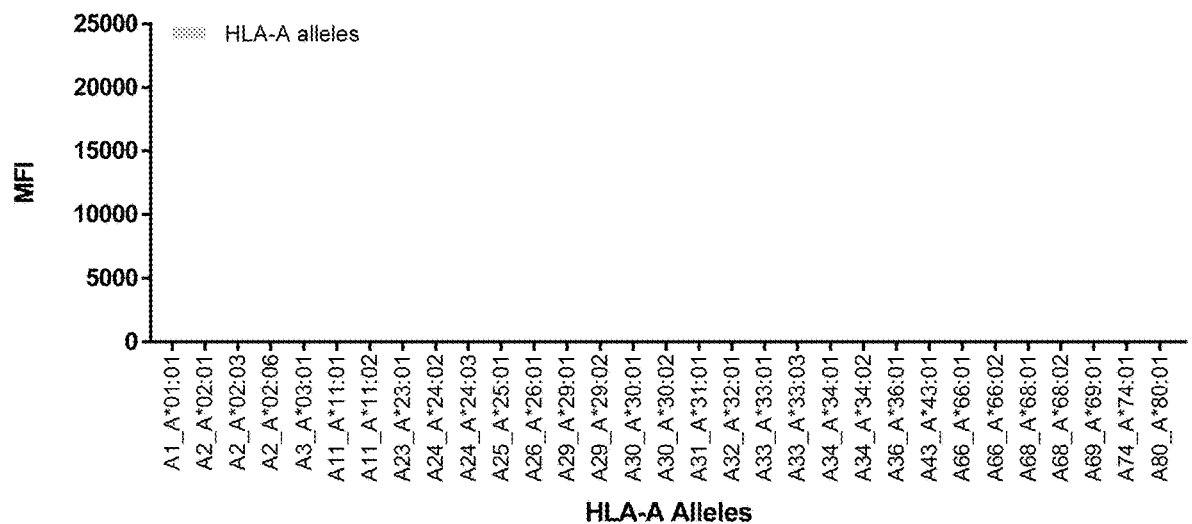
FIGS. 13A-13C show graphs demonstrating LabScreen Class I MHC allele binding profiles for the control CNTO9412 (huIgG4_PAA isotype) antibody.
Figure 13B:
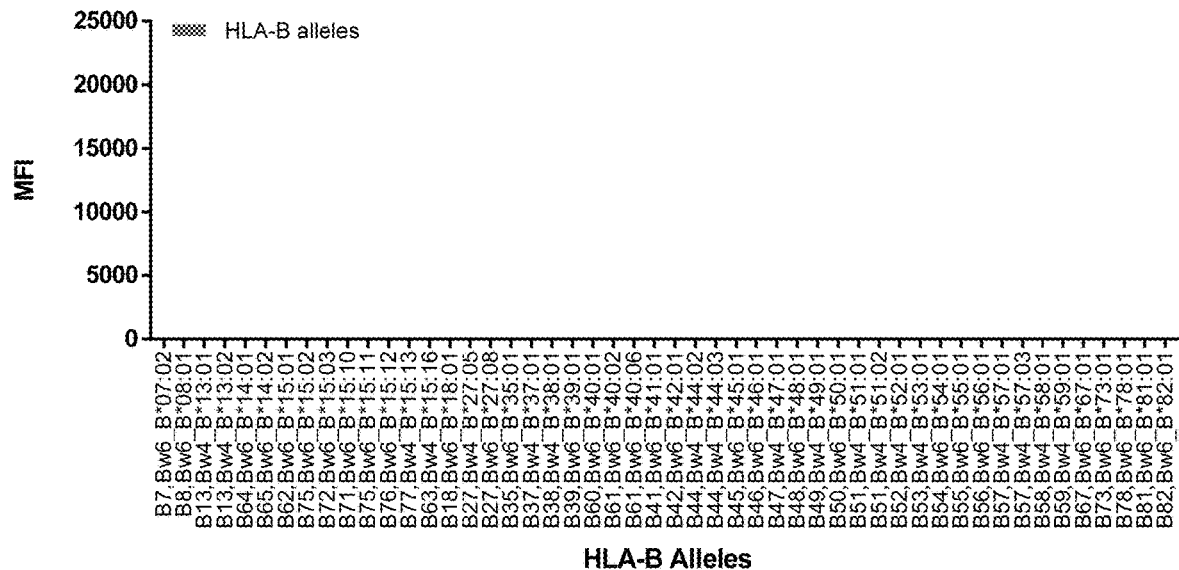
Figure 13C:
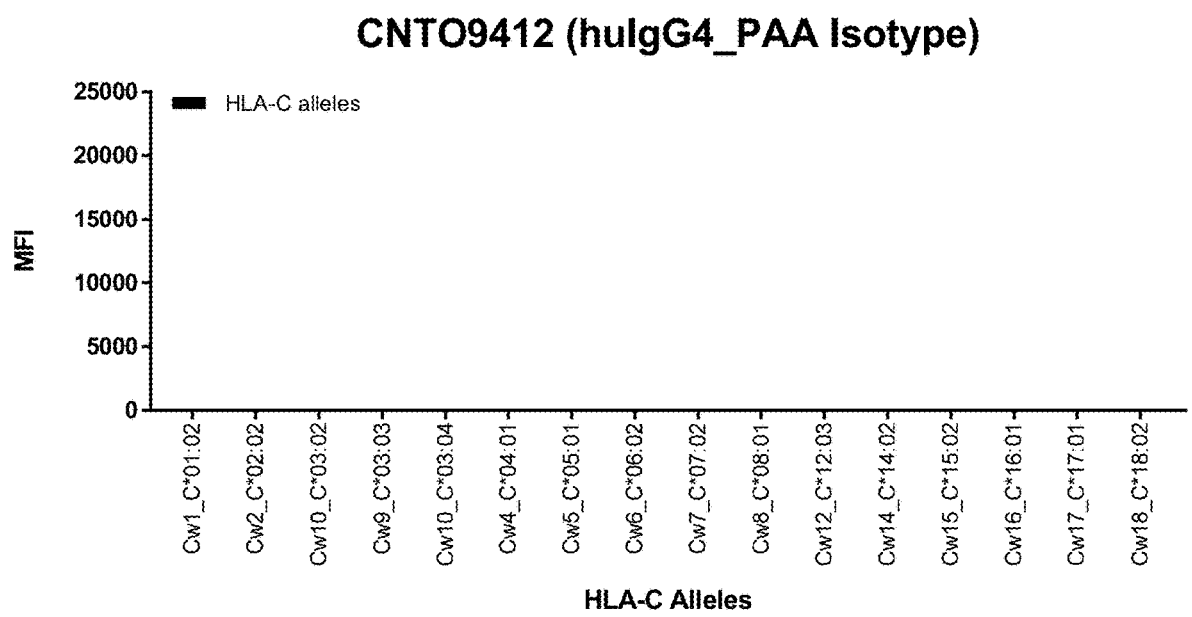

The seven antibodies with good efficacy in blocking IL-2 release were characterized in an orthogonal functional bioassay that measured the inhibition of HLA-Cw6/ADAM-Abu and HLA-Cw6/TRAT dependent Jurkat T cell activation as measured by CD69 upregulation. Briefly, K562 cells stably expressing rHLA-Cw6 were loaded with ADAM-abu, or TRAT, peptide, treated with anti-HLA-Cw6 antibodies, and co-cultured with Jurkat T cell lines stably expressing TCR-ADAMTLS5, or TCR-TRAT, respectively. After an overnight incubation, the HLA-Cw6/peptide dependent up-regulation of CD69 expression was monitored by flow cytometry. All seven antagonist antibodies from the IL-2 inhibition assay show antibody concentration dependent blocking of CD69 up-regulation on Jurkat-TCR-ADAMTSL5 (FIG. 1) and Jurkat-TCR-TRAT (FIG. 2) T cell lines. Against HLA-Cw6/ADAM-Abu, CW6B130 showed highest potency and CW6B237 the lowest potency. Against HLA-Cw6/TRAT, Cw6B237 has the highest potency.

LABSCREEN® Allele Specificity Screen

Purified antibodies were analyzed for allelic specificity by the LABSCREEN® assay, which evaluates qualitative antibody binding to 97 Class I HLA alleles (HLA-A, -B and -C) using bead-based fluorescent flow technology (Luminex 100). The data was analyzed using HLA Fusion™ software (version 4.0) and antibodies with high selectivity to HLA-C alleles were selected for further evaluation by their functional activity, binding and other characteristics. Of the in-house generated antibodies, CW6B237 and CW6B238 show the highest specificity to HLA-C alleles, followed by CW6B130, CW6B175 and CW6B188 which all have cross-reactivity to HLA-B46, and CW6B130 and CW6B175 showing additional cross-reactivity to HLA-B73. Sequence analysis of these HLA-I alleles show HLA-B73 is closely related to the HLA-C family, while HLA-B46 appears to be contained within the HLA-B family. There is a valine at position 76 that is conserved in HLA-C, HLA-B46 and HLA-B73 alleles but not in other HLA-B alleles, suggesting a role of this valine in the allelic specificity observed with these antibodies. The remainder of the antibodies show cross-reactivity (qualitatively) to at least >10 non-HLA-C alleles, with CW6B238 having the highest cross-reactivity across the 97 class I MHC alleles tested (FIGS. 3A-3C, 4A-4C, 5A-5C, 6A-6C, 7A-7C, 8A-8C, 9A-9C, 10A-10C, 11A-11C, 12A-12C, and 13A-13C).

The antibodies with highest specificity to HLA-C alleles (CW6B237 and CW6B238) show good antagonist efficacy but not the highest activity. The highest antagonist efficacy belongs to CW6B130 and CW6B175, which shows, qualitatively, cross-reactivity to HLA-B46 and HLA-B73. CW6B188, which has high HLA-C selectivity but binds HLA-B46 has no antagonist activity in the T cell activation studies.

Affinity Measurements (SPR)

Affinity measurements of anti-HLA-Cw6 antibodies were obtained by Surface Plasmon Resonance (SPR) methods using a ProteON XPR36 system, as already described, against rHLA-Cw6/ARFN (SEQ ID NO:205) (acidic peptide in refolded rHLA-Cw6, aka CW6W3.ECO.PP.002/.003) (SEQ ID NO:203), rHLA-Cw6/TRAT (basic peptide in single-chain expressed protein, aka CW6W32) (SEQ ID NO:202) and rHLA-Cw6/ADAMTSL5 (acidic peptide in single-chain expressed protein, aka CW6W36) (SEQ ID NO:204) antigens. The antibodies showed differential binding kinetics to the three antigens tested (Table 9).

TABLE 9

Binding affinities of anti-HLA-Cw6 antibodies to HLA-Cw6/peptide antigens
Antigen-CW6W3.ECO.PP.002/.003. (rhHLA-Cw6/ARFN)

| mAB ID | Source | ka (1/Ms) | kd (1/s) | KD (nM) | Comments |
| --- | --- | --- | --- | --- | --- |
| CW6B130 | OMT | n/a | n/a | n/a | Binding confirmed, fit not valid |
| CW6B175 | OMT | 1.05-1.10E+07 | 3.14-3.63E−04 | 0.0285-0.0346 | Valid kinetic fit. Range of two replicates. |
| CW6B228 | Ablexis | 4.89E+06 | 1.78E−04 | 0.04 | Valid kinetic fit |
| CW6B229 | Ablexis | 1.22-1.31E+06 | 2.84-3.42E−04 | 0.217-0.281 | Valid kinetic fit. Range of two replicates. |
| CW6B230 | Ablexis | 1.74E+06 | 2.21E−04 | 0.13 | Valid kinetic fit |
| CW6B233 | Ablexis | 1.02E+06 | 2.93E−04 | 0.29 | Valid kinetic fit |
| CW6B237 | Ablexis | 6.68-7.41E+05 | <=5.70E−05 | <=0.08 | Valid kinetic fit. Range of two replicates. |
| CW6B238 | Ablexis | 1.06E+06 | <=5.70E−05 | <=0.05 | Valid kinetic fit |
| CW6B188 | OMT | 5.66E+06 | 5.74E−04 | 0.12 | Valid kinetic fit. |
| CW6B123 | Pos Ctrl | n/a | n/a | n/a | No/low binding response |

Antigen-CW6W32 (rhHLA-Cw6/TRAT)

| AA ID | Source | ka (1/Ms) | kd (1/s) | KD (nM) | Comments |
| --- | --- | --- | --- | --- | --- |
| CW6B130 | OMT | 1.03E+07 | 2.72E−03 | 0.27 | Valid kinetic fit |
| CW6B175 | OMT | n/a | n/a | n/a | Binding confirmed, fit not valid |
| CW6B228 | Ablexis | 5.98E+06 | 5.34E−04 | 0.09 | Valid kinetic fit |
| CW6B229 | Ablexis | 1.67-1.75E+06 | 1.25-1.90E−03 | 0.713-1.14 | Valid kinetic fit. Range of two replicates. |
| CW6B230 | Ablexis | 1.15E+06 | 1.45E−03 | 1.26 | Valid kinetic fit |
| CW6B233 | Ablexis | 1.51E+06 | 2.34E−03 | 1.55 | Valid kinetic fit |
| CW6B237 | Ablexis | n/a | n/a | n/a | Binding confirmed, fit not valid |
| CW6B238 | Ablexis | n/a | n/a | n/a | No/low binding response |
| CW6B188 | OMT | n/a | n/a | n/a | Binding confirmed, fit not valid. |
| CW6B123 | Pos Ctrl | 2.88E+06 | 1.44E−03 | 9.66E−01 | Valid kinetic fit. mean of 8 replicates |

TABLE 9-continued

Binding affinities of anti-HLA-Cw6 antibodies
to HLA-Cw6/peptide antigens
Antigen-CW6W3.ECO.PP.002/.003. (rhHLA-Cw6/ARFN)

| mAB ID | Source | ka (1/Ms) | kd (1/s) | KD (nM) | Comments |
|---|---|---|---|---|---|

Antigen-CW6W36 (rhHLA-Cw6/ADAMTSL5)

| AA ID | Source | ka (1/Ms) | kd (1/s) | KD (nM) | Comments |
|---|---|---|---|---|---|
| CW6B130 | OMT | 1.66-1.75E +07 | 1.24-0.970E−03 | 0.0586-0.0713 | Valid kinetic fit. Range of two replicates. |
| CW6B175 | OMT | n/a | n/a | n/a | Binding confirmed, fit not valid |
| CW6B228 | Ablexis | 1.52E+07 | 7.32E−04 | 0.05 | Valid kinetic fit |
| CW6B229 | Ablexis | 3.75E+06 | 3.36E−03 | 0.90 | Valid kinetic fit |
| CW6B230 | Ablexis | 3.05E+06 | 1.66E−03 | 0.55 | Valid kinetic fit |
| CW6B233 | Ablexis | 3.56E+06 | 3.55E−03 | 1.00 | Valid kinetic fit |
| CW6B237 | Ablexis | n/a | n/a | n/a | No/low binding response |
| CW6B238 | Ablexis | n/a | n/a | n/a | No/low binding response |
| CW6B188 | OMT | n/a | n/a | n/a | Binding confirmed, fit not valid |
| CW6B123 | Pos Ctrl | 1.42E+07 | 1.58E−02 | 1.10E+00 | Valid kinetic fit. Mean of 8 replicates |

To further characterize the ability of the antibodies to differentiate between class I MHC molecules. SPR was performed on a Biacore 8K instrument with the seven antagonist antibodies against 11 antigens representing HLA-C*06:02, HLA-B*46:01 and HLA-B*73:01 class I MHC molecules loaded with peptides that represent peptides observed associated with these class I MHC alleles with high frequency (Hilton et al., 2017, Cell Reports 19:1394-1405, Barber et al., 1996, Tissue Antigens. 47:472-7).

While the LABScreen assay results indicate CW6B130 and CW6B175 have cross-reactivity to HLA-B*46:01 and HLA-B*73:01 alleles, the SPR data using antigens with cognate peptides show that these antibodies bind poorly to the peptide loaded antigens (Table 10).

TABLE 10

Binding affinities of anti-HLA-Cw6 antibodies to 11 class
I MHC HLA-C*06:02, HLA-B*46:01, and HLA-B*73:01
molecules with different peptide classes

CW6B130

| ANTIGEN | ka (1/Ms) | kd (1/s) | KD (nM) | Kinetic Fit |
|---|---|---|---|---|
| CW6W32.009 | 8.20E+06 | 5.09E−03 | 6.22E−10 | Kinetic fit not valid |
| CW6W35.001 | 1.67E+06 | 1.01E−02 | 6.04E−09 | Kinetic fit not valid |
| CW6W36.002 | 6.77E+06 | 1.84E−03 | 2.72E−10 | Acceptable fit |
| CW6W47.001 | No/low binding | No/low binding | No/low binding | Acceptable fit |
| CW6W51.001 | 6.81E+05 | 3.89E−04 | 5.71E−10 | Kinetic fit not valid |
| CW6W53.001 | 2.63E+07 | 5.40E−03 | 2.05E−10 | Kinetic fit not valid |
| CW6W54.001 | 2.47E+07 | 2.04E−03 | 8.28E−11 | Kinetic fit not valid |
| CW6W55.ECO.PP.001 | No/low binding | No/low binding | No/low binding | Kinetic fit not valid |
| CW6W55.ECO.PP.002 | No/low binding | No/low binding | No/low binding | Acceptable fit |
| CW6W55.ECO.PP.003 | No/low binding | No/low binding | No/low binding | Kinetic fit not valid |
| CW6W56.ECO.PP.001 | No/low binding | No/low binding | No/low binding | Acceptable fit |

CW6B175

| ANTIGEN | ka (1/Ms) | kd (1/s) | KD (nM) | Kinetic Fit |
|---|---|---|---|---|
| CW6W32.009 | 4.28E+08 | 2.84E−01 | 6.63E−10 | Kinetic fit not valid |
| CW6W35.001 | 1.05E+06 | 1.26E−04 | 1.20E−10 | Acceptable fit |
| CW6W36.002 | 8.73E+06 | 1.63E−02 | 1.87E−09 | Acceptable fit |
| CW6W47.001 | No/low binding | No/low binding | No/low binding | Acceptable fit |
| CW6W51.001 | 1.82E+06 | 2.85E−04 | 1.57E−10 | Acceptable fit |
| CW6W53.001 | 1.72E+06 | 5.60E−04 | 3.27E−10 | Acceptable fit |
| CW6W54.001 | 6.60E+06 | 8.42E−04 | 1.28E−10 | Acceptable fit |
| CW6W55.ECO.PP.001 | No/low binding | No/low binding | No/low binding | Kinetic fit not valid |
| CW6W55.ECO.PP.002 | No/low binding | No/low binding | No/low binding | Kinetic fit not valid |
| CW6W55.ECO.PP.003 | No/low binding | No/low binding | No/low binding | Kinetic fit not valid |
| CW6W56.ECO.PP.001 | No/low binding | No/low binding | No/low binding | Kinetic fit not valid |

CW6B229

| ANTIGEN | ka (1/Ms) | kd (1/s) | KD (nM) | Kinetic Fit |
|---|---|---|---|---|
| CW6W32.009 | 5.34E+05 | 1.81E−03 | 3.40E−09 | Acceptable fit |
| CW6W35.001 | 2.37E+05 | 1.05E−03 | 4.42E−09 | Acceptable fit |

TABLE 10-continued

Binding affinities of anti-HLA-Cw6 antibodies to 11 class I MHC HLA-C*06:02, HLA-B*46:01, and HLA-B*73:01 molecules with different peptide classes

CW6B130

| ANTIGEN | ka (1/Ms) | kd (1/s) | KD (nM) | Kinetic Fit |
|---|---|---|---|---|
| CW6W36.002 | 1.40E+06 | 5.43E−03 | 3.86E−09 | Acceptable fit |
| CW6W47.001 | 6.94E+05 | 6.42E−03 | 9.26E−09 | Acceptable fit |
| CW6W51.001 | 4.51E+05 | 5.43E−04 | 1.20E−09 | Acceptable fit |
| CW6W53.001 | 3.91E+05 | 7.52E−04 | 1.92E−09 | Acceptable fit |
| CW6W54.001 | 6.91E+05 | 4.65E−04 | 6.73E−10 | Kinetic fit not valid |
| CW6W55.ECO.PP.001 | No/ low binding | No/ low binding | No/ low binding | Kinetic fit not valid |
| CW6W55.ECO.PP.002 | 3.08E+09 | 2.19E+01 | 7.10E−09 | Kinetic fit not valid |
| CW6W55.ECO.PP.003 | No/ low binding | No/ low binding | No/ low binding | Kinetic fit not valid |
| CW6W56.ECO.PP.001 | 1.03E+06 | 1.27E−03 | 1.23E−09 | Acceptable fit |

CW6B230

| ANTIGEN | ka (1/Ms) | kd (1/s) | KD (nM) | Kinetic Fit |
|---|---|---|---|---|
| CW6W32.009 | 3.58E+05 | 1.48E−03 | 4.13E−09 | Acceptable fit |
| CW6W35.001 | 2.30E+05 | 5.08E−04 | 2.21E−09 | Acceptable fit |
| CW6W36.002 | 8.32E+05 | 2.20E−03 | 2.64E−09 | Acceptable fit |
| CW6W47.001 | 3.28E+05 | 3.96E−03 | 1.21E−08 | Acceptable fit |
| CW6W51.001 | 3.68E+05 | 4.47E−04 | 1.21E−09 | Acceptable fit |
| CW6W53.001 | 2.94E+05 | 5.80E−04 | 1.97E−09 | Acceptable fit |
| CW6W54.001 | 4.67E+05 | 6.55E−04 | 1.40E−09 | Kinetic fit not valid |
| CW6W55.ECO.PP.001 | No/ low binding | No/ low binding | No/ low binding | Kinetic fit not valid |
| CW6W55.ECO.PP.002 | 7.37E+05 | 6.55E−03 | 8.90E−09 | Acceptable fit |
| CW6W55.ECO.PP.003 | No/ low binding | No/ low binding | No/ low binding | Acceptable fit |
| CW6W56.ECO.PP.001 | 1.42E+06 | 2.95E−03 | 2.07E−09 | Acceptable fit |

CW6B233

| ANTIGEN | ka (1/Ms) | kd (1/s) | KD (nM) | Kinetic Fit |
|---|---|---|---|---|
| CW6W32.009 | 5.44E+05 | 2.03E−03 | 3.73E−09 | Kinetic fit not valid |
| CW6W35.001 | 2.11E+05 | 7.58E−04 | 3.59E−09 | Acceptable fit |
| CW6W36.002 | 1.14E+06 | 4.33E−03 | 3.82E−09 | Acceptable fit |
| CW6W47.001 | 8.32E+05 | 8.01E−03 | 9.63E−09 | Acceptable fit |
| CW6W51.001 | 4.37E+05 | 5.14E−04 | 1.18E−09 | Acceptable fit |
| CW6W53.001 | 3.50E+05 | 7.30E−04 | 2.09E−09 | Acceptable fit |
| CW6W54.001 | 6.07E+05 | 4.84E−04 | 7.98E−10 | Kinetic fit not valid |
| CW6W55.ECO.PP.001 | No/ low binding | No/ low binding | No/ low binding | Kinetic fit not valid |
| CW6W55.ECO.PP.002 | 1.67E+08 | 1.22E+00 | 7.30E−09 | Kinetic fit not valid |
| CW6W55.ECO.PP.003 | No/ low binding | No/ low binding | No/ low binding | Kinetic fit not valid |
| CW6W56.ECO.PP.001 | 8.49E+05 | 1.07E−03 | 1.26E−09 | Acceptable fit |

CW6B237

| ANTIGEN | ka (1/Ms) | kd (1/s) | KD (nM) | Kinetic Fit |
|---|---|---|---|---|
| CW6W32.009 | No/ low binding | No/ low binding | No/ low binding | Acceptable fit |
| CW6W35.001 | 7.57E+04 | 2.51E−03 | 3.31E−08 | Kinetic fit not valid |
| CW6W36.002 | No/ low binding | No/ low binding | No/ low binding | Acceptable fit |
| CW6W47.001 | No/ low binding | No/ low binding | No/ low binding | Acceptable fit |
| CW6W51.001 | No/ low binding | No/ low binding | No/ low binding | Acceptable fit |
| CW6W53.001 | No/ low binding | No/ low binding | No/ low binding | Acceptable fit |
| CW6W54.001 | No/ low binding | No/ low binding | No/ low binding | Kinetic fit not valid |
| CW6W55.ECO.PP.001 | No/ low binding | No/ low binding | No/ low binding | Kinetic fit not valid |
| CW6W55.ECO.PP.002 | No/ low binding | No/ low binding | No/ low binding | Kinetic fit not valid |
| CW6W55.ECO.PP.003 | No/ low binding | No/ low binding | No/ low binding | Kinetic fit not valid |
| CW6W56.ECO.PP.001 | No/ low binding | No/ low binding | No/ low binding | Kinetic fit not valid |

CW6B238

| ANTIGEN | ka (1/Ms) | kd (1/s) | KD (nM) | Kinetic Fit |
|---|---|---|---|---|
| CW6W32.009 | No/ low binding | No/ low binding | No/ low binding | Acceptable fit |
| CW6W35.001 | 8.94E+08 | 9.87E+00 | 1.10E−08 | Acceptable fit |
| CW6W36.002 | No/ low binding | No/ low binding | No/ low binding | Kinetic fit not valid |
| CW6W47.001 | No/ low binding | No/ low binding | No/ low binding | Acceptable fit |
| CW6W51.001 | No/ low binding | No/ low binding | No/ low binding | Acceptable fit |
| CW6W53.001 | No/ low binding | No/ low binding | No/ low binding | Acceptable fit |
| CW6W54.001 | No/ low binding | No/ low binding | No/ low binding | Acceptable fit |
| CW6W55.ECO.PP.001 | No/ low binding | No/ low binding | No/ low binding | Kinetic fit not valid |
| CW6W55.ECO.PP.002 | No/ low binding | No/ low binding | No/ low binding | Kinetic fit not valid |
| CW6W55.ECO.PP.003 | No/ low binding | No/ low binding | No/ low binding | Kinetic fit not valid |
| CW6W56.ECO.PP.001 | No/ low binding | No/ low binding | No/ low binding | Kinetic fit not valid |

Epitope Binning and Mapping (IBIS and HDX)

Anti-HLA-Cw6 epitopes on target antigen (CW6W3.ECO.PP.002/.003 (rhHLA-Cw6 (SEQ ID NO:203)/ARF (SEQ ID NO:219)) was determined by classical competition (sandwich format) experiment using SPRi (SPR imaging) and CFM (continuous flow microfluidic, or microspotter) printing and analyzed using the IBIS method. There were 6 total bin groups identified using a panel of 94 anti-HLA-C antibodies, and the 9 identified antibodies fit into three distinct epitope groups. Four of them bin together with the positive/reference control antibody, CW6B 123, in Group 3; four bin together in Group 4 and one antibody, CW6B237, bins into Group 6 (Table 11)

TABLE 11

Binning groups for the anti-HLA-Cw6 antibodies

| Group 1 | Group 2 | Group 3 | Group 4 | Group 5 | Group 6 |
|---|---|---|---|---|---|
|  |  | CW6B130 | CW6B228 |  | CW6B237 |
|  |  | CW6B175 | CW6B229 |  |  |
|  |  | CW6B188 | CW6B233 |  |  |
|  |  | CW6B238 |  |  |  |
| 0 | 0 | 4 | 3 | 0 | 1 |

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

The invention claimed is:

1. An isolated monoclonal antibody or antigen-binding fragment thereof comprising a heavy chain variable region and a light chain variable region, the heavy chain variable region comprising a heavy chain complementarity determining region 1 (HCDR1), HCDR2, and a HCDR3, the light chain variable region comprising a light chain complementarity determining region 1 (LCDR1), LCDR2, and LCDR3, wherein the HCDR1, HCDR2, HCDR3, LCDR1, LCDR2 and LCDR3 comprise the amino acid sequences of:
   a. SEQ ID NOs: 37, 38, 39, 64, 65, and 66, respectively;
   b. SEQ ID NOs: 40, 41, 42, 67, 68, and 69, respectively;
   c. SEQ ID NOs: 43, 44, 45, 70, 71, and 72, respectively;
   d. SEQ ID NOs: 46, 47, 48, 73, 74, and 75, respectively;
   e. SEQ ID NOs: 49, 50, 51, 76, 77, and 78, respectively;
   f. SEQ ID NOs: 52, 53, 54, 79, 80, and 81, respectively;
   g. SEQ ID NOs: 55, 56, 57, 82, 83, and 84, respectively;
   h. SEQ ID NOs: 58, 59, 60, 85, 86, and 87, respectively; or
   i. SEQ ID NOs: 61, 62, 63, 88, 89, and 90, respectively; wherein the antibody or antigen-binding fragment thereof binds HLA-C.

2. An isolated monoclonal antibody or antigen-binding fragment thereof comprising a heavy chain variable region and a light chain variable region, the heavy chain variable region comprising a heavy chain complementarity determining region 1 (HCDR1), HCDR2, and a HCDR3, the light chain variable region comprising a light chain complementarity determining region 1 (LCDR1), LCDR2, and LCDR3, wherein the HCDR1, HCDR2, HCDR3, LCDR1, LCDR2 and LCDR3 comprise the amino acid sequences of:
  a. SEQ ID NOs: 91, 92, 93, 118, 119, and 120, respectively;
  b. SEQ ID NOs: 94, 95, 96, 121, 122, and 123, respectively;
  c. SEQ ID NOs: 97, 98, 99, 124, 125, and 126, respectively;
  d. SEQ ID NOs: 100, 101, 102, 127, 128, and 129, respectively;
  e. SEQ ID NOs: 103, 104, 105, 130, 131, and 132, respectively;
  f. SEQ ID NOs: 106, 107, 108, 133, 134, and 135, respectively;
  g. SEQ ID NOs: 109, 110, 111, 136, 137, and 138, respectively;
  h. SEQ ID NOs: 112, 113, 114, 139, 140, and 141, respectively; or
  i. SEQ ID NOs: 115, 116, 117, 142, 143, and 144, respectively;
wherein the antibody or antigen-binding fragment thereof specifically binds HLA-Cw6.

3. An isolated monoclonal antibody or antigen-binding fragment thereof comprising a heavy chain variable region and a light chain variable region, the heavy chain variable region comprising a heavy chain complementarity determining region 1 (HCDR1), HCDR2, and a HCDR3, the light chain variable region comprising a light chain complementarity determining region 1 (LCDR1), LCDR2, and LCDR3, wherein the HCDR1, HCDR2, HCDR3, LCDR1, LCDR2 and LCDR3 comprise the amino acid sequences of:
  a. SEQ ID NOs: 145, 146, 147, 172, 173, and 174, respectively;
  b. SEQ ID NOs: 148, 149, 150, 175, 176, and 177, respectively;
  c. SEQ ID NOs: 151, 152, 153, 178, 179, and 180, respectively;
  d. SEQ ID NOs: 154, 155, 156, 181, 182, and 183, respectively;
  e. SEQ ID NOs: 157, 158, 159, 184, 185, and 186, respectively;
  f. SEQ ID NOs: 160, 161, 162, 187, 188, and 189, respectively;
  g. SEQ ID NOs: 163, 164, 165, 190, 191, and 192, respectively;
  h. SEQ ID NOs: 166, 167, 168, 193, 194, and 195, respectively; or
  i. SEQ ID NOs: 169, 170, 171, 196, 197, and 198, respectively;
wherein the antibody or antigen-binding fragment thereof binds HLA-C.

4. The isolated monoclonal antibody or antigen-binding fragment thereof of claim 1, wherein the antibody or antigen-binding fragment comprises (i) the heavy and light chain CDRs as set forth in subsection a., and wherein either the heavy chain variable region is at least 95% identical to SEQ ID NO:1, the light chain variable region is at least 95% identical to SEQ ID NO:2, or both;
  (ii) the heavy and light chain CDRs as set forth in subsection b., and wherein either the heavy chain variable region is at least 95% identical to SEQ ID NO:3, the light chain variable region is at least 95% identical to SEQ ID NO:4, or both;
  (iii) the heavy and light chain CDRs as set forth in subsection c., and wherein either the heavy chain variable region is at least 95% identical to SEQ ID NO:5, the light chain variable region is at least 95% identical to SEQ ID NO:6, or both;
  (iv) the heavy and light chain CDRs as set forth in subsection d., and wherein either the heavy chain variable region is at least 95% identical to SEQ ID NO:7, the light chain variable region is at least 95% identical to SEO ID NO:8, or both;
  (v) the heavy and light chain CDRs as set forth in subsection e., and wherein either the heavy chain variable region is at least 95% identical to SEQ ID NO:9, the light chain variable region is at least 95% identical to SEO ID NO: 10, or both;
  (vi) the heavy and light chain CDRs as set forth in subsection f., and wherein either the heavy chain variable region is at least 95% identical to SEO ID NO:11, the light chain variable region is at least 95% identical to SEO ID NO: 12, or both;
  (vii) the heavy and light chain CDRs as set forth in subsection g., and wherein either the heavy chain variable region is at least 95% identical to SEO ID NO: 13, the light chain variable region is at least 95% identical to SEQ ID NO: 14, or both;
  (viii) the heavy and light chain CDRs as set forth in subsection h., and wherein either the heavy chain variable region is at least 95% identical to SEO ID NO: 15, the light chain variable region is at least 95% identical to SEO ID NO: 16, or both: or
  (ix) the heavy and light chain CDRs as set forth in subsection i., and wherein either the heavy chain variable region is at least 95% identical to SEQ ID NO: 17, the light chain variable region is at least 95% identical to SEO ID NO:18, or both.

5. The isolated monoclonal antibody or antigen-binding fragment thereof of claim 1, wherein the antibody or antigen-binding fragment thereof is chimeric.

6. The isolated monoclonal antibody or antigen-binding fragment thereof of claim 1, wherein the antibody or antigen-binding fragment thereof is humanized.

7. The isolated monoclonal antibody or antigen-binding fragment thereof of claim 1, wherein the antibody or antigen-binding fragment thereof blocks development and activation of T cells, through binding and inhibition of antigen presentation by HLA-Cw6.

8. An isolated nucleic acid encoding the monoclonal antibody or antigen-binding fragment thereof of claim 1.

9. A vector comprising the isolated nucleic acid of claim 8.

10. A host cell comprising the vector of claim 9.

11. A pharmaceutical composition, comprising the isolated monoclonal antibody or antigen-binding fragment thereof of claim 1 and a pharmaceutically acceptable carrier.

12. A method of treating or preventing an autoimmune disease selected from the group consisting of psoriasis, plaque psoriasis, guttate psoriasis, and psoriatic arthritis in a subject in need thereof, comprising administering to the subject the pharmaceutical composition of claim 11.

13. A method of producing the monoclonal antibody or antigen-binding fragment thereof of claim 1, comprising culturing a cell comprising a nucleic acid encoding the monoclonal antibody or antigen-binding fragment thereof under conditions to produce the monoclonal antibody or antigen-binding fragment thereof, and recovering the antibody or antigen-binding fragment thereof from the cell or culture.

14. A method of producing a pharmaceutical composition comprising the monoclonal antibody or antigen-binding fragment of claim 1, comprising combining the monoclonal antibody or antigen-binding fragment thereof with a pharmaceutically acceptable carrier to obtain the pharmaceutical composition.

* * * * *

SEQUENCE LISTING

<160> NUMBER OF SEQ ID NOS: 226

<210> SEQ ID NO 1
<211> LENGTH: 123
<212> TYPE: PRT
<213> ORGANISM: Artificial Sequence
<220> FEATURE:
<223> OTHER INFORMATION: CW6B130 Heavy Chain Variable Region

<400> SEQUENCE: 1

Gln Leu Gln Leu Gln Glu Ser Gly Pro Gly Leu Val Lys Pro Ser Glu
1               5                   10                  15

Thr Leu Ser Leu Thr Cys Thr Val Ser Gly Ala Ser Ile Ser Ser Ile
            20                  25                  30

Asn Tyr Tyr Trp Gly Trp Ile Arg Gln Pro Pro Gly Lys Gly Leu Glu
        35                  40                  45

Trp Ile Gly Ser Phe Tyr Tyr Ser Gly Asn Thr Tyr Tyr Asn Pro Ser
    50                  55                  60

Leu Lys Ser Arg Val Thr Ile Ser Val Asp Thr Ser Lys Asn Tyr Phe
65                  70                  75                  80

Ser Leu Lys Leu Asn Ser Val Thr Ala Ala Asp Thr Ala Val Tyr Tyr
                85                  90                  95

Cys Ala Arg Glu Tyr Tyr Asp Ser Ser Gly Tyr Tyr Pro Phe Glu Pro
            100                 105                 110

Trp Gly Gln Gly Thr Leu Val Thr Val Ser Ser
        115                 120

<210> SEQ ID NO 2
<211> LENGTH: 108
<212> TYPE: PRT
<213> ORGANISM: Artificial Sequence
<220> FEATURE:
<223> OTHER INFORMATION: CW6B130 Light Chain Variable Region

<400> SEQUENCE: 2

Ser Tyr Val Leu Thr Gln Pro Pro Ser Val Ser Val Ala Pro Gly Gln
1               5                   10                  15

Thr Ala Arg Ile Thr Cys Gly Gly Asp Asn Ile Gly Ser Glu Ser Val
            20                  25                  30

His Trp Tyr Gln Gln Lys Pro Gly Gln Ala Pro Val Leu Val Val Tyr
        35                  40                  45

Asp Asp Thr Asp Arg Pro Ser Gly Ile Pro Glu Arg Phe Ser Gly Ser
    50                  55                  60

Lys Ser Gly Thr Thr Ala Thr Leu Thr Ile Ser Trp Val Glu Ala Gly
65                  70                  75                  80

Asp Glu Ala Asp Tyr Tyr Cys Gln Val Trp Asp Ser Ser Asp His
                85                  90                  95

Val Val Phe Gly Gly Gly Thr Lys Leu Thr Val Leu
            100                 105

<210> SEQ ID NO 3
<211> LENGTH: 121
<212> TYPE: PRT
<213> ORGANISM: Artificial Sequence
<220> FEATURE:
<223> OTHER INFORMATION: CW6B175 Heavy Chain Variable Region

<400> SEQUENCE: 3

Glu Val Gln Leu Val Glu Ser Gly Gly Gly Leu Val Gln Pro Gly Gly
1               5                   10                  15

-continued

Ser Leu Arg Leu Ser Cys Ala Ala Ser Gly Phe Thr Phe Thr Asn Tyr
        20                  25                  30

Trp Met Thr Trp Val Arg Gln Ala Pro Gly Lys Gly Leu Glu Trp Val
            35                  40                  45

Ala Asn Ile Lys Gln Ser Gly Ser Glu Lys Tyr Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Thr Leu Tyr Glu Trp Glu Leu Glu Pro Phe Asp Tyr Trp Gly
            100                 105                 110

Gln Gly Thr Leu Val Thr Val Ser Ser
        115                 120

<210> SEQ ID NO 4
<211> LENGTH: 108
<212> TYPE: PRT
<213> ORGANISM: Artificial Sequence
<220> FEATURE:
<223> OTHER INFORMATION: CW6B175 Light Chain Variable Region

<400> SEQUENCE: 4

Ser Tyr Val Leu Thr Gln Pro Pro Ser Val Ser Val Ala Pro Gly Gln
1               5                   10                  15

Thr Ala Arg Ile Thr Cys Gly Gly Asn Arg Ile Gly Ser Lys Ser Val
            20                  25                  30

His Trp Tyr Gln Gln Lys Pro Gly Gln Ala Pro Val Leu Val Val Phe
        35                  40                  45

Asp Asp Ser Asp Arg Pro Ser Gly Ile Pro Glu Arg Phe Ser Gly Ser
50                  55                  60

Asn Ser Gly Ile Thr Ala Thr Leu Thr Ile Ser Arg Val Glu Ala Gly
65                  70                  75                  80

Asp Glu Ala Asp Tyr Tyr Cys Gln Val Trp Asp Ser Ser Asn Asp His
                85                  90                  95

Val Val Phe Gly Gly Gly Thr Lys Leu Thr Val Leu
            100                 105

<210> SEQ ID NO 5
<211> LENGTH: 117
<212> TYPE: PRT
<213> ORGANISM: Artificial Sequence
<220> FEATURE:
<223> OTHER INFORMATION: CW6B228 Heavy Chain Variable Region

<400> SEQUENCE: 5

Gln Val Gln Leu Gln Glu Ser Gly Pro Gly Leu Val Lys Pro Ser Glu
1               5                   10                  15

Thr Leu Ser Leu Thr Cys Thr Val Ser Gly Asn Ser Ile Arg Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Ile Ser Gly Asn Thr Asn Tyr Asn Pro Ser Leu Lys
50                  55                  60

Ser Arg Val Thr Met Ser Ile Asp Thr Ser Lys Asn Gln Phe Ser Leu
65                  70                  75                  80

Lys Leu Ser Ser Val Thr Ala Ala Asp Thr Ala Val Tyr Tyr Cys Ala

```
                85                  90                  95
Arg Leu Ser Gly Ile Asp Ala Phe Asp Ile Trp Gly Gln Gly Thr Met
            100                 105                 110

Val Thr Val Ser Ser
        115

<210> SEQ ID NO 6
<211> LENGTH: 107
<212> TYPE: PRT
<213> ORGANISM: Artificial Sequence
<220> FEATURE:
<223> OTHER INFORMATION: CW6B228 Light Chain Variable Region

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Ser Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Gln Gln Tyr Asp Asp Leu Pro Ile
                85                  90                  95

Thr Phe Gly Gln Gly Thr Arg Leu Glu Ile Lys
            100                 105

<210> SEQ ID NO 7
<211> LENGTH: 117
<212> TYPE: PRT
<213> ORGANISM: Artificial Sequence
<220> FEATURE:
<223> OTHER INFORMATION: CW6B229 Heavy Chain Variable Region

<400> SEQUENCE: 7

Gln Val Gln Leu Gln Glu Ser Gly Pro Gly Leu Val Lys Pro Ser Glu
1               5                   10                  15

Thr Leu Ser Leu Thr Cys Thr Val Ser Gly Asn Ser Ile Arg Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Ile Ser Gly Asn Thr Asn Tyr Asn Pro Ser Leu Lys
    50                  55                  60

Ser Arg Val Thr Met Ser Ile Asp Thr Ser Lys Asn Gln Phe Ser Leu
65                  70                  75                  80

Lys Leu Ser Ser Val Thr Ala Ala Asp Thr Ala Val Phe Tyr Cys Ala
                85                  90                  95

Arg Leu Ser Gly Ile Asp Ala Phe Asp Ile Trp Gly Gln Gly Thr Met
            100                 105                 110

Val Thr Val Ser Ser
        115

<210> SEQ ID NO 8
<211> LENGTH: 107
<212> TYPE: PRT
<213> ORGANISM: Artificial Sequence
<220> FEATURE:
```

<223> OTHER INFORMATION: CW6B229 Light Chain Variable Region

<400> SEQUENCE: 8

```
Asp Ile Gln Met Thr Gln Ser Pro Ser Ser Leu Ser Ala Ser Val Gly
1               5                  10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Gln Gln Tyr Asp Asn Leu Pro Ile
                85                  90                  95

Thr Phe Gly Gln Gly Thr Arg Leu Glu Ile Lys
            100                 105
```

<210> SEQ ID NO 9
<211> LENGTH: 117
<212> TYPE: PRT
<213> ORGANISM: Artificial Sequence
<220> FEATURE:
<223> OTHER INFORMATION: CW6B230 Heavy Chain Variable Region

<400> SEQUENCE: 9

```
Gln Val Gln Leu Gln Glu Ser Gly Pro Gly Leu Val Lys Pro Ser Glu
1               5                  10                  15

Thr Leu Ser Leu Thr Cys Thr Val Ser Gly Asn Ser Ile Ser Asn Tyr
            20                  25                  30

Tyr Trp Ser Trp Ile Arg Gln Pro Ala Gly Lys Gly Leu Glu Trp Ile
        35                  40                  45

Gly Arg Ile Tyr Ile Thr Gly Asn Thr Asn Tyr Asn Pro Ser Leu Lys
    50                  55                  60

Ser Arg Val Thr Met Ser Leu Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Leu Ser Gly Ile Asp Ala Phe Asp Ile Trp Gly Gln Gly Thr Met
            100                 105                 110

Val Thr Val Ser Ser
        115
```

<210> SEQ ID NO 10
<211> LENGTH: 107
<212> TYPE: PRT
<213> ORGANISM: Artificial Sequence
<220> FEATURE:
<223> OTHER INFORMATION: CW6B230 Light Chain Variable Region

<400> SEQUENCE: 10

```
Asp Ile Gln Met Thr Gln Ser Pro Ser Thr Leu Ser Ala Ser Val Gly
1               5                  10                  15

Asp Arg Val Thr Phe Thr Cys Gln Ala Ser Gln Asp Ile Thr Lys Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
```

```
                  50                  55                  60
Ser Gly Ser Gly Thr Asp Phe Thr Phe Thr Ile Ser Ser Leu Gln Pro
 65                  70                  75                  80

Glu Asp Phe Ala Thr Tyr Tyr Cys Gln Gln Tyr Asp Asp Leu Pro Ile
                 85                  90                  95

Thr Phe Gly Gln Gly Thr Arg Leu Glu Ile Lys
            100                 105

<210> SEQ ID NO 11
<211> LENGTH: 117
<212> TYPE: PRT
<213> ORGANISM: Artificial Sequence
<220> FEATURE:
<223> OTHER INFORMATION: CW6B233 Heavy Chain Variable Region

<400> SEQUENCE: 11

Gln Val Gln Leu Gln Glu Ser Gly Pro Gly Leu Val Lys Pro Ser Glu
 1               5                  10                  15

Thr Leu Ser Leu Thr Cys Thr Val Ser Gly Asn Ser Ile Arg Ser Tyr
                20                  25                  30

Tyr Trp Ser Trp Ile Arg Gln Pro Ala Gly Lys Gly Leu Glu Trp Ile
            35                  40                  45

Gly Arg Ile Tyr Ile Ser Gly Asn Thr Asn Tyr Asn Pro Ser Leu Lys
     50                  55                  60

Ser Arg Val Thr Met Ser Ile Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Leu Ser Gly Ile Asp Ala Phe Asp Ile Trp Gly Gln Gly Thr Met
            100                 105                 110

Val Thr Val Ser Ser
        115

<210> SEQ ID NO 12
<211> LENGTH: 107
<212> TYPE: PRT
<213> ORGANISM: Artificial Sequence
<220> FEATURE:
<223> OTHER INFORMATION: CW6B233 Light Chain Variable Region

<400> SEQUENCE: 12

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Thr Asn Tyr
                20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Phe Ala Thr Tyr Tyr Cys Gln Gln Tyr Asp Asn Leu Pro Ile
                 85                  90                  95

Thr Phe Gly Gln Gly Thr Arg Leu Glu Ile Lys
            100                 105

<210> SEQ ID NO 13
<211> LENGTH: 123
```

```
<212> TYPE: PRT
<213> ORGANISM: Artificial Sequence
<220> FEATURE:
<223> OTHER INFORMATION: CW6B237 Heavy Chain Variable Region

<400> SEQUENCE: 13

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Arg Met Gly Val Ser Trp Ile Arg Gln Pro Pro Gly Lys Ala Leu Glu
        35                  40                  45

Trp Leu Ala His Ile Phe Ser His Asp Glu Lys Phe Tyr Ser Thr Phe
    50                  55                  60

Leu Lys Ser Arg Leu Thr Ile Ser Lys Asp Thr Ser Lys Ser Gln Val
65                  70                  75                  80

Val Leu Met Met Thr Asn Met Asp Pro Val Asp Thr Ala Thr Tyr Tyr
                85                  90                  95

Cys Ala Arg Ile Ile Leu Ser Ser Gly His Asp Ala Phe Asp Ile
            100                 105                 110

Trp Gly Gln Gly Thr Met Val Thr Val Ser Ser
        115                 120

<210> SEQ ID NO 14
<211> LENGTH: 107
<212> TYPE: PRT
<213> ORGANISM: Artificial Sequence
<220> FEATURE:
<223> OTHER INFORMATION: CW6B237 Light Chain Variable Region

<400> SEQUENCE: 14

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg His Asn
            20                  25                  30

Leu Gly Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Ile Leu Thr Ile Ser Ser Leu Gln Pro
65                  70                  75                  80

Glu Asp Phe Ala Thr Phe Phe Cys Leu Gln Asp Tyr Ile Tyr Pro Leu
                85                  90                  95

Thr Phe Gly Gly Gly Thr Lys Val Glu Ile Lys
            100                 105

<210> SEQ ID NO 15
<211> LENGTH: 123
<212> TYPE: PRT
<213> ORGANISM: Artificial Sequence
<220> FEATURE:
<223> OTHER INFORMATION: CW6B238 Heavy Chain Variable Region

<400> SEQUENCE: 15

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Asn Asn Ala
            20                  25                  30

Arg Met Gly Val Ser Trp Ile Arg Gln Pro Pro Gly Lys Ala Leu Glu
```

```
                35                  40                  45

Trp Leu Ala His Met Phe Ser Ser Asp Glu Lys Phe Tyr Arg Thr Ser
             50                  55                  60

Leu Lys Ser Arg Leu Thr Ile Ser Lys Asp Thr Ser Lys Ser Gln Val
 65                  70                  75                  80

Val Leu Thr Met Thr Asn Met Asp Pro Val Asp Thr Ala Thr Tyr Tyr
                 85                  90                  95

Cys Ala Arg Ile Ser Leu Tyr Ser Ser Gly His Asp Thr Phe Asp Leu
            100                 105                 110

Trp Gly Gln Gly Thr Met Val Thr Val Ser Ser
            115                 120

<210> SEQ ID NO 16
<211> LENGTH: 107
<212> TYPE: PRT
<213> ORGANISM: Artificial Sequence
<220> FEATURE:
<223> OTHER INFORMATION: CW6B238 Light Chain Variable Region

<400> SEQUENCE: 16

Ala Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Arg Asn Thr
             20                  25                  30

Leu Gly Trp Tyr Gln Gln Lys Pro Gly Lys Ala Pro Asn Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Asp Tyr Asp Tyr Pro Leu
                 85                  90                  95

Thr Phe Gly Gly Gly Thr Lys Val Glu Ile Lys
            100                 105

<210> SEQ ID NO 17
<211> LENGTH: 121
<212> TYPE: PRT
<213> ORGANISM: Artificial Sequence
<220> FEATURE:
<223> OTHER INFORMATION: CW6B188 Heavy Chain Variable Region

<400> SEQUENCE: 17

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asn Tyr
             20                  25                  30

Trp Met Thr Trp Val Arg Gln Ala Pro Gly Lys Gly Leu Glu Trp Val
         35                  40                  45

Ala Asn Ile Lys Gln Ser Gly Asn Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Thr Leu Tyr Glu Trp Glu Leu Glu Pro Phe Asp Tyr Trp Gly
            100                 105                 110
```

```
Gln Gly Thr Leu Val Thr Val Ser Ser
        115                 120
```

<210> SEQ ID NO 18
<211> LENGTH: 108
<212> TYPE: PRT
<213> ORGANISM: Artificial Sequence
<220> FEATURE:
<223> OTHER INFORMATION: CW6B188 Light Chain Variable Region

<400> SEQUENCE: 18

```
Ser Tyr Val Leu Thr Gln Pro Pro Ser Val Ser Val Ala Pro Gly Gln
1               5                   10                  15

Thr Ala Arg Ile Thr Cys Gly Gly Asn Arg Ile Gly Ser Lys Asn Leu
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Ser Thr Ala Thr Leu Thr Ile Ser Arg Val Glu Ala Gly
65                  70                  75                  80

Asp Glu Ala Asp Tyr Tyr Cys Gln Val Trp Asp Ser Ser Arg Asp His
                85                  90                  95

Val Val Phe Gly Gly Gly Thr Lys Leu Thr Val Leu
            100                 105
```

<210> SEQ ID NO 19
<211> LENGTH: 369
<212> TYPE: DNA
<213> ORGANISM: Artificial Sequence
<220> FEATURE:
<223> OTHER INFORMATION: CW6B130 Heavy Chain Variable Region

<400> SEQUENCE: 19

```
cagctgcagc tgcaggagag cggacccgga ctggtgaagc ctagcgagac cctgagcctg      60
acctgtaccg tgagcggcgc cagcatcagc agcatcaact actactgggg ctggatcagg     120 cagcccctg gaagggcct ggagtggatc ggcagctttt actacagcgg caacacctac        180
tacaacccca gcctgaagtc cagggtgacc atcagcgtgg acaccagcaa gaactacttc     240
agcctgaagc tgaacagcgt gaccgccgcc gacaccgctg tgtactactg cgccagggag      300
tactacgaca gcagcggcta ctacccctt gagccctggg gccagggaac cctggtgaca       360
gtgagcagc                                                             369
```

<210> SEQ ID NO 20
<211> LENGTH: 324
<212> TYPE: DNA
<213> ORGANISM: Artificial Sequence
<220> FEATURE:
<223> OTHER INFORMATION: CW6B130 Light Chain Variable Region

<400> SEQUENCE: 20

```
agctacgtgc tgacccagcc tcctagcgtg agcgtggctc ctggacagac cgccagaatc      60
acctgcggcg gcgacaacat cggcagcgag agcgtgcact ggtaccagca gaagcctgga     120
caggcccccg tgctggtggt gtacgacgac accgacaggc ccagcggcat tcccgagagg     180
ttcagcggct ccaagagcgg caccacagcc accctgacca tcagctgggt ggaggccggc     240
gatgaggccg actactactg ccaggtgtgg gacagcagca gcgaccatgt tgttttggc      300 ggcggcacca agctgaccgt gctg                                            324
```

<210> SEQ ID NO 21
<211> LENGTH: 363
<212> TYPE: DNA
<213> ORGANISM: Artificial Sequence
<220> FEATURE:
<223> OTHER INFORMATION: CW6B175 Heavy Chain Variable Region

<400> SEQUENCE: 21

```
gaggtgcagc tggtggagag cggaggcgga ctcgtgcagc tggaggaag cctgagactg      60 agctgtgccg ccagcggctt caccttcacc aactactgga tgacctgggt gagacaggcc    120
cccggaaagg gactggagtg ggtggccaac atcaagcaga cggcagcga gaagtactac     180 gtggacagcg tcaagggcag gttcaccatc agcagggaca cgccaagaa cagcctgtac     240 ctgcagatga actccctgag ggccgaggac accgccgtgt actactgcgc caggaccctg    300
tacgaatggg agctggagcc ctttgactac tggggccagg gcacactggt gaccgtgagc    360
agc                                                                  363
```

<210> SEQ ID NO 22
<211> LENGTH: 324
<212> TYPE: DNA
<213> ORGANISM: Artificial Sequence
<220> FEATURE:
<223> OTHER INFORMATION: CW6B175 Light Chain Variable Region

<400> SEQUENCE: 22

```
agctacgtgc tgacccagcc tcctagcgtg agcgtggctc ctggccagac agccaggatc     60
acctgcggcg gcaacaggat cggcagcaag agcgtgcact ggtaccagca gaagcctggc    120
caggcccctg tgctggtggt gttcgacgac agcgacaggc ctagcggcat ccccgagagg    180
ttcagcggca gcaacagcgg catcaccgcc accctgacca tcagcagagt ggaggccggc    240
gacgaggccg actactactg ccaggtgtgg gacagcagca cgaccatgt tgttttcggc     300 ggcggcacca agctgaccgt gctg                                           324
```

<210> SEQ ID NO 23
<211> LENGTH: 351
<212> TYPE: DNA
<213> ORGANISM: Artificial Sequence
<220> FEATURE:
<223> OTHER INFORMATION: CW6B228 Heavy Chain Variable Region

<400> SEQUENCE: 23

```
caggtgcagc tgcaggagag cggccctgga ctggtgaagc ccagcgagac cctgagcctg     60
acctgcaccg tgagcggcaa cagcatcagg agctactact ggagctggat cagacagccc    120
gccggcaaag gcctggagtg gatcggcagg atctacatca cggcaacac caactacaac     180 cccagcctga agtccagggt gaccatgtcc atcgacacca gcaagaacca gttcagcctg    240
aagctgagca gcgtgaccgc tgctgacacc gccgtgtact actgcgccag actgagcggc    300
atcgacgcct cgacatctg ggccagggc accatggtga ccgtgagcag c               351
```

<210> SEQ ID NO 24
<211> LENGTH: 321
<212> TYPE: DNA
<213> ORGANISM: Artificial Sequence
<220> FEATURE:
<223> OTHER INFORMATION: CW6B228 Light Chain Variable Region

<400> SEQUENCE: 24

```
gacatccaga tgacccagag ccctagcagc ctgtccgcca gcgtgggcga tagggtgacc    60
attacttgtc aagcttctca ggacatcaac aactacctga actggtacca gcagaagccc   120
ggcaaggccc ccaagctgct gatctacgac gccagcagcc tggagacagg cgtgcctagc   180
aggttcagcg gaagcggcag cggcaccgac ttcaccttca ccatcagctc cctgcagccc   240
gaggacttcg ccacctacta ctgccagcag tacgacgacc tgcccatcac cttcggccag   300
ggcaccagac tggagatcaa g                                              321

<210> SEQ ID NO 25
<211> LENGTH: 351
<212> TYPE: DNA
<213> ORGANISM: Artificial Sequence
<220> FEATURE:
<223> OTHER INFORMATION: CW6B229 Heavy Chain Variable Region

<400> SEQUENCE: 25
caggtgcagc tgcaggagag cggacccgga ctggtgaaac ccagcgagac cctgagcctg    60
acctgcaccg tgagcggcaa cagcatcagg tcctactact ggagctggat caggcagcct   120
gccggcaaag gcctggagtg gatcggcagg atctacatca gcggcaacac caactacaac   180
cccagcctga gagcagggt gaccatgagc atcgacacca gcaagaacca gttcagcctg   240
aagctgagca gcgtgacagc cgctgacacc gccgtgttct actgcgccag gctgagcggc   300
atcgacgcct cgacatctg gggccagggc accatggtga ccgtgagcag c             351

<210> SEQ ID NO 26
<211> LENGTH: 321
<212> TYPE: DNA
<213> ORGANISM: Artificial Sequence
<220> FEATURE:
<223> OTHER INFORMATION: CW6B229 Light Chain Variable Region

<400> SEQUENCE: 26
gacatccaga tgacccagag ccctagcagc ctgagcgcca gcgtgggcga tagggtgacc    60
attacttgtc aagcttctca ggacatcagc aactacctga actggtacca gcagaagccc   120
ggcaaggccc ccaagctgct gatctacgac gccagcaacc tggagaccgg cgtgcctagc   180
agatttagcg gcagcggcag cggcaccgat ttcaccttca ccatcagcag cctgcagccc   240
gaggacttcg ccacctacta ctgccagcag tacgacaacc tgcccatcac cttcggccag   300
ggcaccaggc tggagatcaa g                                              321

<210> SEQ ID NO 27
<211> LENGTH: 351
<212> TYPE: DNA
<213> ORGANISM: Artificial Sequence
<220> FEATURE:
<223> OTHER INFORMATION: CW6B230 Heavy Chain Variable Region

<400> SEQUENCE: 27
caggtgcagc tgcaggagag cggacctggc ctggtgaagc ccagcgagac cctgagcctg    60
acctgcaccg tgagcggcaa cagcatcagc aactactact ggagctggat caggcagcct   120
gctggcaagg gcctggagtg gatcggcagg atctacatca ccggcaacac caactacaac   180
cctagcctga gagcagggt gaccatgagc ctggacacca gcaagaacca gttcagcctg   240
aagctgtcca gcgtgacagc cgctgacacc gccgtgtact actgcgccag gctgagcggc   300
atcgacgcct cgacatctg gggccagggc accatggtga ccgtgagcag c             351
```

```
<210> SEQ ID NO 28
<211> LENGTH: 321
<212> TYPE: DNA
<213> ORGANISM: Artificial Sequence
<220> FEATURE:
<223> OTHER INFORMATION: CW6B230 Light Chain Variable Region

<400> SEQUENCE: 28
gacatccaga tgacccagag ccctagcaca ctgagcgcct ccgtgggcga cagagtgacc      60
tttacttgtc aagcttctca ggacatcacc aagtacctga actggtacca gcagaagccc     120
ggcaaggccc ccaagctgct gatctatgac gccagcaatc tggagaccgg cgtgcccagc     180
agattcagcg gaagcggcag cggcaccgac ttcaccttca ccatcagcag cctgcagccc     240
gaggacttcg ccacctacta ctgccagcag tacgacgacc tgcctatcac cttcggccag     300
ggcaccaggc tggagatcaa g                                               321

<210> SEQ ID NO 29
<211> LENGTH: 351
<212> TYPE: DNA
<213> ORGANISM: Artificial Sequence
<220> FEATURE:
<223> OTHER INFORMATION: CW6B233 Heavy Chain Variable Region

<400> SEQUENCE: 29
caggtgcagc tgcaggagag cggccctgga ctggtgaagc ccagcgagac cctgagcctg      60
acctgcaccg tgagcggcaa cagcatcagg agctactact ggagctggat cagacagccc     120
gccggcaaag gcctggagtg gatcggcagg atctacatca gcggcaacac caactacaac     180
cccagcctga agtccagggt gaccatgtcc atcgacacca gcaagaacca gttcagcctg     240
aagctgagca gcgtgaccgc tgctgacacc gccgtgtact actgcgccag actgagcggc     300
atcgacgcct cgacatctg gggccagggc accatggtga ccgtgagcag c                351

<210> SEQ ID NO 30
<211> LENGTH: 321
<212> TYPE: DNA
<213> ORGANISM: Artificial Sequence
<220> FEATURE:
<223> OTHER INFORMATION: CW6B233 Light Chain Variable Region

<400> SEQUENCE: 30
gacatccaga tgacccaaag ccctagcagc ctgagcgcca gcgtgggcga tagggtgacc      60
attacttgtc aagcttctca ggacatcacc aactacctga actggtacca gcagaagccc     120
ggcaaggccc ccaagctgct gatctacgac gcctccaacc tggagaccgg agtgcccagc     180
agatttagcg gcagcggcag cggcaccgac tttaccttca ccatcagcag cctgcagccc     240
gaggacttcg ccacctacta ctgccagcag tacgacaacc tgcccatcac cttcggccag     300
ggcaccaggc tggagatcaa g                                               321

<210> SEQ ID NO 31
<211> LENGTH: 369
<212> TYPE: DNA
<213> ORGANISM: Artificial Sequence
<220> FEATURE:
<223> OTHER INFORMATION: CW6B237 Heavy Chain Variable Region

<400> SEQUENCE: 31
caggtgacac tgaaggagag cggccccgtg ctggtgaagc ctaccgagac cctgaccctg      60
acctgcaccg tgagcggctt cagcctgagc aacgccagga tgggcgtgag ctggatcaga     120
```

```
cagcctcctg gcaaagccct ggagtggctg gcccacatct tctcccacga cgagaagttc      180
tacagcacct tcctgaagag caggctgacc atctccaagg acacctccaa gagccaggtg      240
gtgctgatga tgaccaacat ggaccccgtc gacaccgcca cctactactg cgccaggatc      300
atcctgagca gcagcggcca cgacgccttc gacatctggg gccagggcac catggtgacc      360
gtgagcagc                                                              369
```

```
<210> SEQ ID NO 32
<211> LENGTH: 321
<212> TYPE: DNA
<213> ORGANISM: Artificial Sequence
<220> FEATURE:
<223> OTHER INFORMATION: CW6B237 Light Chain Variable Region

<400> SEQUENCE: 32
gccatccaga tgacccagag ccctagcagc ctgagcgcta gcgtgggcga cagggtgacc      60
attacttgtc gtgcttctca ggacatcagg cacaacctgg ctggtacca gcagaagccc      120 ggcaaggccc ccaacctgct gatctacgcc gccagcagcc tgcagagcgg agtgcctagc      180
aggtttagcg gcagcggcag cggcaccgac ttcatcctga ccatcagcag cctgcagccc      240
gaggacttcg ccaccttctt ctgcctgcag gactacatct accctctgac cttcggcggc      300
ggcaccaagg tggagatcaa g                                                321
```

```
<210> SEQ ID NO 33
<211> LENGTH: 369
<212> TYPE: DNA
<213> ORGANISM: Artificial Sequence
<220> FEATURE:
<223> OTHER INFORMATION: CW6B238 Heavy Chain Variable Region

<400> SEQUENCE: 33
caggtgaccc tgaaggagtc cggccccgtg ctggtgaaac ccaccgagac cctgaccctg      60
acctgcaccg tgtccggctt cagcctgaac aacgccagga tgggcgtgag ctggatcaga      120
cagcctcccg gcaaagccct ggagtggctg gcccacatgt tcagcagcga cgagaagttc      180
tacaggacca gcctgaagag caggctgacc atcagcaagg acacctccaa gagccaggtg      240
gtgctgacca tgaccaacat ggaccccgtg gacaccgcca cctactactg cgccagaatc      300
agcctgtaca gcagcggcca cgacaccttc gacctgtggg gccagggcac catggtgacc      360
gtgagcagc                                                              369
```

```
<210> SEQ ID NO 34
<211> LENGTH: 321
<212> TYPE: DNA
<213> ORGANISM: Artificial Sequence
<220> FEATURE:
<223> OTHER INFORMATION: CW6B238 Light Chain Variable Region

<400> SEQUENCE: 34
gccatccaga tgacccagag ccctagcagc ctgagcgcca gcgtgggaga cagagtgacc      60
attacttgtc gtgcttctca ggacatcagg aacaccctgg ctggtacca gcagaagccc      120 ggcaaggccc ccaacctgct gatctacgcc gccagcagcc tgcagagcgg agtgcctagc      180
agattcagcg gcagcggctc cggcacagac ttcaccctga ccatcagcag cctgcagccc      240
gaggacttcg ccacctacta ctgcctgcag gattacgact accctctgac cttcggcggc      300
ggcaccaagg tggagatcaa g                                                321
```

<210> SEQ ID NO 35
<211> LENGTH: 363
<212> TYPE: DNA
<213> ORGANISM: Artificial Sequence
<220> FEATURE:
<223> OTHER INFORMATION: CW6B188 Heavy Chain Variable Region

<400> SEQUENCE: 35

```
gaggtgcagc tggtggagag cggaggcgga ctggtgcagc tggaggaag cctgagactg      60
agctgcgctg ccagcggctt caccttcacc aactactgga tgacctgggt gagacaggcc    120
cctggaaagg gcctggagtg ggtggccaac atcaagcaga gcggcaacga aagtactac     180
gtggatagcg tgaagggcag gttcaccatc tccaggaca acgccaagaa ctccctgtac     240
ctgcagatga actccctgag agccgaggac accgccgtgt actactgcgc caggaccctg    300
tacgagtggg gctggagcc cttcgactac tggggccagg gaaccctggt gaccgtgagc     360
agc                                                                   363
```

<210> SEQ ID NO 36
<211> LENGTH: 324
<212> TYPE: DNA
<213> ORGANISM: Artificial Sequence
<220> FEATURE:
<223> OTHER INFORMATION: CW6B188 Light Chain Variable Region

<400> SEQUENCE: 36

```
agctacgtgc tgacacagcc tcccagcgtg agcgtggctc ctggacagac cgccaggatc     60
acctgcggcg gcaacaggat cggcagcaag aacctgcact ggtaccagca gaagcctggc    120
caggcccctg tgctggtggt gtacgacgac agcgacaggc cctccggcat ccctgagagg    180
ttcagcggca gcaatagcgg cagcaccgcc accctgacca tctccagagt ggaggccggc    240
gatgaggccg actactactg ccaggtgtgg gacagcagca gagaccatgt tgttttcggc    300
ggcggcacca agctgaccgt gctg                                            324
```

<210> SEQ ID NO 37
<211> LENGTH: 7
<212> TYPE: PRT
<213> ORGANISM: Artificial Sequence
<220> FEATURE:
<223> OTHER INFORMATION: CW6B130 HCDR1

<400> SEQUENCE: 37

Ser Ile Asn Tyr Tyr Trp Gly
1               5

<210> SEQ ID NO 38
<211> LENGTH: 16
<212> TYPE: PRT
<213> ORGANISM: Artificial Sequence
<220> FEATURE:
<223> OTHER INFORMATION: CW6B130 HCDR2

<400> SEQUENCE: 38

Ser Phe Tyr Tyr Ser Gly Asn Thr Tyr Tyr Asn Pro Ser Leu Lys Ser
1               5                   10                  15

<210> SEQ ID NO 39
<211> LENGTH: 13
<212> TYPE: PRT
<213> ORGANISM: Artificial Sequence
<220> FEATURE:
<223> OTHER INFORMATION: CW6B130 HCDR3

```
<400> SEQUENCE: 39

Glu Tyr Tyr Asp Ser Ser Gly Tyr Tyr Pro Phe Glu Pro
1               5                   10

<210> SEQ ID NO 40
<211> LENGTH: 5
<212> TYPE: PRT
<213> ORGANISM: Artificial Sequence
<220> FEATURE:
<223> OTHER INFORMATION: CW6B175 HCDR1

<400> SEQUENCE: 40

Asn Tyr Trp Met Thr
1               5

<210> SEQ ID NO 41
<211> LENGTH: 17
<212> TYPE: PRT
<213> ORGANISM: Artificial Sequence
<220> FEATURE:
<223> OTHER INFORMATION: CW6B175 HCDR2

<400> SEQUENCE: 41

Asn Ile Lys Gln Ser Gly Ser Glu Lys Tyr Tyr Val Asp Ser Val Lys
1               5                   10                  15

Gly

<210> SEQ ID NO 42
<211> LENGTH: 12
<212> TYPE: PRT
<213> ORGANISM: Artificial Sequence
<220> FEATURE:
<223> OTHER INFORMATION: CW6B175 HCDR3

<400> SEQUENCE: 42

Thr Leu Tyr Glu Trp Glu Leu Glu Pro Phe Asp Tyr
1               5                   10

<210> SEQ ID NO 43
<211> LENGTH: 5
<212> TYPE: PRT
<213> ORGANISM: Artificial Sequence
<220> FEATURE:
<223> OTHER INFORMATION: CW6B228 HCDR1

<400> SEQUENCE: 43

Ser Tyr Tyr Trp Ser
1               5

<210> SEQ ID NO 44
<211> LENGTH: 16
<212> TYPE: PRT
<213> ORGANISM: Artificial Sequence
<220> FEATURE:
<223> OTHER INFORMATION: CW6B228 HCDR2

<400> SEQUENCE: 44

Arg Ile Tyr Ile Ser Gly Asn Thr Asn Tyr Asn Pro Ser Leu Lys Ser
1               5                   10                  15

<210> SEQ ID NO 45
<211> LENGTH: 9
<212> TYPE: PRT
<213> ORGANISM: Artificial Sequence
<220> FEATURE:
<223> OTHER INFORMATION: CW6B228 HCDR3
```

```
<400> SEQUENCE: 45

Leu Ser Gly Ile Asp Ala Phe Asp Ile
1               5

<210> SEQ ID NO 46
<211> LENGTH: 5
<212> TYPE: PRT
<213> ORGANISM: Artificial Sequence
<220> FEATURE:
<223> OTHER INFORMATION: CW6B229 HCDR1

<400> SEQUENCE: 46

Ser Tyr Tyr Trp Ser
1               5

<210> SEQ ID NO 47
<211> LENGTH: 16
<212> TYPE: PRT
<213> ORGANISM: Artificial Sequence
<220> FEATURE:
<223> OTHER INFORMATION: CW6B229 HCDR2

<400> SEQUENCE: 47

Arg Ile Tyr Ile Ser Gly Asn Thr Asn Tyr Asn Pro Ser Leu Lys Ser
1               5                   10                  15

<210> SEQ ID NO 48
<211> LENGTH: 9
<212> TYPE: PRT
<213> ORGANISM: Artificial Sequence
<220> FEATURE:
<223> OTHER INFORMATION: CW6B229 HCDR3

<400> SEQUENCE: 48

Leu Ser Gly Ile Asp Ala Phe Asp Ile
1               5

<210> SEQ ID NO 49
<211> LENGTH: 5
<212> TYPE: PRT
<213> ORGANISM: Artificial Sequence
<220> FEATURE:
<223> OTHER INFORMATION: CW6B230 HCDR1

<400> SEQUENCE: 49

Asn Tyr Tyr Trp Ser
1               5

<210> SEQ ID NO 50
<211> LENGTH: 16
<212> TYPE: PRT
<213> ORGANISM: Artificial Sequence
<220> FEATURE:
<223> OTHER INFORMATION: CW6B230 HCDR2

<400> SEQUENCE: 50

Arg Ile Tyr Ile Thr Gly Asn Thr Asn Tyr Asn Pro Ser Leu Lys Ser
1               5                   10                  15

<210> SEQ ID NO 51
<211> LENGTH: 9
<212> TYPE: PRT
<213> ORGANISM: Artificial Sequence
<220> FEATURE:
<223> OTHER INFORMATION: CW6B230 HCDR3
```

```
<400> SEQUENCE: 51

Leu Ser Gly Ile Asp Ala Phe Asp Ile
 1               5

<210> SEQ ID NO 52
<211> LENGTH: 5
<212> TYPE: PRT
<213> ORGANISM: Artificial Sequence
<220> FEATURE:
<223> OTHER INFORMATION: CW6B233 HCDR1

<400> SEQUENCE: 52

Ser Tyr Tyr Trp Ser
 1               5

<210> SEQ ID NO 53
<211> LENGTH: 16
<212> TYPE: PRT
<213> ORGANISM: Artificial Sequence
<220> FEATURE:
<223> OTHER INFORMATION: CW6B233 HCDR2

<400> SEQUENCE: 53

Arg Ile Tyr Ile Ser Gly Asn Thr Asn Tyr Asn Pro Ser Leu Lys Ser
 1               5                  10                  15

<210> SEQ ID NO 54
<211> LENGTH: 9
<212> TYPE: PRT
<213> ORGANISM: Artificial Sequence
<220> FEATURE:
<223> OTHER INFORMATION: CW6B233 HCDR3

<400> SEQUENCE: 54

Leu Ser Gly Ile Asp Ala Phe Asp Ile
 1               5

<210> SEQ ID NO 55
<211> LENGTH: 7
<212> TYPE: PRT
<213> ORGANISM: Artificial Sequence
<220> FEATURE:
<223> OTHER INFORMATION: CW6B237 HCDR1

<400> SEQUENCE: 55

Asn Ala Arg Met Gly Val Ser
 1               5

<210> SEQ ID NO 56
<211> LENGTH: 16
<212> TYPE: PRT
<213> ORGANISM: Artificial Sequence
<220> FEATURE:
<223> OTHER INFORMATION: CW6B237 HCDR2

<400> SEQUENCE: 56

His Ile Phe Ser His Asp Glu Lys Phe Tyr Ser Thr Phe Leu Lys Ser
 1               5                  10                  15

<210> SEQ ID NO 57
<211> LENGTH: 13
<212> TYPE: PRT
<213> ORGANISM: Artificial Sequence
<220> FEATURE:
<223> OTHER INFORMATION: CW6B237 HCDR3

<400> SEQUENCE: 57
```

Ile Ile Leu Ser Ser Ser Gly His Asp Ala Phe Asp Ile
1               5                   10

<210> SEQ ID NO 58
<211> LENGTH: 7
<212> TYPE: PRT
<213> ORGANISM: Artificial Sequence
<220> FEATURE:
<223> OTHER INFORMATION: CW6B238 HCDR1

<400> SEQUENCE: 58

Asn Ala Arg Met Gly Val Ser
1               5

<210> SEQ ID NO 59
<211> LENGTH: 16
<212> TYPE: PRT
<213> ORGANISM: Artificial Sequence
<220> FEATURE:
<223> OTHER INFORMATION: CW6B238 HCDR2

<400> SEQUENCE: 59

His Met Phe Ser Ser Asp Glu Lys Phe Tyr Arg Thr Ser Leu Lys Ser
1               5                   10                  15

<210> SEQ ID NO 60
<211> LENGTH: 13
<212> TYPE: PRT
<213> ORGANISM: Artificial Sequence
<220> FEATURE:
<223> OTHER INFORMATION: CW6B238 HCDR3

<400> SEQUENCE: 60

Ile Ser Leu Tyr Ser Ser Gly His Asp Thr Phe Asp Leu
1               5                   10

<210> SEQ ID NO 61
<211> LENGTH: 5
<212> TYPE: PRT
<213> ORGANISM: Artificial Sequence
<220> FEATURE:
<223> OTHER INFORMATION: CW6B188 HCDR1

<400> SEQUENCE: 61

Asn Tyr Trp Met Thr
1               5

<210> SEQ ID NO 62
<211> LENGTH: 17
<212> TYPE: PRT
<213> ORGANISM: Artificial Sequence
<220> FEATURE:
<223> OTHER INFORMATION: CW6B188 HCDR2

<400> SEQUENCE: 62

Asn Ile Lys Gln Ser Gly Asn Glu Lys Tyr Tyr Val Asp Ser Val Lys
1               5                   10                  15

Gly

<210> SEQ ID NO 63
<211> LENGTH: 12
<212> TYPE: PRT
<213> ORGANISM: Artificial Sequence
<220> FEATURE:
<223> OTHER INFORMATION: CW6B188 HCDR3

```
<400> SEQUENCE: 63

Thr Leu Tyr Glu Trp Glu Leu Glu Pro Phe Asp Tyr
1               5                   10

<210> SEQ ID NO 64
<211> LENGTH: 11
<212> TYPE: PRT
<213> ORGANISM: Artificial Sequence
<220> FEATURE:
<223> OTHER INFORMATION: CW6B130 LCDR1

<400> SEQUENCE: 64

Gly Gly Asp Asn Ile Gly Ser Glu Ser Val His
1               5                   10

<210> SEQ ID NO 65
<211> LENGTH: 7
<212> TYPE: PRT
<213> ORGANISM: Artificial Sequence
<220> FEATURE:
<223> OTHER INFORMATION: CW6B130 LCDR2

<400> SEQUENCE: 65

Asp Asp Thr Asp Arg Pro Ser
1               5

<210> SEQ ID NO 66
<211> LENGTH: 11
<212> TYPE: PRT
<213> ORGANISM: Artificial Sequence
<220> FEATURE:
<223> OTHER INFORMATION: CW6B130 LCDR3

<400> SEQUENCE: 66

Gln Val Trp Asp Ser Ser Ser Asp His Val Val
1               5                   10

<210> SEQ ID NO 67
<211> LENGTH: 11
<212> TYPE: PRT
<213> ORGANISM: Artificial Sequence
<220> FEATURE:
<223> OTHER INFORMATION: CW6B175 LCDR1

<400> SEQUENCE: 67

Gly Gly Asn Arg Ile Gly Ser Lys Ser Val His
1               5                   10

<210> SEQ ID NO 68
<211> LENGTH: 7
<212> TYPE: PRT
<213> ORGANISM: Artificial Sequence
<220> FEATURE:
<223> OTHER INFORMATION: CW6B175 LCDR2

<400> SEQUENCE: 68

Asp Asp Ser Asp Arg Pro Ser
1               5

<210> SEQ ID NO 69
<211> LENGTH: 11
<212> TYPE: PRT
<213> ORGANISM: Artificial Sequence
<220> FEATURE:
<223> OTHER INFORMATION: CW6B175 LCDR3

<400> SEQUENCE: 69
```

```
Gln Val Trp Asp Ser Ser Asn Asp His Val Val
1               5                   10

<210> SEQ ID NO 70
<211> LENGTH: 11
<212> TYPE: PRT
<213> ORGANISM: Artificial Sequence
<220> FEATURE:
<223> OTHER INFORMATION: CW6B228 LCDR1

<400> SEQUENCE: 70

Gln Ala Ser Gln Asp Ile Asn Asn Tyr Leu Asn
1               5                   10

<210> SEQ ID NO 71
<211> LENGTH: 7
<212> TYPE: PRT
<213> ORGANISM: Artificial Sequence
<220> FEATURE:
<223> OTHER INFORMATION: CW6B228 LCDR2

<400> SEQUENCE: 71

Asp Ala Ser Ser Leu Glu Thr
1               5

<210> SEQ ID NO 72
<211> LENGTH: 9
<212> TYPE: PRT
<213> ORGANISM: Artificial Sequence
<220> FEATURE:
<223> OTHER INFORMATION: CW6B228 LCDR3

<400> SEQUENCE: 72

Gln Gln Tyr Asp Asp Leu Pro Ile Thr
1               5

<210> SEQ ID NO 73
<211> LENGTH: 11
<212> TYPE: PRT
<213> ORGANISM: Artificial Sequence
<220> FEATURE:
<223> OTHER INFORMATION: CW6B229 LCDR1

<400> SEQUENCE: 73

Gln Ala Ser Gln Asp Ile Ser Asn Tyr Leu Asn
1               5                   10

<210> SEQ ID NO 74
<211> LENGTH: 7
<212> TYPE: PRT
<213> ORGANISM: Artificial Sequence
<220> FEATURE:
<223> OTHER INFORMATION: CW6B229 LCDR2

<400> SEQUENCE: 74

Asp Ala Ser Asn Leu Glu Thr
1               5

<210> SEQ ID NO 75
<211> LENGTH: 9
<212> TYPE: PRT
<213> ORGANISM: Artificial Sequence
<220> FEATURE:
<223> OTHER INFORMATION: CW6B229 LCDR3

<400> SEQUENCE: 75
```

```
Gln Gln Tyr Asp Asn Leu Pro Ile Thr
1               5

<210> SEQ ID NO 76
<211> LENGTH: 11
<212> TYPE: PRT
<213> ORGANISM: Artificial Sequence
<220> FEATURE:
<223> OTHER INFORMATION: CW6B230 LCDR1

<400> SEQUENCE: 76

Gln Ala Ser Gln Asp Ile Thr Lys Tyr Leu Asn
1               5                  10

<210> SEQ ID NO 77
<211> LENGTH: 7
<212> TYPE: PRT
<213> ORGANISM: Artificial Sequence
<220> FEATURE:
<223> OTHER INFORMATION: CW6B230 LCDR2

<400> SEQUENCE: 77

Asp Ala Ser Asn Leu Glu Thr
1               5

<210> SEQ ID NO 78
<211> LENGTH: 9
<212> TYPE: PRT
<213> ORGANISM: Artificial Sequence
<220> FEATURE:
<223> OTHER INFORMATION: CW6B230 LCDR3

<400> SEQUENCE: 78

Gln Gln Tyr Asp Asp Leu Pro Ile Thr
1               5

<210> SEQ ID NO 79
<211> LENGTH: 11
<212> TYPE: PRT
<213> ORGANISM: Artificial Sequence
<220> FEATURE:
<223> OTHER INFORMATION: CW6B233 LCDR1

<400> SEQUENCE: 79

Gln Ala Ser Gln Asp Ile Thr Asn Tyr Leu Asn
1               5                  10

<210> SEQ ID NO 80
<211> LENGTH: 7
<212> TYPE: PRT
<213> ORGANISM: Artificial Sequence
<220> FEATURE:
<223> OTHER INFORMATION: CW6B233 LCDR2

<400> SEQUENCE: 80

Asp Ala Ser Asn Leu Glu Thr
1               5

<210> SEQ ID NO 81
<211> LENGTH: 9
<212> TYPE: PRT
<213> ORGANISM: Artificial Sequence
<220> FEATURE:
<223> OTHER INFORMATION: CW6B233 LCDR3

<400> SEQUENCE: 81

Gln Gln Tyr Asp Asn Leu Pro Ile Thr
```

```
1               5

<210> SEQ ID NO 82
<211> LENGTH: 11
<212> TYPE: PRT
<213> ORGANISM: Artificial Sequence
<220> FEATURE:
<223> OTHER INFORMATION: CW6B237 LCDR1

<400> SEQUENCE: 82

Arg Ala Ser Gln Asp Ile Arg His Asn Leu Gly
1               5                   10

<210> SEQ ID NO 83
<211> LENGTH: 7
<212> TYPE: PRT
<213> ORGANISM: Artificial Sequence
<220> FEATURE:
<223> OTHER INFORMATION: CW6B237 LCDR2

<400> SEQUENCE: 83

Ala Ala Ser Ser Leu Gln Ser
1               5

<210> SEQ ID NO 84
<211> LENGTH: 9
<212> TYPE: PRT
<213> ORGANISM: Artificial Sequence
<220> FEATURE:
<223> OTHER INFORMATION: CW6B237 LCDR3

<400> SEQUENCE: 84

Leu Gln Asp Tyr Ile Tyr Pro Leu Thr
1               5

<210> SEQ ID NO 85
<211> LENGTH: 11
<212> TYPE: PRT
<213> ORGANISM: Artificial Sequence
<220> FEATURE:
<223> OTHER INFORMATION: CW6B238 LCDR1

<400> SEQUENCE: 85

Arg Ala Ser Gln Asp Ile Arg Asn Thr Leu Gly
1               5                   10

<210> SEQ ID NO 86
<211> LENGTH: 7
<212> TYPE: PRT
<213> ORGANISM: Artificial Sequence
<220> FEATURE:
<223> OTHER INFORMATION: CW6B238 LCDR2

<400> SEQUENCE: 86

Ala Ala Ser Ser Leu Gln Ser
1               5

<210> SEQ ID NO 87
<211> LENGTH: 9
<212> TYPE: PRT
<213> ORGANISM: Artificial Sequence
<220> FEATURE:
<223> OTHER INFORMATION: CW6B238 LCDR3

<400> SEQUENCE: 87

Leu Gln Asp Tyr Asp Tyr Pro Leu Thr
1               5
```

```
<210> SEQ ID NO 88
<211> LENGTH: 11
<212> TYPE: PRT
<213> ORGANISM: Artificial Sequence
<220> FEATURE:
<223> OTHER INFORMATION: CW6B188 LCDR1

<400> SEQUENCE: 88

Gly Gly Asn Arg Ile Gly Ser Lys Asn Leu His
1               5                   10

<210> SEQ ID NO 89
<211> LENGTH: 7
<212> TYPE: PRT
<213> ORGANISM: Artificial Sequence
<220> FEATURE:
<223> OTHER INFORMATION: CW6B188 LCDR2

<400> SEQUENCE: 89

Asp Asp Ser Asp Arg Pro Ser
1               5

<210> SEQ ID NO 90
<211> LENGTH: 11
<212> TYPE: PRT
<213> ORGANISM: Artificial Sequence
<220> FEATURE:
<223> OTHER INFORMATION: CW6B188 LCDR3

<400> SEQUENCE: 90

Gln Val Trp Asp Ser Ser Arg Asp His Val Val
1               5                   10

<210> SEQ ID NO 91
<211> LENGTH: 9
<212> TYPE: PRT
<213> ORGANISM: Artificial Sequence
<220> FEATURE:
<223> OTHER INFORMATION: CW6B130 HCDR1

<400> SEQUENCE: 91

Gly Ala Ser Ile Ser Ser Ile Asn Tyr
1               5

<210> SEQ ID NO 92
<211> LENGTH: 5
<212> TYPE: PRT
<213> ORGANISM: Artificial Sequence
<220> FEATURE:
<223> OTHER INFORMATION: CW6B130 HCDR2

<400> SEQUENCE: 92

Tyr Tyr Ser Gly Asn
1               5

<210> SEQ ID NO 93
<211> LENGTH: 12
<212> TYPE: PRT
<213> ORGANISM: Artificial Sequence
<220> FEATURE:
<223> OTHER INFORMATION: CW6B130 HCDR3

<400> SEQUENCE: 93

Glu Tyr Tyr Asp Ser Ser Gly Tyr Tyr Pro Phe Glu
1               5                   10
```

<210> SEQ ID NO 94
<211> LENGTH: 7
<212> TYPE: PRT
<213> ORGANISM: Artificial Sequence
<220> FEATURE:
<223> OTHER INFORMATION: CW6B175 HCDR1

<400> SEQUENCE: 94

Gly Phe Thr Phe Thr Asn Tyr
1               5

<210> SEQ ID NO 95
<211> LENGTH: 6
<212> TYPE: PRT
<213> ORGANISM: Artificial Sequence
<220> FEATURE:
<223> OTHER INFORMATION: CW6B175 HCDR2

<400> SEQUENCE: 95

Lys Gln Ser Gly Ser Glu
1               5

<210> SEQ ID NO 96
<211> LENGTH: 11
<212> TYPE: PRT
<213> ORGANISM: Artificial Sequence
<220> FEATURE:
<223> OTHER INFORMATION: CW6B175 HCDR3

<400> SEQUENCE: 96

Thr Leu Tyr Glu Trp Glu Leu Glu Pro Phe Asp
1               5                   10

<210> SEQ ID NO 97
<211> LENGTH: 7
<212> TYPE: PRT
<213> ORGANISM: Artificial Sequence
<220> FEATURE:
<223> OTHER INFORMATION: CW6B228 HCDR1

<400> SEQUENCE: 97

Gly Asn Ser Ile Arg Ser Tyr
1               5

<210> SEQ ID NO 98
<211> LENGTH: 5
<212> TYPE: PRT
<213> ORGANISM: Artificial Sequence
<220> FEATURE:
<223> OTHER INFORMATION: CW6B228 HCDR2

<400> SEQUENCE: 98

Tyr Ile Ser Gly Asn
1               5

<210> SEQ ID NO 99
<211> LENGTH: 8
<212> TYPE: PRT
<213> ORGANISM: Artificial Sequence
<220> FEATURE:
<223> OTHER INFORMATION: CW6B228 HCDR3

<400> SEQUENCE: 99

Leu Ser Gly Ile Asp Ala Phe Asp
1               5

```
<210> SEQ ID NO 100
<211> LENGTH: 7
<212> TYPE: PRT
<213> ORGANISM: Artificial Sequence
<220> FEATURE:
<223> OTHER INFORMATION: CW6B229 HCDR1

<400> SEQUENCE: 100

Gly Asn Ser Ile Arg Ser Tyr
1               5

<210> SEQ ID NO 101
<211> LENGTH: 5
<212> TYPE: PRT
<213> ORGANISM: Artificial Sequence
<220> FEATURE:
<223> OTHER INFORMATION: CW6B229 HCDR2

<400> SEQUENCE: 101

Tyr Ile Ser Gly Asn
1               5

<210> SEQ ID NO 102
<211> LENGTH: 8
<212> TYPE: PRT
<213> ORGANISM: Artificial Sequence
<220> FEATURE:
<223> OTHER INFORMATION: CW6B229 HCDR3

<400> SEQUENCE: 102

Leu Ser Gly Ile Asp Ala Phe Asp
1               5

<210> SEQ ID NO 103
<211> LENGTH: 7
<212> TYPE: PRT
<213> ORGANISM: Artificial Sequence
<220> FEATURE:
<223> OTHER INFORMATION: CW6B230 HCDR1

<400> SEQUENCE: 103

Gly Asn Ser Ile Ser Asn Tyr
1               5

<210> SEQ ID NO 104
<211> LENGTH: 5
<212> TYPE: PRT
<213> ORGANISM: Artificial Sequence
<220> FEATURE:
<223> OTHER INFORMATION: CW6B230 HCDR2

<400> SEQUENCE: 104

Tyr Ile Thr Gly Asn
1               5

<210> SEQ ID NO 105
<211> LENGTH: 8
<212> TYPE: PRT
<213> ORGANISM: Artificial Sequence
<220> FEATURE:
<223> OTHER INFORMATION: CW6B230 HCDR3

<400> SEQUENCE: 105

Leu Ser Gly Ile Asp Ala Phe Asp
1               5

<210> SEQ ID NO 106
```

```
<211> LENGTH: 7
<212> TYPE: PRT
<213> ORGANISM: Artificial Sequence
<220> FEATURE:
<223> OTHER INFORMATION: CW6B233 HCDR1

<400> SEQUENCE: 106

Gly Asn Ser Ile Arg Ser Tyr
1               5

<210> SEQ ID NO 107
<211> LENGTH: 5
<212> TYPE: PRT
<213> ORGANISM: Artificial Sequence
<220> FEATURE:
<223> OTHER INFORMATION: CW6B233 HCDR2

<400> SEQUENCE: 107

Tyr Ile Ser Gly Asn
1               5

<210> SEQ ID NO 108
<211> LENGTH: 8
<212> TYPE: PRT
<213> ORGANISM: Artificial Sequence
<220> FEATURE:
<223> OTHER INFORMATION: CW6B233 HCDR3

<400> SEQUENCE: 108

Leu Ser Gly Ile Asp Ala Phe Asp
1               5

<210> SEQ ID NO 109
<211> LENGTH: 9
<212> TYPE: PRT
<213> ORGANISM: Artificial Sequence
<220> FEATURE:
<223> OTHER INFORMATION: CW6B237 HCDR1

<400> SEQUENCE: 109

Gly Phe Ser Leu Ser Asn Ala Arg Met
1               5

<210> SEQ ID NO 110
<211> LENGTH: 5
<212> TYPE: PRT
<213> ORGANISM: Artificial Sequence
<220> FEATURE:
<223> OTHER INFORMATION: CW6B237 HCDR2

<400> SEQUENCE: 110

Phe Ser His Asp Glu
1               5

<210> SEQ ID NO 111
<211> LENGTH: 12
<212> TYPE: PRT
<213> ORGANISM: Artificial Sequence
<220> FEATURE:
<223> OTHER INFORMATION: CW6B237 HCDR3

<400> SEQUENCE: 111

Ile Ile Leu Ser Ser Ser Gly His Asp Ala Phe Asp
1               5                   10

<210> SEQ ID NO 112
<211> LENGTH: 9
```

```
<212> TYPE: PRT
<213> ORGANISM: Artificial Sequence
<220> FEATURE:
<223> OTHER INFORMATION: CW6B238 HCDR1

<400> SEQUENCE: 112

Gly Phe Ser Leu Asn Asn Ala Arg Met
1               5

<210> SEQ ID NO 113
<211> LENGTH: 5
<212> TYPE: PRT
<213> ORGANISM: Artificial Sequence
<220> FEATURE:
<223> OTHER INFORMATION: CW6B238 HCDR2

<400> SEQUENCE: 113

Phe Ser Ser Asp Glu
1               5

<210> SEQ ID NO 114
<211> LENGTH: 12
<212> TYPE: PRT
<213> ORGANISM: Artificial Sequence
<220> FEATURE:
<223> OTHER INFORMATION: CW6B238 HCDR3

<400> SEQUENCE: 114

Ile Ser Leu Tyr Ser Ser Gly His Asp Thr Phe Asp
1               5                   10

<210> SEQ ID NO 115
<211> LENGTH: 7
<212> TYPE: PRT
<213> ORGANISM: Artificial Sequence
<220> FEATURE:
<223> OTHER INFORMATION: CW6B188 HCDR1

<400> SEQUENCE: 115

Gly Phe Thr Phe Thr Asn Tyr
1               5

<210> SEQ ID NO 116
<211> LENGTH: 6
<212> TYPE: PRT
<213> ORGANISM: Artificial Sequence
<220> FEATURE:
<223> OTHER INFORMATION: CW6B188 HCDR2

<400> SEQUENCE: 116

Lys Gln Ser Gly Asn Glu
1               5

<210> SEQ ID NO 117
<211> LENGTH: 11
<212> TYPE: PRT
<213> ORGANISM: Artificial Sequence
<220> FEATURE:
<223> OTHER INFORMATION: CW6B188 HCDR3

<400> SEQUENCE: 117

Thr Leu Tyr Glu Trp Glu Leu Glu Pro Phe Asp
1               5                   10

<210> SEQ ID NO 118
<211> LENGTH: 7
<212> TYPE: PRT
```

```
<213> ORGANISM: Artificial Sequence
<220> FEATURE:
<223> OTHER INFORMATION: CW6B130 LCDR1

<400> SEQUENCE: 118

Asp Asn Ile Gly Ser Glu Ser
1               5

<210> SEQ ID NO 119
<211> LENGTH: 3
<212> TYPE: PRT
<213> ORGANISM: Artificial Sequence
<220> FEATURE:
<223> OTHER INFORMATION: CW6B130 LCDR2

<400> SEQUENCE: 119

Asp Asp Thr
1

<210> SEQ ID NO 120
<211> LENGTH: 8
<212> TYPE: PRT
<213> ORGANISM: Artificial Sequence
<220> FEATURE:
<223> OTHER INFORMATION: CW6B130 LCDR3

<400> SEQUENCE: 120

Trp Asp Ser Ser Ser Asp His Val
1               5

<210> SEQ ID NO 121
<211> LENGTH: 7
<212> TYPE: PRT
<213> ORGANISM: Artificial Sequence
<220> FEATURE:
<223> OTHER INFORMATION: CW6B175 LCDR1

<400> SEQUENCE: 121

Asn Arg Ile Gly Ser Lys Ser
1               5

<210> SEQ ID NO 122
<211> LENGTH: 3
<212> TYPE: PRT
<213> ORGANISM: Artificial Sequence
<220> FEATURE:
<223> OTHER INFORMATION: CW6B175 LCDR2

<400> SEQUENCE: 122

Asp Asp Ser
1

<210> SEQ ID NO 123
<211> LENGTH: 8
<212> TYPE: PRT
<213> ORGANISM: Artificial Sequence
<220> FEATURE:
<223> OTHER INFORMATION: CW6B175 LCDR3

<400> SEQUENCE: 123

Trp Asp Ser Ser Asn Asp His Val
1               5

<210> SEQ ID NO 124
<211> LENGTH: 7
<212> TYPE: PRT
<213> ORGANISM: Artificial Sequence
```

```
<220> FEATURE:
<223> OTHER INFORMATION: CW6B228 LCDR1

<400> SEQUENCE: 124

Ser Gln Asp Ile Asn Asn Tyr
1               5

<210> SEQ ID NO 125
<211> LENGTH: 3
<212> TYPE: PRT
<213> ORGANISM: Artificial Sequence
<220> FEATURE:
<223> OTHER INFORMATION: CW6B228 LCDR2

<400> SEQUENCE: 125

Asp Ala Ser
1

<210> SEQ ID NO 126
<211> LENGTH: 6
<212> TYPE: PRT
<213> ORGANISM: Artificial Sequence
<220> FEATURE:
<223> OTHER INFORMATION: CW6B228 LCDR3

<400> SEQUENCE: 126

Tyr Asp Asp Leu Pro Ile
1               5

<210> SEQ ID NO 127
<211> LENGTH: 7
<212> TYPE: PRT
<213> ORGANISM: Artificial Sequence
<220> FEATURE:
<223> OTHER INFORMATION: CW6B229 LCDR1

<400> SEQUENCE: 127

Ser Gln Asp Ile Ser Asn Tyr
1               5

<210> SEQ ID NO 128
<211> LENGTH: 3
<212> TYPE: PRT
<213> ORGANISM: Artificial Sequence
<220> FEATURE:
<223> OTHER INFORMATION: CW6B229 LCDR2

<400> SEQUENCE: 128

Asp Ala Ser
1

<210> SEQ ID NO 129
<211> LENGTH: 6
<212> TYPE: PRT
<213> ORGANISM: Artificial Sequence
<220> FEATURE:
<223> OTHER INFORMATION: CW6B229 LCDR3

<400> SEQUENCE: 129

Tyr Asp Asn Leu Pro Ile
1               5

<210> SEQ ID NO 130
<211> LENGTH: 7
<212> TYPE: PRT
<213> ORGANISM: Artificial Sequence
<220> FEATURE:
```

```
<223> OTHER INFORMATION: CW6B230 LCDR1

<400> SEQUENCE: 130

Ser Gln Asp Ile Thr Lys Tyr
1               5

<210> SEQ ID NO 131
<211> LENGTH: 3
<212> TYPE: PRT
<213> ORGANISM: Artificial Sequence
<220> FEATURE:
<223> OTHER INFORMATION: CW6B230 LCDR2

<400> SEQUENCE: 131

Asp Ala Ser
1

<210> SEQ ID NO 132
<211> LENGTH: 6
<212> TYPE: PRT
<213> ORGANISM: Artificial Sequence
<220> FEATURE:
<223> OTHER INFORMATION: CW6B230 LCDR3

<400> SEQUENCE: 132

Tyr Asp Asp Leu Pro Ile
1               5

<210> SEQ ID NO 133
<211> LENGTH: 7
<212> TYPE: PRT
<213> ORGANISM: Artificial Sequence
<220> FEATURE:
<223> OTHER INFORMATION: CW6B233 LCDR1

<400> SEQUENCE: 133

Ser Gln Asp Ile Thr Asn Tyr
1               5

<210> SEQ ID NO 134
<211> LENGTH: 3
<212> TYPE: PRT
<213> ORGANISM: Artificial Sequence
<220> FEATURE:
<223> OTHER INFORMATION: CW6B233 LCDR2

<400> SEQUENCE: 134

Asp Ala Ser
1

<210> SEQ ID NO 135
<211> LENGTH: 6
<212> TYPE: PRT
<213> ORGANISM: Artificial Sequence
<220> FEATURE:
<223> OTHER INFORMATION: CW6B233 LCDR3

<400> SEQUENCE: 135

Tyr Asp Asn Leu Pro Ile
1               5

<210> SEQ ID NO 136
<211> LENGTH: 7
<212> TYPE: PRT
<213> ORGANISM: Artificial Sequence
<220> FEATURE:
<223> OTHER INFORMATION: CW6B237 LCDR1
```

```
<400> SEQUENCE: 136

Ser Gln Asp Ile Arg His Asn
1               5

<210> SEQ ID NO 137
<211> LENGTH: 3
<212> TYPE: PRT
<213> ORGANISM: Artificial Sequence
<220> FEATURE:
<223> OTHER INFORMATION: CW6B237 LCDR2

<400> SEQUENCE: 137

Ala Ala Ser
1

<210> SEQ ID NO 138
<211> LENGTH: 6
<212> TYPE: PRT
<213> ORGANISM: Artificial Sequence
<220> FEATURE:
<223> OTHER INFORMATION: CW6B237 LCDR3

<400> SEQUENCE: 138

Asp Tyr Ile Tyr Pro Leu
1               5

<210> SEQ ID NO 139
<211> LENGTH: 7
<212> TYPE: PRT
<213> ORGANISM: Artificial Sequence
<220> FEATURE:
<223> OTHER INFORMATION: CW6B238 LCDR1

<400> SEQUENCE: 139

Ser Gln Asp Ile Arg Asn Thr
1               5

<210> SEQ ID NO 140
<211> LENGTH: 3
<212> TYPE: PRT
<213> ORGANISM: Artificial Sequence
<220> FEATURE:
<223> OTHER INFORMATION: CW6B238 LCDR2

<400> SEQUENCE: 140

Ala Ala Ser
1

<210> SEQ ID NO 141
<211> LENGTH: 6
<212> TYPE: PRT
<213> ORGANISM: Artificial Sequence
<220> FEATURE:
<223> OTHER INFORMATION: CW6B238 LCDR3

<400> SEQUENCE: 141

Asp Tyr Asp Tyr Pro Leu
1               5

<210> SEQ ID NO 142
<211> LENGTH: 7
<212> TYPE: PRT
<213> ORGANISM: Artificial Sequence
<220> FEATURE:
<223> OTHER INFORMATION: CW6B188 LCDR1
```

```
<400> SEQUENCE: 142

Asn Arg Ile Gly Ser Lys Asn
1               5

<210> SEQ ID NO 143
<211> LENGTH: 3
<212> TYPE: PRT
<213> ORGANISM: Artificial Sequence
<220> FEATURE:
<223> OTHER INFORMATION: CW6B188 LCDR2

<400> SEQUENCE: 143

Asp Asp Ser
1

<210> SEQ ID NO 144
<211> LENGTH: 8
<212> TYPE: PRT
<213> ORGANISM: Artificial Sequence
<220> FEATURE:
<223> OTHER INFORMATION: CW6B188 LCDR3

<400> SEQUENCE: 144

Trp Asp Ser Ser Arg Asp His Val
1               5

<210> SEQ ID NO 145
<211> LENGTH: 10
<212> TYPE: PRT
<213> ORGANISM: Artificial Sequence
<220> FEATURE:
<223> OTHER INFORMATION: CW6B130 HCDR1

<400> SEQUENCE: 145

Gly Ala Ser Ile Ser Ser Ile Asn Tyr Tyr
1               5                   10

<210> SEQ ID NO 146
<211> LENGTH: 7
<212> TYPE: PRT
<213> ORGANISM: Artificial Sequence
<220> FEATURE:
<223> OTHER INFORMATION: CW6B130 HCDR2

<400> SEQUENCE: 146

Phe Tyr Tyr Ser Gly Asn Thr
1               5

<210> SEQ ID NO 147
<211> LENGTH: 15
<212> TYPE: PRT
<213> ORGANISM: Artificial Sequence
<220> FEATURE:
<223> OTHER INFORMATION: CW6B130 HCDR3

<400> SEQUENCE: 147

Ala Arg Glu Tyr Tyr Asp Ser Ser Gly Tyr Tyr Pro Phe Glu Pro
1               5                   10                  15

<210> SEQ ID NO 148
<211> LENGTH: 8
<212> TYPE: PRT
<213> ORGANISM: Artificial Sequence
<220> FEATURE:
<223> OTHER INFORMATION: CW6B175 HCDR1

<400> SEQUENCE: 148
```

Gly Phe Thr Phe Thr Asn Tyr Trp
1               5

<210> SEQ ID NO 149
<211> LENGTH: 8
<212> TYPE: PRT
<213> ORGANISM: Artificial Sequence
<220> FEATURE:
<223> OTHER INFORMATION: CW6B175 HCDR2

<400> SEQUENCE: 149

Ile Lys Gln Ser Gly Ser Glu Lys
1               5

<210> SEQ ID NO 150
<211> LENGTH: 14
<212> TYPE: PRT
<213> ORGANISM: Artificial Sequence
<220> FEATURE:
<223> OTHER INFORMATION: CW6B175 HCDR3

<400> SEQUENCE: 150

Ala Arg Thr Leu Tyr Glu Trp Glu Leu Glu Pro Phe Asp Tyr
1               5                   10

<210> SEQ ID NO 151
<211> LENGTH: 8
<212> TYPE: PRT
<213> ORGANISM: Artificial Sequence
<220> FEATURE:
<223> OTHER INFORMATION: CW6B228 HCDR1

<400> SEQUENCE: 151

Gly Asn Ser Ile Arg Ser Tyr Tyr
1               5

<210> SEQ ID NO 152
<211> LENGTH: 7
<212> TYPE: PRT
<213> ORGANISM: Artificial Sequence
<220> FEATURE:
<223> OTHER INFORMATION: CW6B228 HCDR2

<400> SEQUENCE: 152

Ile Tyr Ile Ser Gly Asn Thr
1               5

<210> SEQ ID NO 153
<211> LENGTH: 11
<212> TYPE: PRT
<213> ORGANISM: Artificial Sequence
<220> FEATURE:
<223> OTHER INFORMATION: CW6B228 HCDR3

<400> SEQUENCE: 153

Ala Arg Leu Ser Gly Ile Asp Ala Phe Asp Ile
1               5                   10

<210> SEQ ID NO 154
<211> LENGTH: 8
<212> TYPE: PRT
<213> ORGANISM: Artificial Sequence
<220> FEATURE:
<223> OTHER INFORMATION: CW6B229 HCDR1

<400> SEQUENCE: 154

Gly Asn Ser Ile Arg Ser Tyr Tyr
1               5

<210> SEQ ID NO 155
<211> LENGTH: 7
<212> TYPE: PRT
<213> ORGANISM: Artificial Sequence
<220> FEATURE:
<223> OTHER INFORMATION: CW6B229 HCDR2

<400> SEQUENCE: 155

Ile Tyr Ile Ser Gly Asn Thr
1               5

<210> SEQ ID NO 156
<211> LENGTH: 11
<212> TYPE: PRT
<213> ORGANISM: Artificial Sequence
<220> FEATURE:
<223> OTHER INFORMATION: CW6B229 HCDR3

<400> SEQUENCE: 156

Ala Arg Leu Ser Gly Ile Asp Ala Phe Asp Ile
1               5                   10

<210> SEQ ID NO 157
<211> LENGTH: 8
<212> TYPE: PRT
<213> ORGANISM: Artificial Sequence
<220> FEATURE:
<223> OTHER INFORMATION: CW6B230 HCDR1

<400> SEQUENCE: 157

Gly Asn Ser Ile Ser Asn Tyr Tyr
1               5

<210> SEQ ID NO 158
<211> LENGTH: 7
<212> TYPE: PRT
<213> ORGANISM: Artificial Sequence
<220> FEATURE:
<223> OTHER INFORMATION: CW6B230 HCDR2

<400> SEQUENCE: 158

Ile Tyr Ile Thr Gly Asn Thr
1               5

<210> SEQ ID NO 159
<211> LENGTH: 11
<212> TYPE: PRT
<213> ORGANISM: Artificial Sequence
<220> FEATURE:
<223> OTHER INFORMATION: CW6B230 HCDR3

<400> SEQUENCE: 159

Ala Arg Leu Ser Gly Ile Asp Ala Phe Asp Ile
1               5                   10

<210> SEQ ID NO 160
<211> LENGTH: 8
<212> TYPE: PRT
<213> ORGANISM: Artificial Sequence
<220> FEATURE:
<223> OTHER INFORMATION: CW6B233 HCDR1

<400> SEQUENCE: 160

Gly Asn Ser Ile Arg Ser Tyr Tyr

```
1               5
```

<210> SEQ ID NO 161
<211> LENGTH: 7
<212> TYPE: PRT
<213> ORGANISM: Artificial Sequence
<220> FEATURE:
<223> OTHER INFORMATION: CW6B233 HCDR2

<400> SEQUENCE: 161

```
Ile Tyr Ile Ser Gly Asn Thr
1               5
```

<210> SEQ ID NO 162
<211> LENGTH: 11
<212> TYPE: PRT
<213> ORGANISM: Artificial Sequence
<220> FEATURE:
<223> OTHER INFORMATION: CW6B233 HCDR3

<400> SEQUENCE: 162

```
Ala Arg Leu Ser Gly Ile Asp Ala Phe Asp Ile
1               5                   10
```

<210> SEQ ID NO 163
<211> LENGTH: 10
<212> TYPE: PRT
<213> ORGANISM: Artificial Sequence
<220> FEATURE:
<223> OTHER INFORMATION: CW6B237 HCDR1

<400> SEQUENCE: 163

```
Gly Phe Ser Leu Ser Asn Ala Arg Met Gly
1               5                   10
```

<210> SEQ ID NO 164
<211> LENGTH: 7
<212> TYPE: PRT
<213> ORGANISM: Artificial Sequence
<220> FEATURE:
<223> OTHER INFORMATION: CW6B237 HCDR2

<400> SEQUENCE: 164

```
Ile Phe Ser His Asp Glu Lys
1               5
```

<210> SEQ ID NO 165
<211> LENGTH: 15
<212> TYPE: PRT
<213> ORGANISM: Artificial Sequence
<220> FEATURE:
<223> OTHER INFORMATION: CW6B237 HCDR3

<400> SEQUENCE: 165

```
Ala Arg Ile Ile Leu Ser Ser Ser Gly His Asp Ala Phe Asp Ile
1               5                   10                  15
```

<210> SEQ ID NO 166
<211> LENGTH: 10
<212> TYPE: PRT
<213> ORGANISM: Artificial Sequence
<220> FEATURE:
<223> OTHER INFORMATION: CW6B238 HCDR1

<400> SEQUENCE: 166

```
Gly Phe Ser Leu Asn Asn Ala Arg Met Gly
1               5                   10
```

<210> SEQ ID NO 167
<211> LENGTH: 7
<212> TYPE: PRT
<213> ORGANISM: Artificial Sequence
<220> FEATURE:
<223> OTHER INFORMATION: CW6B238 HCDR2

<400> SEQUENCE: 167

Met Phe Ser Ser Asp Glu Lys
1               5

<210> SEQ ID NO 168
<211> LENGTH: 15
<212> TYPE: PRT
<213> ORGANISM: Artificial Sequence
<220> FEATURE:
<223> OTHER INFORMATION: CW6B238 HCDR3

<400> SEQUENCE: 168

Ala Arg Ile Ser Leu Tyr Ser Ser Gly His Asp Thr Phe Asp Leu
1               5                   10                  15

<210> SEQ ID NO 169
<211> LENGTH: 8
<212> TYPE: PRT
<213> ORGANISM: Artificial Sequence
<220> FEATURE:
<223> OTHER INFORMATION: CW6B188 HCDR1

<400> SEQUENCE: 169

Gly Phe Thr Phe Thr Asn Tyr Trp
1               5

<210> SEQ ID NO 170
<211> LENGTH: 8
<212> TYPE: PRT
<213> ORGANISM: Artificial Sequence
<220> FEATURE:
<223> OTHER INFORMATION: CW6B188 HCDR2

<400> SEQUENCE: 170

Ile Lys Gln Ser Gly Asn Glu Lys
1               5

<210> SEQ ID NO 171
<211> LENGTH: 14
<212> TYPE: PRT
<213> ORGANISM: Artificial Sequence
<220> FEATURE:
<223> OTHER INFORMATION: CW6B188 HCDR3

<400> SEQUENCE: 171

Ala Arg Thr Leu Tyr Glu Trp Glu Leu Glu Pro Phe Asp Tyr
1               5                   10

<210> SEQ ID NO 172
<211> LENGTH: 6
<212> TYPE: PRT
<213> ORGANISM: Artificial Sequence
<220> FEATURE:
<223> OTHER INFORMATION: CW6B130 LCDR1

<400> SEQUENCE: 172

Asn Ile Gly Ser Glu Ser
1               5

```
<210> SEQ ID NO 173
<211> LENGTH: 3
<212> TYPE: PRT
<213> ORGANISM: Artificial Sequence
<220> FEATURE:
<223> OTHER INFORMATION: CW6B130 LCDR2

<400> SEQUENCE: 173

Asp Asp Thr
1

<210> SEQ ID NO 174
<211> LENGTH: 11
<212> TYPE: PRT
<213> ORGANISM: Artificial Sequence
<220> FEATURE:
<223> OTHER INFORMATION: CW6B130 LCDR3

<400> SEQUENCE: 174

Gln Val Trp Asp Ser Ser Ser Asp His Val Val
1               5                   10

<210> SEQ ID NO 175
<211> LENGTH: 6
<212> TYPE: PRT
<213> ORGANISM: Artificial Sequence
<220> FEATURE:
<223> OTHER INFORMATION: CW6B175 LCDR1

<400> SEQUENCE: 175

Arg Ile Gly Ser Lys Ser
1               5

<210> SEQ ID NO 176
<211> LENGTH: 3
<212> TYPE: PRT
<213> ORGANISM: Artificial Sequence
<220> FEATURE:
<223> OTHER INFORMATION: CW6B175 LCDR2

<400> SEQUENCE: 176

Asp Asp Ser
1

<210> SEQ ID NO 177
<211> LENGTH: 11
<212> TYPE: PRT
<213> ORGANISM: Artificial Sequence
<220> FEATURE:
<223> OTHER INFORMATION: CW6B175 LCDR3

<400> SEQUENCE: 177

Gln Val Trp Asp Ser Ser Asn Asp His Val Val
1               5                   10

<210> SEQ ID NO 178
<211> LENGTH: 6
<212> TYPE: PRT
<213> ORGANISM: Artificial Sequence
<220> FEATURE:
<223> OTHER INFORMATION: CW6B228 LCDR1

<400> SEQUENCE: 178

Gln Asp Ile Asn Asn Tyr
1               5
```

```
<210> SEQ ID NO 179
<211> LENGTH: 3
<212> TYPE: PRT
<213> ORGANISM: Artificial Sequence
<220> FEATURE:
<223> OTHER INFORMATION: CW6B228 LCDR2

<400> SEQUENCE: 179

Asp Ala Ser
1

<210> SEQ ID NO 180
<211> LENGTH: 9
<212> TYPE: PRT
<213> ORGANISM: Artificial Sequence
<220> FEATURE:
<223> OTHER INFORMATION: CW6B228 LCDR3

<400> SEQUENCE: 180

Gln Gln Tyr Asp Asp Leu Pro Ile Thr
1               5

<210> SEQ ID NO 181
<211> LENGTH: 6
<212> TYPE: PRT
<213> ORGANISM: Artificial Sequence
<220> FEATURE:
<223> OTHER INFORMATION: CW6B229 LCDR1

<400> SEQUENCE: 181

Gln Asp Ile Ser Asn Tyr
1               5

<210> SEQ ID NO 182
<211> LENGTH: 3
<212> TYPE: PRT
<213> ORGANISM: Artificial Sequence
<220> FEATURE:
<223> OTHER INFORMATION: CW6B229 LCDR2

<400> SEQUENCE: 182

Asp Ala Ser
1

<210> SEQ ID NO 183
<211> LENGTH: 9
<212> TYPE: PRT
<213> ORGANISM: Artificial Sequence
<220> FEATURE:
<223> OTHER INFORMATION: CW6B229 LCDR3

<400> SEQUENCE: 183

Gln Gln Tyr Asp Asn Leu Pro Ile Thr
1               5

<210> SEQ ID NO 184
<211> LENGTH: 6
<212> TYPE: PRT
<213> ORGANISM: Artificial Sequence
<220> FEATURE:
<223> OTHER INFORMATION: CW6B230 LCDR1

<400> SEQUENCE: 184

Gln Asp Ile Thr Lys Tyr
1               5

<210> SEQ ID NO 185
```

```
<211> LENGTH: 3
<212> TYPE: PRT
<213> ORGANISM: Artificial Sequence
<220> FEATURE:
<223> OTHER INFORMATION: CW6B230 LCDR2

<400> SEQUENCE: 185

Asp Ala Ser
1

<210> SEQ ID NO 186
<211> LENGTH: 9
<212> TYPE: PRT
<213> ORGANISM: Artificial Sequence
<220> FEATURE:
<223> OTHER INFORMATION: CW6B230 LCDR3

<400> SEQUENCE: 186

Gln Gln Tyr Asp Asp Leu Pro Ile Thr
1               5

<210> SEQ ID NO 187
<211> LENGTH: 6
<212> TYPE: PRT
<213> ORGANISM: Artificial Sequence
<220> FEATURE:
<223> OTHER INFORMATION: CW6B233 LCDR1

<400> SEQUENCE: 187

Gln Asp Ile Thr Asn Tyr
1               5

<210> SEQ ID NO 188
<211> LENGTH: 3
<212> TYPE: PRT
<213> ORGANISM: Artificial Sequence
<220> FEATURE:
<223> OTHER INFORMATION: CW6B233 LCDR2

<400> SEQUENCE: 188

Asp Ala Ser
1

<210> SEQ ID NO 189
<211> LENGTH: 9
<212> TYPE: PRT
<213> ORGANISM: Artificial Sequence
<220> FEATURE:
<223> OTHER INFORMATION: CW6B233 LCDR3

<400> SEQUENCE: 189

Gln Gln Tyr Asp Asn Leu Pro Ile Thr
1               5

<210> SEQ ID NO 190
<211> LENGTH: 6
<212> TYPE: PRT
<213> ORGANISM: Artificial Sequence
<220> FEATURE:
<223> OTHER INFORMATION: CW6B237 LCDR1

<400> SEQUENCE: 190

Gln Asp Ile Arg His Asn
1               5

<210> SEQ ID NO 191
<211> LENGTH: 3
```

```
<212> TYPE: PRT
<213> ORGANISM: Artificial Sequence
<220> FEATURE:
<223> OTHER INFORMATION: CW6B237 LCDR2

<400> SEQUENCE: 191

Ala Ala Ser
1

<210> SEQ ID NO 192
<211> LENGTH: 9
<212> TYPE: PRT
<213> ORGANISM: Artificial Sequence
<220> FEATURE:
<223> OTHER INFORMATION: CW6B237 LCDR3

<400> SEQUENCE: 192

Leu Gln Asp Tyr Ile Tyr Pro Leu Thr
1               5

<210> SEQ ID NO 193
<211> LENGTH: 6
<212> TYPE: PRT
<213> ORGANISM: Artificial Sequence
<220> FEATURE:
<223> OTHER INFORMATION: CW6B238 LCDR1

<400> SEQUENCE: 193

Gln Asp Ile Arg Asn Thr
1               5

<210> SEQ ID NO 194
<211> LENGTH: 3
<212> TYPE: PRT
<213> ORGANISM: Artificial Sequence
<220> FEATURE:
<223> OTHER INFORMATION: CW6B238 LCDR2

<400> SEQUENCE: 194

Ala Ala Ser
1

<210> SEQ ID NO 195
<211> LENGTH: 9
<212> TYPE: PRT
<213> ORGANISM: Artificial Sequence
<220> FEATURE:
<223> OTHER INFORMATION: CW6B238 LCDR3

<400> SEQUENCE: 195

Leu Gln Asp Tyr Asp Tyr Pro Leu Thr
1               5

<210> SEQ ID NO 196
<211> LENGTH: 7
<212> TYPE: PRT
<213> ORGANISM: Artificial Sequence
<220> FEATURE:
<223> OTHER INFORMATION: CW6B188 LCDR1

<400> SEQUENCE: 196

Asn Arg Ile Gly Ser Lys Asn
1               5

<210> SEQ ID NO 197
<211> LENGTH: 3
<212> TYPE: PRT
```

<213> ORGANISM: Artificial Sequence
<220> FEATURE:
<223> OTHER INFORMATION: CW6B188 LCDR2

<400> SEQUENCE: 197

Asp Asp Ser
1

<210> SEQ ID NO 198
<211> LENGTH: 8
<212> TYPE: PRT
<213> ORGANISM: Artificial Sequence
<220> FEATURE:
<223> OTHER INFORMATION: CW6B188 LCDR3

<400> SEQUENCE: 198

Trp Asp Ser Ser Arg Asp His Val
1               5

<210> SEQ ID NO 199
<211> LENGTH: 450
<212> TYPE: PRT
<213> ORGANISM: Artificial Sequence
<220> FEATURE:
<223> OTHER INFORMATION: rhHLA-A2

<400> SEQUENCE: 199

Phe Leu Leu Pro Thr Gly Ala Glu Ala Gly Gly Gly Ser Gly Gly
1               5                   10                  15

Gly Gly Ser Gly Gly Gly Gly Ser Ile Gln Arg Thr Pro Lys Ile Gln
                20                  25                  30

Val Tyr Ser Arg His Pro Ala Glu Asn Gly Lys Ser Asn Phe Leu Asn
            35                  40                  45

Cys Tyr Val Ser Gly Phe His Pro Ser Asp Ile Glu Val Asp Leu Leu
        50                  55                  60

Lys Asn Gly Glu Arg Ile Glu Lys Val Glu His Ser Asp Leu Ser Phe
65                  70                  75                  80

Ser Lys Asp Trp Ser Phe Tyr Leu Leu Tyr Tyr Thr Glu Phe Thr Pro
                85                  90                  95

Thr Glu Lys Asp Glu Tyr Ala Cys Arg Val Asn His Val Thr Leu Ser
            100                 105                 110

Gln Pro Lys Ile Val Lys Trp Asp Arg Asp Met Gly Gly Gly Ser
        115                 120                 125

Gly Gly Gly Gly Ser Gly Gly Gly Ser Gly Ser His Ser Met Arg
    130                 135                 140

Tyr Phe Phe Thr Ser Val Ser Arg Pro Gly Arg Gly Glu Pro Arg Phe
145                 150                 155                 160

Ile Ala Val Gly Tyr Val Asp Asp Thr Gln Phe Val Arg Phe Asp Ser
                165                 170                 175

Asp Ala Ala Ser Gln Arg Met Glu Pro Arg Ala Pro Trp Ile Glu Gln
            180                 185                 190

Glu Gly Pro Glu Tyr Trp Asp Gly Glu Thr Arg Lys Val Lys Ala His
        195                 200                 205

Ser Gln Thr His Arg Val Asp Leu Gly Thr Leu Arg Gly Tyr Tyr Asn
    210                 215                 220

Gln Ser Glu Ala Gly Ser His Thr Val Gln Arg Met Tyr Gly Cys Asp
225                 230                 235                 240

Val Gly Ser Asp Trp Arg Phe Leu Arg Gly Tyr His Gln Tyr Ala Tyr
                245                 250                 255

```
Asp Gly Lys Asp Tyr Ile Ala Leu Lys Glu Asp Leu Arg Ser Trp Thr
            260                 265                 270

Ala Ala Asp Met Ala Ala Gln Thr Thr Lys His Lys Trp Glu Ala Ala
        275                 280                 285

His Val Ala Glu Gln Leu Arg Ala Tyr Leu Glu Gly Thr Cys Val Glu
    290                 295                 300

Trp Leu Arg Arg Tyr Leu Glu Asn Gly Lys Glu Thr Leu Gln Arg Thr
305                 310                 315                 320

Asp Ala Pro Lys Thr His Met Thr His His Ala Val Ser Asp His Glu
                325                 330                 335

Ala Thr Leu Arg Cys Trp Ala Leu Ser Phe Tyr Pro Ala Glu Ile Thr
            340                 345                 350

Leu Thr Trp Gln Arg Asp Gly Glu Asp Gln Thr Gln Asp Thr Glu Leu
        355                 360                 365

Val Glu Thr Arg Pro Ala Gly Asp Gly Thr Phe Gln Lys Trp Ala Ala
370                 375                 380

Val Val Val Pro Ser Gly Gln Glu Gln Arg Tyr Thr Cys His Val Gln
385                 390                 395                 400

His Glu Gly Leu Pro Lys Pro Leu Thr Leu Arg Trp Glu Pro Ser Ser
                405                 410                 415

Gln Pro Thr Ile Pro Ile Gly Gly Gly Ser His His His His His His
            420                 425                 430

His Gly Ser Gly Leu Asn Asp Ile Phe Glu Ala Gln Lys Ile Glu Trp
        435                 440                 445

His Glu
    450

<210> SEQ ID NO 200
<211> LENGTH: 456
<212> TYPE: PRT
<213> ORGANISM: Artificial Sequence
<220> FEATURE:
<223> OTHER INFORMATION: rhHLA-G5

<400> SEQUENCE: 200

Arg Ile Ile Pro Arg His Leu Gln Leu Gly Gly Gly Ser Gly Gly
1               5                   10                  15

Gly Gly Ser Ile Gln Arg Thr Pro Lys Ile Gln Val Tyr Ser Arg His
            20                  25                  30

Pro Ala Glu Asn Gly Lys Ser Asn Phe Leu Asn Cys Tyr Val Ser Gly
        35                  40                  45

Phe His Pro Ser Asp Ile Glu Val Asp Leu Leu Lys Asn Gly Glu Arg
    50                  55                  60

Ile Glu Lys Val Glu His Ser Asp Leu Ser Phe Ser Lys Asp Trp Ser
65                  70                  75                  80

Phe Tyr Leu Leu Tyr Tyr Thr Glu Phe Thr Pro Thr Glu Lys Asp Glu
                85                  90                  95

Tyr Ala Cys Arg Val Asn His Val Thr Leu Ser Gln Pro Lys Ile Val
            100                 105                 110

Lys Trp Asp Arg Asp Met Gly Gly Gly Ser Gly Gly Gly Gly Ser
        115                 120                 125

Gly Gly Gly Gly Ser Gly Ser His Ser Met Arg Tyr Phe Ser Ala Ala
    130                 135                 140

Val Ser Arg Pro Gly Arg Gly Glu Pro Arg Phe Ile Ala Met Gly Tyr
145                 150                 155                 160
```

-continued

```
Val Asp Asp Thr Gln Phe Val Arg Phe Asp Ser Asp Ser Ala Ser Pro
                165                 170                 175

Arg Met Glu Pro Arg Ala Pro Trp Val Glu Gln Glu Gly Pro Glu Tyr
            180                 185                 190

Trp Glu Glu Glu Thr Arg Asn Thr Lys Ala His Ala Gln Thr Asp Arg
        195                 200                 205

Met Asn Leu Gln Thr Leu Arg Gly Tyr Tyr Asn Gln Ser Glu Ala Ser
    210                 215                 220

Ser His Thr Leu Gln Trp Met Ile Gly Cys Asp Leu Gly Ser Asp Gly
225                 230                 235                 240

Arg Leu Leu Arg Gly Tyr Glu Gln Tyr Ala Tyr Asp Gly Lys Asp Tyr
                245                 250                 255

Leu Ala Leu Asn Glu Asp Leu Arg Ser Trp Thr Ala Ala Asp Thr Ala
            260                 265                 270

Ala Gln Ile Ser Lys Arg Lys Cys Glu Ala Ala Asn Val Ala Glu Gln
        275                 280                 285

Arg Arg Ala Tyr Leu Glu Gly Thr Cys Val Glu Trp Leu His Arg Tyr
    290                 295                 300

Leu Glu Asn Gly Lys Glu Met Leu Gln Arg Ala Asp Pro Pro Lys Thr
305                 310                 315                 320

His Val Thr His His Pro Val Phe Asp Tyr Glu Ala Thr Leu Arg Cys
                325                 330                 335

Trp Ala Leu Gly Phe Tyr Pro Ala Glu Ile Ile Leu Thr Trp Gln Arg
            340                 345                 350

Asp Gly Glu Asp Gln Thr Gln Asp Val Glu Leu Val Glu Thr Arg Pro
        355                 360                 365

Ala Gly Asp Gly Thr Phe Gln Lys Trp Ala Ala Val Val Val Pro Ser
    370                 375                 380

Gly Glu Glu Gln Arg Tyr Thr Cys His Val Gln His Glu Gly Leu Pro
385                 390                 395                 400

Glu Pro Leu Met Leu Arg Trp Ser Lys Glu Gly Asp Gly Gly Ile Met
                405                 410                 415

Ser Val Arg Glu Ser Arg Ser Leu Ser Glu Asp Leu Gly Gly Gly
            420                 425                 430

Ser His His His His His Gly Ser Gly Leu Asn Asp Ile Phe Glu
        435                 440                 445

Ala Gln Lys Ile Glu Trp His Glu
450                 455

<210> SEQ ID NO 201
<211> LENGTH: 100
<212> TYPE: PRT
<213> ORGANISM: Artificial Sequence
<220> FEATURE:
<223> OTHER INFORMATION: beta2-microglobulin

<400> SEQUENCE: 201

Met Ile Gln Arg Thr Pro Lys Ile Gln Val Tyr Ser Arg His Pro Ala
1               5                   10                  15

Glu Asn Gly Lys Ser Asn Phe Leu Asn Cys Tyr Val Ser Gly Phe His
            20                  25                  30

Pro Ser Asp Ile Glu Val Asp Leu Leu Lys Asn Gly Glu Arg Ile Glu
        35                  40                  45

Lys Val Glu His Ser Asp Leu Ser Phe Ser Lys Asp Trp Ser Phe Tyr
    50                  55                  60
```

Leu Leu Tyr Tyr Thr Glu Phe Thr Pro Thr Glu Lys Asp Glu Tyr Ala
 65                  70                  75                  80

Cys Arg Val Asn His Val Thr Leu Ser Gln Pro Lys Ile Val Lys Trp
                 85                  90                  95

Asp Arg Asp Met
            100

<210> SEQ ID NO 202
<211> LENGTH: 450
<212> TYPE: PRT
<213> ORGANISM: Artificial Sequence
<220> FEATURE:
<223> OTHER INFORMATION: CW6W32 (rhHLA-Cw6/TRAT)

<400> SEQUENCE: 202

Thr Arg Ala Thr Lys Met Gln Val Ile Gly Gly Gly Ser Gly Gly
 1               5                  10                  15

Gly Gly Ser Gly Gly Gly Gly Ser Ile Gln Arg Thr Pro Lys Ile Gln
                 20                  25                  30

Val Tyr Ser Arg His Pro Ala Glu Asn Gly Lys Ser Asn Phe Leu Asn
                 35                  40                  45

Cys Tyr Val Ser Gly Phe His Pro Ser Asp Ile Glu Val Asp Leu Leu
             50                  55                  60

Lys Asn Gly Glu Arg Ile Glu Lys Val Glu His Ser Asp Leu Ser Phe
 65                  70                  75                  80

Ser Lys Asp Trp Ser Phe Tyr Leu Leu Tyr Tyr Thr Glu Phe Thr Pro
                 85                  90                  95

Thr Glu Lys Asp Glu Tyr Ala Cys Arg Val Asn His Val Thr Leu Ser
            100                 105                 110

Gln Pro Lys Ile Val Lys Trp Asp Arg Asp Met Gly Gly Gly Gly Ser
        115                 120                 125

Gly Gly Gly Gly Ser Gly Gly Gly Ser Ser His Ser Met Arg
        130                 135                 140

Tyr Phe Asp Thr Ala Val Ser Arg Pro Gly Arg Gly Glu Pro Arg Phe
145                 150                 155                 160

Ile Ser Val Gly Tyr Val Asp Asp Thr Gln Phe Val Arg Phe Asp Ser
                165                 170                 175

Asp Ala Ala Ser Pro Arg Gly Glu Pro Arg Ala Pro Trp Val Glu Gln
            180                 185                 190

Glu Gly Pro Glu Tyr Trp Asp Arg Glu Thr Gln Lys Tyr Lys Arg Gln
        195                 200                 205

Ala Gln Ala Asp Arg Val Asn Leu Arg Lys Leu Arg Gly Tyr Tyr Asn
    210                 215                 220

Gln Ser Glu Asp Gly Ser His Thr Leu Gln Trp Met Tyr Gly Cys Asp
225                 230                 235                 240

Leu Gly Pro Asp Gly Arg Leu Leu Arg Gly Tyr Asp Gln Ser Ala Tyr
                245                 250                 255

Asp Gly Lys Asp Tyr Ile Ala Leu Asn Glu Asp Leu Arg Ser Trp Thr
            260                 265                 270

Ala Ala Asp Thr Ala Ala Gln Ile Thr Gln Arg Lys Trp Glu Ala Ala
        275                 280                 285

Arg Glu Ala Glu Gln Trp Arg Ala Tyr Leu Glu Gly Thr Cys Val Glu
    290                 295                 300

Trp Leu Arg Arg Tyr Leu Glu Asn Gly Lys Glu Thr Leu Gln Arg Ala
305                 310                 315                 320

```
Glu His Pro Lys Thr His Val Thr His His Pro Val Ser Asp His Glu
                325                 330                 335

Ala Thr Leu Arg Cys Trp Ala Leu Gly Phe Tyr Pro Ala Glu Ile Thr
                340                 345                 350

Leu Thr Trp Gln Arg Asp Gly Glu Asp Gln Thr Gln Asp Thr Glu Leu
                355                 360                 365

Val Glu Thr Arg Pro Ala Gly Asp Gly Thr Phe Gln Lys Trp Ala Ala
                370                 375                 380

Val Val Val Pro Ser Gly Glu Glu Gln Arg Tyr Thr Cys His Val Gln
385                 390                 395                 400

His Glu Gly Leu Pro Glu Pro Leu Thr Leu Arg Trp Glu Pro Ser Ser
                405                 410                 415

Gln Pro Thr Ile Pro Ile Gly Gly Gly Ser His His His His
                420                 425                 430

His Gly Ser Gly Leu Asn Asp Ile Phe Glu Ala Gln Lys Ile Glu Trp
                435                 440                 445

His Glu
    450

<210> SEQ ID NO 203
<211> LENGTH: 427
<212> TYPE: PRT
<213> ORGANISM: Artificial Sequence
<220> FEATURE:
<223> OTHER INFORMATION: CW6W3.ECO.PP.002/.003 (rhHLA-Cw6/ARF)

<400> SEQUENCE: 203

Met Ile Gln Arg Thr Pro Lys Ile Gln Val Tyr Ser Arg His Pro Ala
1               5                   10                  15

Glu Asn Gly Lys Ser Asn Phe Leu Asn Cys Tyr Val Ser Gly Phe His
                20                  25                  30

Pro Ser Asp Ile Glu Val Asp Leu Leu Lys Asn Gly Glu Arg Ile Glu
            35                  40                  45

Lys Val Glu His Ser Asp Leu Ser Phe Ser Lys Asp Trp Ser Phe Tyr
50                  55                  60

Leu Leu Tyr Tyr Thr Glu Phe Thr Pro Thr Glu Lys Asp Glu Tyr Ala
65                  70                  75                  80

Cys Arg Val Asn His Val Thr Leu Ser Gln Pro Lys Ile Val Lys Trp
                85                  90                  95

Asp Arg Asp Met Gly Gly Gly Gly Ser Gly Gly Gly Gly Ser Gly Gly
                100                 105                 110

Gly Gly Ser Gly Ser His Ser Met Arg Tyr Phe Asp Thr Ala Val Ser
            115                 120                 125

Arg Pro Gly Arg Gly Glu Pro Arg Phe Ile Ser Val Gly Tyr Val Asp
        130                 135                 140

Asp Thr Gln Phe Val Arg Phe Asp Ser Asp Ala Ala Ser Pro Arg Gly
145                 150                 155                 160

Glu Pro Arg Ala Pro Trp Val Glu Gln Glu Gly Pro Glu Tyr Trp Asp
                165                 170                 175

Arg Glu Thr Gln Lys Tyr Lys Arg Gln Ala Gln Ala Asp Arg Val Asn
                180                 185                 190

Leu Arg Lys Leu Arg Gly Tyr Tyr Asn Gln Ser Glu Asp Gly Ser His
            195                 200                 205

Thr Leu Gln Trp Met Tyr Gly Cys Asp Leu Gly Pro Asp Gly Arg Leu
210                 215                 220
```

-continued

```
Leu Arg Gly Tyr Asp Gln Ser Ala Tyr Asp Gly Lys Asp Tyr Ile Ala
225                 230                 235                 240

Leu Asn Glu Asp Leu Arg Ser Trp Thr Ala Asp Thr Ala Ala Gln
            245                 250                 255

Ile Thr Gln Arg Lys Trp Glu Ala Ala Arg Glu Ala Glu Gln Trp Arg
        260                 265                 270

Ala Tyr Leu Glu Gly Thr Cys Val Glu Trp Leu Arg Arg Tyr Leu Glu
        275                 280                 285

Asn Gly Lys Glu Thr Leu Gln Arg Ala Glu His Pro Lys Thr His Val
    290                 295                 300

Thr His His Pro Val Ser Asp His Glu Ala Thr Leu Arg Cys Trp Ala
305                 310                 315                 320

Leu Gly Phe Tyr Pro Ala Glu Ile Thr Leu Thr Trp Gln Arg Asp Gly
                325                 330                 335

Glu Asp Gln Thr Gln Asp Thr Glu Leu Val Glu Thr Arg Pro Ala Gly
            340                 345                 350

Asp Gly Thr Phe Gln Lys Trp Ala Ala Val Val Val Pro Ser Gly Glu
        355                 360                 365

Glu Gln Arg Tyr Thr Cys His Val Gln His Glu Gly Leu Pro Glu Pro
    370                 375                 380

Leu Thr Leu Arg Trp Glu Pro Ser Ser Gln Pro Thr Ile Pro Ile Gly
385                 390                 395                 400

Gly Gly Gly Ser His His His His His Gly Ser Gly Leu Asn Asp
                405                 410                 415

Ile Phe Glu Ala Gln Lys Ile Glu Trp His Glu
                420                 425

<210> SEQ ID NO 204
<211> LENGTH: 450
<212> TYPE: PRT
<213> ORGANISM: Artificial Sequence
<220> FEATURE:
<223> OTHER INFORMATION: CW6W36 (rHLA-Cw6/ADAMTSL5)

<400> SEQUENCE: 204

Val Arg Ser Arg Arg Val Leu Arg Leu Gly Gly Gly Ser Gly Gly
1               5                   10                  15

Gly Gly Ser Gly Gly Gly Ser Ile Gln Arg Thr Pro Lys Ile Gln
            20                  25                  30

Val Tyr Ser Arg His Pro Ala Glu Asn Gly Lys Ser Asn Phe Leu Asn
        35                  40                  45

Cys Tyr Val Ser Gly Phe His Pro Ser Asp Ile Glu Val Asp Leu Leu
    50                  55                  60

Lys Asn Gly Glu Arg Ile Glu Lys Val Glu His Ser Asp Leu Ser Phe
65                  70                  75                  80

Ser Lys Asp Trp Ser Phe Tyr Leu Leu Tyr Tyr Thr Glu Phe Thr Pro
                85                  90                  95

Thr Glu Lys Asp Glu Tyr Ala Cys Arg Val Asn His Val Thr Leu Ser
            100                 105                 110

Gln Pro Lys Ile Val Lys Trp Asp Arg Asp Met Gly Gly Gly Ser
        115                 120                 125

Gly Gly Gly Gly Ser Gly Gly Gly Ser Gly Ser His Ser Met Arg
    130                 135                 140

Tyr Phe Asp Thr Ala Val Ser Arg Pro Gly Arg Gly Glu Pro Arg Phe
145                 150                 155                 160
```

```
Ile Ser Val Gly Tyr Val Asp Asp Thr Gln Phe Val Arg Phe Asp Ser
            165                 170                 175

Asp Ala Ala Ser Pro Arg Gly Glu Pro Arg Ala Pro Trp Val Glu Gln
        180                 185                 190

Glu Gly Pro Glu Tyr Trp Asp Arg Glu Thr Gln Lys Tyr Lys Arg Gln
            195                 200                 205

Ala Gln Ala Asp Arg Val Asn Leu Arg Lys Leu Arg Gly Tyr Tyr Asn
        210                 215                 220

Gln Ser Glu Asp Gly Ser His Thr Leu Gln Trp Met Tyr Gly Cys Asp
225                 230                 235                 240

Leu Gly Pro Asp Gly Arg Leu Leu Arg Gly Tyr Asp Gln Ser Ala Tyr
            245                 250                 255

Asp Gly Lys Asp Tyr Ile Ala Leu Asn Glu Asp Leu Arg Ser Trp Thr
        260                 265                 270

Ala Ala Asp Thr Ala Ala Gln Ile Thr Gln Arg Lys Trp Glu Ala Ala
    275                 280                 285

Arg Glu Ala Glu Gln Trp Arg Ala Tyr Leu Glu Gly Thr Cys Val Glu
    290                 295                 300

Trp Leu Arg Arg Tyr Leu Glu Asn Gly Lys Glu Thr Leu Gln Arg Ala
305                 310                 315                 320

Glu His Pro Lys Thr His Val Thr His His Pro Val Ser Asp His Glu
            325                 330                 335

Ala Thr Leu Arg Cys Trp Ala Leu Gly Phe Tyr Pro Ala Glu Ile Thr
        340                 345                 350

Leu Thr Trp Gln Arg Asp Gly Glu Asp Gln Thr Gln Asp Thr Glu Leu
    355                 360                 365

Val Glu Thr Arg Pro Ala Gly Asp Gly Thr Phe Gln Lys Trp Ala Ala
    370                 375                 380

Val Val Val Pro Ser Gly Glu Glu Gln Arg Tyr Thr Cys His Val Gln
385                 390                 395                 400

His Glu Gly Leu Pro Glu Pro Leu Thr Leu Arg Trp Glu Pro Ser Ser
            405                 410                 415

Gln Pro Thr Ile Pro Ile Gly Gly Gly Ser His His His His
        420                 425                 430

His Gly Ser Gly Leu Asn Asp Ile Phe Glu Ala Gln Lys Ile Glu Trp
    435                 440                 445

His Glu
   450

<210> SEQ ID NO 205
<211> LENGTH: 450
<212> TYPE: PRT
<213> ORGANISM: Artificial Sequence
<220> FEATURE:
<223> OTHER INFORMATION: CW6W35 (rhHLA-Cw6/ARFN)

<400> SEQUENCE: 205

Ala Arg Phe Asn Asp Leu Arg Phe Val Gly Gly Gly Ser Gly Gly
1               5                   10                  15

Gly Gly Ser Gly Gly Gly Ser Ile Gln Arg Thr Pro Lys Ile Gln
            20                  25                  30

Val Tyr Ser Arg His Pro Ala Glu Asn Gly Lys Ser Asn Phe Leu Asn
        35                  40                  45

Cys Tyr Val Ser Gly Phe His Pro Ser Asp Ile Glu Val Asp Leu Leu
    50                  55                  60
```

Lys Asn Gly Glu Arg Ile Glu Lys Val Glu His Ser Asp Leu Ser Phe
65                  70                  75                  80

Ser Lys Asp Trp Ser Phe Tyr Leu Leu Tyr Tyr Thr Glu Phe Thr Pro
            85                  90                  95

Thr Glu Lys Asp Glu Tyr Ala Cys Arg Val Asn His Val Thr Leu Ser
        100                 105                 110

Gln Pro Lys Ile Val Lys Trp Asp Arg Asp Met Gly Gly Gly Gly Ser
    115                 120                 125

Gly Gly Gly Gly Ser Gly Gly Gly Ser Gly Ser His Ser Met Arg
130                 135                 140

Tyr Phe Asp Thr Ala Val Ser Arg Pro Gly Arg Gly Glu Pro Arg Phe
145                 150                 155                 160

Ile Ser Val Gly Tyr Val Asp Asp Thr Gln Phe Val Arg Phe Asp Ser
                165                 170                 175

Asp Ala Ala Ser Pro Arg Gly Glu Pro Arg Ala Pro Trp Val Glu Gln
            180                 185                 190

Glu Gly Pro Glu Tyr Trp Asp Arg Glu Thr Gln Lys Tyr Lys Arg Gln
        195                 200                 205

Ala Gln Ala Asp Arg Val Asn Leu Arg Lys Leu Arg Gly Tyr Tyr Asn
    210                 215                 220

Gln Ser Glu Asp Gly Ser His Thr Leu Gln Trp Met Tyr Gly Cys Asp
225                 230                 235                 240

Leu Gly Pro Asp Gly Arg Leu Leu Arg Gly Tyr Asp Gln Ser Ala Tyr
                245                 250                 255

Asp Gly Lys Asp Tyr Ile Ala Leu Asn Glu Asp Leu Arg Ser Trp Thr
            260                 265                 270

Ala Ala Asp Thr Ala Ala Gln Ile Thr Gln Arg Lys Trp Glu Ala Ala
        275                 280                 285

Arg Glu Ala Glu Gln Trp Arg Ala Tyr Leu Glu Gly Thr Cys Val Glu
    290                 295                 300

Trp Leu Arg Arg Tyr Leu Glu Asn Gly Lys Glu Thr Leu Gln Arg Ala
305                 310                 315                 320

Glu His Pro Lys Thr His Val Thr His His Pro Val Ser Asp His Glu
                325                 330                 335

Ala Thr Leu Arg Cys Trp Ala Leu Gly Phe Tyr Pro Ala Glu Ile Thr
            340                 345                 350

Leu Thr Trp Gln Arg Asp Gly Glu Asp Gln Thr Gln Asp Thr Glu Leu
        355                 360                 365

Val Glu Thr Arg Pro Ala Gly Asp Gly Thr Phe Gln Lys Trp Ala Ala
    370                 375                 380

Val Val Val Pro Ser Gly Glu Glu Gln Arg Tyr Thr Cys His Val Gln
385                 390                 395                 400

His Glu Gly Leu Pro Glu Pro Leu Thr Leu Arg Trp Glu Pro Ser Ser
                405                 410                 415

Gln Pro Thr Ile Pro Ile Gly Gly Gly Ser His His His His His His
            420                 425                 430

His Gly Ser Gly Leu Asn Asp Ile Phe Glu Ala Gln Lys Ile Glu Trp
        435                 440                 445

His Glu
450

<210> SEQ ID NO 206
<211> LENGTH: 450

<212> TYPE: PRT
<213> ORGANISM: Artificial Sequence
<220> FEATURE:
<223> OTHER INFORMATION: CW6W47 (rhHLA-Cw6/NRRF)

<400> SEQUENCE: 206

```
Asn Arg Arg Phe Val Asn Val Val Pro Gly Gly Gly Ser Gly Gly
1               5                   10                  15

Gly Gly Ser Gly Gly Gly Ser Ile Gln Arg Thr Pro Lys Ile Gln
            20                  25                  30

Val Tyr Ser Arg His Pro Ala Glu Asn Gly Lys Ser Asn Phe Leu Asn
        35                  40                  45

Cys Tyr Val Ser Gly Phe His Pro Ser Asp Ile Glu Val Asp Leu Leu
    50                  55                  60

Lys Asn Gly Glu Arg Ile Glu Lys Val Glu His Ser Asp Leu Ser Phe
65                  70                  75                  80

Ser Lys Asp Trp Ser Phe Tyr Leu Leu Tyr Tyr Thr Glu Phe Thr Pro
                85                  90                  95

Thr Glu Lys Asp Glu Tyr Ala Cys Arg Val Asn His Val Thr Leu Ser
                100                 105                 110

Gln Pro Lys Ile Val Lys Trp Asp Arg Asp Met Gly Gly Gly Ser
            115                 120                 125

Gly Gly Gly Gly Ser Gly Gly Gly Ser Gly Ser His Ser Met Arg
    130                 135                 140

Tyr Phe His Thr Ser Val Ser Arg Pro Gly Arg Gly Glu Pro Arg Phe
145                 150                 155                 160

Ile Thr Val Gly Tyr Val Asp Asp Thr Gln Phe Val Arg Phe Asp Ser
                165                 170                 175

Asp Ala Ala Ser Pro Arg Glu Glu Pro Arg Ala Pro Trp Ile Glu Gln
            180                 185                 190

Glu Gly Pro Glu Tyr Trp Asp Arg Asn Thr Gln Ile Cys Lys Ala Lys
        195                 200                 205

Ala Gln Thr Asp Arg Val Gly Leu Arg Asn Leu Arg Gly Tyr Tyr Asn
    210                 215                 220

Gln Ser Glu Asp Gly Ser His Thr Trp Gln Thr Met Tyr Gly Cys Asp
225                 230                 235                 240

Met Gly Pro Asp Gly Arg Leu Leu Arg Gly Tyr Asn Gln Phe Ala Tyr
                245                 250                 255

Asp Gly Lys Asp Tyr Ile Ala Leu Asn Glu Asp Leu Arg Ser Trp Thr
            260                 265                 270

Ala Ala Asp Thr Ala Ala Gln Ile Thr Gln Arg Lys Trp Glu Ala Ala
        275                 280                 285

Arg Val Ala Glu Gln Leu Arg Ala Tyr Leu Glu Gly Glu Cys Val Glu
    290                 295                 300

Trp Leu Arg Arg His Leu Glu Asn Gly Lys Glu Thr Leu Gln Arg Ala
305                 310                 315                 320

Asp Pro Pro Lys Thr His Val Thr His His Pro Ile Ser Asp His Glu
                325                 330                 335

Ala Thr Leu Arg Cys Trp Ala Leu Gly Phe Tyr Pro Ala Glu Ile Thr
            340                 345                 350

Leu Thr Trp Gln Arg Asp Gly Glu Asp Gln Thr Gln Asp Thr Glu Leu
        355                 360                 365

Val Glu Thr Arg Pro Ala Gly Asp Gly Thr Phe Gln Lys Trp Ala Ala
    370                 375                 380
```

-continued

```
Val Val Val Pro Ser Gly Gln Glu Gln Arg Tyr Thr Cys His Val Gln
385                 390                 395                 400

His Glu Gly Leu Gln Glu Pro Cys Thr Leu Arg Trp Lys Pro Ser Ser
            405                 410                 415

Gln Ser Thr Ile Pro Ile Gly Gly Gly Ser His His His His
        420                 425                 430

His Gly Ser Gly Leu Asn Asp Ile Phe Glu Ala Gln Lys Ile Glu Trp
        435                 440                 445

His Glu
    450

<210> SEQ ID NO 207
<211> LENGTH: 450
<212> TYPE: PRT
<213> ORGANISM: Artificial Sequence
<220> FEATURE:
<223> OTHER INFORMATION: CW6W51 (rhHLA-Cw6/SRAS)

<400> SEQUENCE: 207

Ser Arg Ala Ser Pro Val Arg Leu Leu Gly Gly Gly Ser Gly Gly
1               5                   10                  15

Gly Gly Ser Gly Gly Gly Ser Ile Gln Arg Thr Pro Lys Ile Gln
            20                  25                  30

Val Tyr Ser Arg His Pro Ala Glu Asn Gly Lys Ser Asn Phe Leu Asn
        35                  40                  45

Cys Tyr Val Ser Gly Phe His Pro Ser Asp Ile Glu Val Asp Leu Leu
    50                  55                  60

Lys Asn Gly Glu Arg Ile Glu Lys Val Glu His Ser Asp Leu Ser Phe
65                  70                  75                  80

Ser Lys Asp Trp Ser Phe Tyr Leu Leu Tyr Tyr Thr Glu Phe Thr Pro
                85                  90                  95

Thr Glu Lys Asp Glu Tyr Ala Cys Arg Val Asn His Val Thr Leu Ser
            100                 105                 110

Gln Pro Lys Ile Val Lys Trp Asp Arg Asp Met Gly Gly Gly Gly Ser
        115                 120                 125

Gly Gly Gly Gly Ser Gly Gly Gly Ser Gly Ser His Ser Met Arg
    130                 135                 140

Tyr Phe Asp Thr Ala Val Ser Arg Pro Gly Arg Gly Glu Pro Arg Phe
145                 150                 155                 160

Ile Ser Val Gly Tyr Val Asp Asp Thr Gln Phe Val Arg Phe Asp Ser
                165                 170                 175

Asp Ala Ala Ser Pro Arg Gly Glu Pro Arg Ala Pro Trp Val Glu Gln
            180                 185                 190

Glu Gly Pro Glu Tyr Trp Asp Arg Glu Thr Gln Lys Tyr Lys Arg Gln
        195                 200                 205

Ala Gln Ala Asp Arg Val Asn Leu Arg Lys Leu Arg Gly Tyr Tyr Asn
    210                 215                 220

Gln Ser Glu Asp Gly Ser His Thr Leu Gln Trp Met Tyr Gly Cys Asp
225                 230                 235                 240

Leu Gly Pro Asp Gly Arg Leu Leu Arg Gly Tyr Asp Gln Ser Ala Tyr
                245                 250                 255

Asp Gly Lys Asp Tyr Ile Ala Leu Asn Glu Asp Leu Arg Ser Trp Thr
            260                 265                 270

Ala Ala Asp Thr Ala Ala Gln Ile Thr Gln Arg Lys Trp Glu Ala Ala
        275                 280                 285
```

```
Arg Glu Ala Glu Gln Trp Arg Ala Tyr Leu Glu Gly Thr Cys Val Glu
    290                 295                 300

Trp Leu Arg Arg Tyr Leu Glu Asn Gly Lys Glu Thr Leu Gln Arg Ala
305                 310                 315                 320

Glu His Pro Lys Thr His Val Thr His His Pro Val Ser Asp His Glu
                325                 330                 335

Ala Thr Leu Arg Cys Trp Ala Leu Gly Phe Tyr Pro Ala Glu Ile Thr
            340                 345                 350

Leu Thr Trp Gln Arg Asp Gly Glu Asp Gln Thr Gln Asp Thr Glu Leu
        355                 360                 365

Val Glu Thr Arg Pro Ala Gly Asp Gly Thr Phe Gln Lys Trp Ala Ala
370                 375                 380

Val Val Val Pro Ser Gly Glu Glu Gln Arg Tyr Thr Cys His Val Gln
385                 390                 395                 400

His Glu Gly Leu Pro Glu Pro Leu Thr Leu Arg Trp Glu Pro Ser Ser
                405                 410                 415

Gln Pro Thr Ile Pro Ile Gly Gly Gly Ser His His His His
            420                 425                 430

His Gly Ser Gly Leu Asn Asp Ile Phe Glu Ala Gln Lys Ile Glu Trp
        435                 440                 445

His Glu
    450

<210> SEQ ID NO 208
<211> LENGTH: 450
<212> TYPE: PRT
<213> ORGANISM: Artificial Sequence
<220> FEATURE:
<223> OTHER INFORMATION: CW6W53 (rhHLA-Cw6/LRAA)

<400> SEQUENCE: 208

Leu Arg Ala Ala Leu Gln Arg Ser Leu Gly Gly Gly Ser Gly Gly
1               5                   10                  15

Gly Gly Ser Gly Gly Gly Ser Ile Gln Arg Thr Pro Lys Ile Gln
            20                  25                  30

Val Tyr Ser Arg His Pro Ala Glu Asn Gly Lys Ser Asn Phe Leu Asn
            35                  40                  45

Cys Tyr Val Ser Gly Phe His Pro Ser Asp Ile Glu Val Asp Leu Leu
50                  55                  60

Lys Asn Gly Glu Arg Ile Glu Lys Val Glu His Ser Asp Leu Ser Phe
65                  70                  75                  80

Ser Lys Asp Trp Ser Phe Tyr Leu Leu Tyr Tyr Thr Glu Phe Thr Pro
            85                  90                  95

Thr Glu Lys Asp Glu Tyr Ala Cys Arg Val Asn His Val Thr Leu Ser
            100                 105                 110

Gln Pro Lys Ile Val Lys Trp Asp Arg Asp Met Gly Gly Gly Gly Ser
        115                 120                 125

Gly Gly Gly Gly Ser Gly Gly Gly Ser Gly Ser His Ser Met Arg
    130                 135                 140

Tyr Phe Asp Thr Ala Val Ser Arg Pro Gly Arg Gly Glu Pro Arg Phe
145                 150                 155                 160

Ile Ser Val Gly Tyr Val Asp Asp Thr Gln Phe Val Arg Phe Asp Ser
            165                 170                 175

Asp Ala Ala Ser Pro Arg Gly Glu Pro Arg Ala Pro Trp Val Glu Gln
        180                 185                 190
```

```
Glu Gly Pro Glu Tyr Trp Asp Arg Glu Thr Gln Lys Tyr Lys Arg Gln
            195                 200                 205

Ala Gln Ala Asp Arg Val Asn Leu Arg Lys Leu Arg Gly Tyr Tyr Asn
210                 215                 220

Gln Ser Glu Asp Gly Ser His Thr Leu Gln Trp Met Tyr Gly Cys Asp
225                 230                 235                 240

Leu Gly Pro Asp Gly Arg Leu Leu Arg Gly Tyr Asp Gln Ser Ala Tyr
                245                 250                 255

Asp Gly Lys Asp Tyr Ile Ala Leu Asn Glu Asp Leu Arg Ser Trp Thr
            260                 265                 270

Ala Ala Asp Thr Ala Ala Gln Ile Thr Gln Arg Lys Trp Glu Ala Ala
        275                 280                 285

Arg Glu Ala Glu Gln Trp Arg Ala Tyr Leu Glu Gly Thr Cys Val Glu
    290                 295                 300

Trp Leu Arg Arg Tyr Leu Glu Asn Gly Lys Glu Thr Leu Gln Arg Ala
305                 310                 315                 320

Glu His Pro Lys Thr His Val Thr His His Pro Val Ser Asp His Glu
                325                 330                 335

Ala Thr Leu Arg Cys Trp Ala Leu Gly Phe Tyr Pro Ala Glu Ile Thr
            340                 345                 350

Leu Thr Trp Gln Arg Asp Gly Glu Asp Gln Thr Gln Asp Thr Glu Leu
        355                 360                 365

Val Glu Thr Arg Pro Ala Gly Asp Gly Thr Phe Gln Lys Trp Ala Ala
    370                 375                 380

Val Val Val Pro Ser Gly Glu Glu Gln Arg Tyr Thr Cys His Val Gln
385                 390                 395                 400

His Glu Gly Leu Pro Glu Pro Leu Thr Leu Arg Trp Glu Pro Ser Ser
                405                 410                 415

Gln Pro Thr Ile Pro Ile Gly Gly Gly Ser His His His His His His
            420                 425                 430

His Gly Ser Gly Leu Asn Asp Ile Phe Glu Ala Gln Lys Ile Glu Trp
        435                 440                 445

His Glu
    450

<210> SEQ ID NO 209
<211> LENGTH: 427
<212> TYPE: PRT
<213> ORGANISM: Artificial Sequence
<220> FEATURE:
<223> OTHER INFORMATION: CW6W55 (rhHLA-B46)

<400> SEQUENCE: 209

Met Ile Gln Arg Thr Pro Lys Ile Gln Val Tyr Ser Arg His Pro Ala
1               5                   10                  15

Glu Asn Gly Lys Ser Asn Phe Leu Asn Cys Tyr Val Ser Gly Phe His
            20                  25                  30

Pro Ser Asp Ile Glu Val Asp Leu Leu Lys Asn Gly Glu Arg Ile Glu
        35                  40                  45

Lys Val Glu His Ser Asp Leu Ser Phe Ser Lys Asp Trp Ser Phe Tyr
    50                  55                  60

Leu Leu Tyr Tyr Thr Glu Phe Thr Pro Thr Glu Lys Asp Glu Tyr Ala
65                  70                  75                  80

Cys Arg Val Asn His Val Thr Leu Ser Gln Pro Lys Ile Val Lys Trp
                85                  90                  95
```

```
Asp Arg Asp Met Gly Gly Gly Ser Gly Gly Gly Ser Gly Gly
            100                 105                 110

Gly Gly Ser Gly Ser His Ser Met Arg Tyr Phe Tyr Thr Ala Met Ser
        115                 120                 125

Arg Pro Gly Arg Gly Glu Pro Arg Phe Ile Ala Val Gly Tyr Val Asp
    130                 135                 140

Asp Thr Gln Phe Val Arg Phe Asp Ser Asp Ala Ala Ser Pro Arg Met
145                 150                 155                 160

Ala Pro Arg Ala Pro Trp Ile Glu Gln Glu Gly Pro Glu Tyr Trp Asp
                165                 170                 175

Arg Glu Thr Gln Lys Tyr Lys Arg Gln Ala Gln Thr Asp Arg Val Ser
            180                 185                 190

Leu Arg Asn Leu Arg Gly Tyr Tyr Asn Gln Ser Glu Ala Gly Ser His
        195                 200                 205

Thr Leu Gln Arg Met Tyr Gly Cys Asp Val Gly Pro Asp Gly Arg Leu
    210                 215                 220

Leu Arg Gly His Asp Gln Ser Ala Tyr Asp Gly Lys Asp Tyr Ile Ala
225                 230                 235                 240

Leu Asn Glu Asp Leu Ser Ser Trp Thr Ala Ala Asp Thr Ala Ala Gln
                245                 250                 255

Ile Thr Gln Arg Lys Trp Glu Ala Ala Arg Glu Ala Glu Gln Trp Arg
            260                 265                 270

Ala Tyr Leu Glu Gly Leu Cys Val Glu Trp Leu Arg Arg Tyr Leu Glu
        275                 280                 285

Asn Gly Lys Glu Thr Leu Gln Arg Ala Asp Pro Pro Lys Thr His Val
    290                 295                 300

Thr His His Pro Ile Ser Asp His Glu Ala Thr Leu Arg Cys Trp Ala
305                 310                 315                 320

Leu Gly Phe Tyr Pro Ala Glu Ile Thr Leu Thr Trp Gln Arg Asp Gly
                325                 330                 335

Glu Asp Gln Thr Gln Asp Thr Glu Leu Val Glu Thr Arg Pro Ala Gly
            340                 345                 350

Asp Arg Thr Phe Gln Lys Trp Ala Ala Val Val Val Pro Ser Gly Glu
        355                 360                 365

Glu Gln Arg Tyr Thr Cys His Val Gln His Glu Gly Leu Pro Lys Pro
    370                 375                 380

Leu Thr Leu Arg Trp Glu Pro Ser Ser Gln Ser Thr Ile Pro Ile Gly
385                 390                 395                 400

Gly Gly Gly Ser His His His His His Gly Ser Gly Leu Asn Asp
                405                 410                 415

Ile Phe Glu Ala Gln Lys Ile Glu Trp His Glu
            420                 425

<210> SEQ ID NO 210
<211> LENGTH: 427
<212> TYPE: PRT
<213> ORGANISM: Artificial Sequence
<220> FEATURE:
<223> OTHER INFORMATION: CW6W55 (rhHLA-B73)

<400> SEQUENCE: 210

Met Ile Gln Arg Thr Pro Lys Ile Gln Val Tyr Ser Arg His Pro Ala
1               5                   10                  15

Glu Asn Gly Lys Ser Asn Phe Leu Asn Cys Tyr Val Ser Gly Phe His
            20                  25                  30
```

Pro Ser Asp Ile Glu Val Asp Leu Lys Asn Gly Glu Arg Ile Glu
             35                  40                  45

Lys Val Glu His Ser Asp Leu Ser Phe Ser Lys Asp Trp Ser Phe Tyr
 50                  55                  60

Leu Leu Tyr Tyr Thr Glu Phe Thr Pro Thr Glu Lys Asp Glu Tyr Ala
 65                  70                  75                  80

Cys Arg Val Asn His Val Thr Leu Ser Gln Pro Lys Ile Val Lys Trp
                 85                  90                  95

Asp Arg Asp Met Gly Gly Gly Gly Ser Gly Gly Gly Ser Gly Gly
                100                 105                 110

Gly Gly Ser Gly Ser His Ser Met Arg Tyr Phe His Thr Ser Val Ser
             115                 120                 125

Arg Pro Gly Arg Gly Glu Pro Arg Phe Ile Thr Val Gly Tyr Val Asp
 130                 135                 140

Asp Thr Gln Phe Val Arg Phe Asp Ser Asp Ala Ala Ser Pro Arg Glu
 145                 150                 155                 160

Glu Pro Arg Ala Pro Trp Ile Glu Gln Glu Gly Pro Glu Tyr Trp Asp
                 165                 170                 175

Arg Asn Thr Gln Ile Cys Lys Ala Lys Ala Gln Thr Asp Arg Val Gly
             180                 185                 190

Leu Arg Asn Leu Arg Gly Tyr Tyr Asn Gln Ser Glu Asp Gly Ser His
 195                 200                 205

Thr Trp Gln Thr Met Tyr Gly Cys Asp Met Gly Pro Asp Gly Arg Leu
 210                 215                 220

Leu Arg Gly Tyr Asn Gln Phe Ala Tyr Asp Gly Lys Asp Tyr Ile Ala
225                 230                 235                 240

Leu Asn Glu Asp Leu Arg Ser Trp Thr Ala Ala Asp Thr Ala Ala Gln
             245                 250                 255

Ile Thr Gln Arg Lys Trp Glu Ala Ala Arg Val Ala Glu Gln Leu Arg
             260                 265                 270

Ala Tyr Leu Glu Gly Glu Cys Val Glu Trp Leu Arg Arg His Leu Glu
             275                 280                 285

Asn Gly Lys Glu Thr Leu Gln Arg Ala Asp Pro Pro Lys Thr His Val
 290                 295                 300

Thr His His Pro Ile Ser Asp His Glu Ala Thr Leu Arg Cys Trp Ala
305                 310                 315                 320

Leu Gly Phe Tyr Pro Ala Glu Ile Thr Leu Thr Trp Gln Arg Asp Gly
             325                 330                 335

Glu Asp Gln Thr Gln Asp Thr Glu Leu Val Glu Thr Arg Pro Ala Gly
             340                 345                 350

Asp Gly Thr Phe Gln Lys Trp Ala Ala Val Val Val Pro Ser Gly Gln
             355                 360                 365

Glu Gln Arg Tyr Thr Cys His Val Gln His Glu Gly Leu Gln Glu Pro
 370                 375                 380

Cys Thr Leu Arg Trp Lys Pro Ser Ser Gln Ser Thr Ile Pro Ile Gly
385                 390                 395                 400

Gly Gly Gly Ser His His His His His Gly Ser Gly Leu Asn Asp
             405                 410                 415

Ile Phe Glu Ala Gln Lys Ile Glu Trp His Glu
             420                 425

<210> SEQ ID NO 211
<211> LENGTH: 342
<212> TYPE: PRT

<213> ORGANISM: Artificial Sequence
<220> FEATURE:
<223> OTHER INFORMATION: rhHLA-Cw6

<400> SEQUENCE: 211

```
Cys Ser His Ser Met Arg Tyr Phe Asp Thr Ala Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Gly Glu Pro Arg
        35                  40                  45

Ala Pro Trp Val Glu Gln Glu Gly Pro Glu Tyr Trp Asp Arg Glu Thr
50                  55                  60

Gln Lys Tyr Lys Arg Gln Ala Gln Ala Asp Arg Val Asn Leu Arg Lys
65                  70                  75                  80

Leu Arg Gly Tyr Tyr Asn Gln Ser Glu Asp Gly Ser His Thr Leu Gln
                85                  90                  95

Trp Met Tyr Gly Cys Asp Leu Gly Pro Asp Gly Arg Leu Leu Arg Gly
            100                 105                 110

Tyr Asp Gln Ser Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
130                 135                 140

Arg Lys Trp Glu Ala Ala Arg Glu Ala Glu Gln Trp Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Ala Glu His Pro Lys Thr His Val Thr His His
            180                 185                 190

Pro Val Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Pro Ser Gly Glu Glu Gln Arg
                245                 250                 255

Tyr Thr Cys His Val Gln His Glu Gly Leu Pro Glu Pro Leu Thr Leu
            260                 265                 270

Arg Trp Glu Pro Ser Ser Gln Pro Thr Ile Pro Ile Val Gly Ile Val
        275                 280                 285

Ala Gly Leu Ala Val Leu Ala Val Leu Ala Val Leu Gly Ala Val Met
290                 295                 300

Ala Val Val Met Cys Arg Arg Lys Ser Ser Gly Gly Lys Gly Gly Ser
305                 310                 315                 320

Cys Ser Gln Ala Ala Ser Ser Asn Ser Ala Gln Gly Ser Asp Glu Ser
                325                 330                 335

Leu Ile Ala Cys Lys Ala
            340
```

<210> SEQ ID NO 212
<211> LENGTH: 341
<212> TYPE: PRT
<213> ORGANISM: Artificial Sequence
<220> FEATURE:
<223> OTHER INFORMATION: rhHLA-A1

<400> SEQUENCE: 212

```
Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Lys Met Glu Pro Arg
        35                  40                  45

Ala Pro Trp Ile Glu Gln Glu Gly Pro Glu Tyr Trp Asp Gln Glu Thr
50                  55                  60

Arg Asn Met Lys Ala His Ser Gln Thr Asp Arg Ala Asn Leu Gly Thr
65                  70                  75                  80

Leu Arg Gly Tyr Tyr Asn Gln Ser Glu Asp Gly Ser His Thr Ile Gln
                85                  90                  95

Ile Met Tyr Gly Cys Asp Val Gly Pro Asp Gly Arg Phe Leu Arg Gly
            100                 105                 110

Tyr Arg Gln Asp Ala Tyr Asp Gly Lys Asp Tyr Ile Ala Leu Asn Glu
        115                 120                 125

Asp Leu Arg Ser Trp Thr Ala Ala Asp Met Ala Ala Gln Ile Thr Lys
130                 135                 140

Arg Lys Trp Glu Ala Val His Ala Ala Glu Gln Arg Arg Val Tyr Leu
145                 150                 155                 160

Glu Gly Arg Cys Val Asp Gly Leu Arg Arg Tyr Leu Glu Asn Gly Lys
                165                 170                 175

Glu Thr Leu Gln Arg Thr Asp Pro Pro Lys Thr His Met Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Leu Ser Ser Gln Pro Thr Ile Pro Ile Val Gly Ile Ile
        275                 280                 285

Ala Gly Leu Val Leu Leu Gly Ala Val Ile Thr Gly Ala Val Val Ala
290                 295                 300

Ala Val Met Trp Arg Arg Lys Ser Ser Asp Arg Lys Gly Gly Ser Tyr
305                 310                 315                 320

Thr Gln Ala Ala Ser Ser Asp Ser Ala Gln Gly Ser Asp Val Ser Leu
                325                 330                 335

Thr Ala Cys Lys Val
            340
```

<210> SEQ ID NO 213
<211> LENGTH: 362
<212> TYPE: PRT
<213> ORGANISM: Artificial Sequence
<220> FEATURE:
<223> OTHER INFORMATION: rhHLA-B7

<400> SEQUENCE: 213

```
Met Leu Val Met Ala Pro Arg Thr Val Leu Leu Leu Ser Ala Ala
1               5                   10                  15

Leu Ala Leu Thr Glu Thr Trp Ala Gly Ser His Ser Met Arg Tyr Phe
            20                  25                  30

Tyr Thr Ser Val Ser Arg Pro Gly Arg Gly Glu Pro Arg Phe Ile Ser
            35                  40                  45

Val Gly Tyr Val Asp Asp Thr Gln Phe Val Arg Phe Asp Ser Asp Ala
        50                  55                  60

Ala Ser Pro Arg Glu Glu Pro Arg Ala Pro Trp Ile Glu Gln Glu Gly
65                  70                  75                  80

Pro Glu Tyr Trp Asp Arg Asn Thr Gln Ile Tyr Lys Ala Gln Ala Gln
                    85                  90                  95

Thr Asp Arg Glu Ser Leu Arg Asn Leu Arg Gly Tyr Tyr Asn Gln Ser
                100                 105                 110

Glu Ala Gly Ser His Thr Leu Gln Ser Met Tyr Gly Cys Asp Val Gly
                115                 120                 125

Pro Asp Gly Arg Leu Leu Arg Gly His Asp Gln Tyr Ala Tyr Asp Gly
            130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Trp Glu Ala Ala Arg Glu
                    165                 170                 175

Ala Glu Gln Arg Arg Ala Tyr Leu Glu Gly Glu Cys Val Glu Trp Leu
                180                 185                 190

Arg Arg Tyr Leu Glu Asn Gly Lys Asp Lys Leu Glu Arg Ala Asp Pro
                195                 200                 205

Pro Lys Thr His Val Thr His His Pro Ile Ser Asp His Glu Ala Thr
            210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                    245                 250                 255

Thr Arg Pro Ala Gly Asp Arg Thr Phe Gln Lys Trp Ala Ala Val Val
                260                 265                 270

Val Pro Ser Gly Glu Glu Gln Arg Tyr Thr Cys His Val Gln His Glu
            275                 280                 285

Gly Leu Pro Lys Pro Leu Thr Leu Arg Trp Glu Pro Ser Ser Gln Ser
        290                 295                 300

Thr Val Pro Ile Val Gly Ile Val Ala Gly Leu Ala Val Leu Ala Val
305                 310                 315                 320

Val Val Ile Gly Ala Val Val Ala Ala Val Met Cys Arg Arg Lys Ser
                325                 330                 335

Ser Gly Gly Lys Gly Gly Ser Tyr Ser Gln Ala Ala Cys Ser Asp Ser
                340                 345                 350

Ala Gln Gly Ser Asp Val Ser Leu Thr Ala
                355                 360

<210> SEQ ID NO 214
<211> LENGTH: 255
<212> TYPE: PRT
<213> ORGANISM: Artificial Sequence
<220> FEATURE:
<223> OTHER INFORMATION: ADAMTSL5 TCR alpha

<400> SEQUENCE: 214
```

Gln Gln Gly Glu Glu Asp Pro Gln Ala Leu Ser Ile Gln Glu Gly Glu
1               5                   10                  15

Asn Ala Thr Met Asn Cys Ser Tyr Lys Thr Ser Ile Asn Asn Leu Gln
            20                  25                  30

Trp Tyr Arg Gln Asn Ser Gly Arg Gly Leu Val His Leu Ile Leu Ile
        35                  40                  45

Arg Ser Asn Glu Arg Glu Lys His Ser Gly Arg Leu Arg Val Thr Leu
    50                  55                  60

Asp Thr Ser Lys Lys Ser Ser Leu Leu Ile Thr Ala Ser Arg Ala
65                  70                  75                  80

Ala Asp Thr Ala Ser Tyr Phe Cys Ala Thr Asp Ala Leu Tyr Ser Gly
                85                  90                  95

Gly Gly Ala Asp Gly Leu Thr Phe Gly Lys Gly Thr His Leu Ile Ile
            100                 105                 110

Gln Pro Tyr Ile Gln Asn Pro Asp Pro Ala Val Tyr Gln Leu Arg Asp
        115                 120                 125

Ser Lys Ser Ser Asp Lys Ser Val Cys Leu Phe Thr Asp Phe Asp Ser
    130                 135                 140

Gln Thr Asn Val Ser Gln Ser Lys Asp Ser Asp Val Tyr Ile Thr Asp
145                 150                 155                 160

Lys Thr Val Leu Asp Met Arg Ser Met Asp Phe Lys Ser Asn Ser Ala
                165                 170                 175

Val Ala Trp Ser Asn Lys Ser Asp Phe Ala Cys Ala Asn Ala Phe Asn
            180                 185                 190

Asn Ser Ile Ile Pro Glu Asp Thr Phe Phe Pro Ser Pro Glu Ser Ser
        195                 200                 205

Cys Asp Val Lys Leu Val Glu Lys Ser Phe Glu Thr Asp Thr Asn Leu
    210                 215                 220

Asn Phe Gln Asn Leu Ser Val Ile Gly Phe Arg Ile Leu Leu Leu Lys
225                 230                 235                 240

Val Ala Gly Phe Asn Leu Leu Met Thr Leu Arg Leu Trp Ser Ser
                245                 250                 255

<210> SEQ ID NO 215
<211> LENGTH: 309
<212> TYPE: PRT
<213> ORGANISM: Artificial Sequence
<220> FEATURE:
<223> OTHER INFORMATION: ADAMTSL5 TCR beta

<400> SEQUENCE: 215

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

```
Ser Tyr Ser Glu Gly Glu Asp Glu Ala Phe Phe Gly Gln Gly Thr Arg
            115                 120                 125
Leu Thr Val Val Glu Asp Leu Asn Lys Val Phe Pro Pro Glu Val Ala
130                 135                 140
Val Phe Glu Pro Ser Glu Ala Glu Ile Ser His Thr Gln Lys Ala Thr
145                 150                 155                 160
Leu Val Cys Leu Ala Thr Gly Phe Phe Pro Asp His Val Glu Leu Ser
            165                 170                 175
Trp Trp Val Asn Gly Lys Glu Val His Ser Gly Val Ser Thr Asp Pro
            180                 185                 190
Gln Pro Leu Lys Glu Gln Pro Ala Leu Asn Asp Ser Arg Tyr Cys Leu
            195                 200                 205
Ser Ser Arg Leu Arg Val Ser Ala Thr Phe Trp Gln Asn Pro Arg Asn
210                 215                 220
His Phe Arg Cys Gln Val Gln Phe Tyr Gly Leu Ser Glu Asn Asp Glu
225                 230                 235                 240
Trp Thr Gln Asp Arg Ala Lys Pro Val Thr Gln Ile Val Ser Ala Glu
            245                 250                 255
Ala Trp Gly Arg Ala Asp Cys Gly Phe Thr Ser Val Ser Tyr Gln Gln
            260                 265                 270
Gly Val Leu Ser Ala Thr Ile Leu Tyr Glu Ile Leu Leu Gly Lys Ala
            275                 280                 285
Thr Leu Tyr Ala Val Leu Val Ser Ala Leu Val Leu Met Ala Met Val
            290                 295                 300
Lys Arg Lys Asp Phe
305

<210> SEQ ID NO 216
<211> LENGTH: 235
<212> TYPE: PRT
<213> ORGANISM: Artificial Sequence
<220> FEATURE:
<223> OTHER INFORMATION: CD8 alpha

<400> SEQUENCE: 216

Met Ala Leu Pro Val Thr Ala Leu Leu Leu Pro Leu Ala Leu Leu Leu
1               5                   10                  15
His Ala Ala Arg Pro Ser Gln Phe Arg Val Ser Pro Leu Asp Arg Thr
            20                  25                  30
Trp Asn Leu Gly Glu Thr Val Glu Leu Lys Cys Gln Val Leu Leu Ser
            35                  40                  45
Asn Pro Thr Ser Gly Cys Ser Trp Leu Phe Gln Pro Arg Gly Ala Ala
50                  55                  60
Ala Ser Pro Thr Phe Leu Leu Tyr Leu Ser Gln Asn Lys Pro Lys Ala
65                  70                  75                  80
Ala Glu Gly Leu Asp Thr Gln Arg Phe Ser Gly Lys Arg Leu Gly Asp
            85                  90                  95
Thr Phe Val Leu Thr Leu Ser Asp Phe Arg Arg Glu Asn Glu Gly Tyr
            100                 105                 110
Tyr Phe Cys Ser Ala Leu Ser Asn Ser Ile Met Tyr Phe Ser His Phe
            115                 120                 125
Val Pro Val Phe Leu Pro Ala Lys Pro Thr Thr Thr Pro Ala Pro Arg
            130                 135                 140
Pro Pro Thr Pro Ala Pro Thr Ile Ala Ser Gln Pro Leu Ser Leu Arg
145                 150                 155                 160
```

```
Pro Glu Ala Cys Arg Pro Ala Gly Gly Ala Val His Thr Arg Gly
            165                 170                 175

Leu Asp Phe Ala Cys Asp Ile Tyr Ile Trp Ala Pro Leu Ala Gly Thr
            180                 185                 190

Cys Gly Val Leu Leu Ser Leu Val Ile Thr Leu Tyr Cys Asn His
            195                 200                 205

Arg Asn Arg Arg Val Cys Lys Cys Pro Arg Pro Val Val Lys Ser
    210                 215                 220

Gly Asp Lys Pro Ser Leu Ser Ala Arg Tyr Val
225                 230                 235

<210> SEQ ID NO 217
<211> LENGTH: 210
<212> TYPE: PRT
<213> ORGANISM: Artificial Sequence
<220> FEATURE:
<223> OTHER INFORMATION: CD8 beta

<400> SEQUENCE: 217

Met Arg Pro Arg Leu Trp Leu Leu Leu Ala Ala Gln Leu Thr Val Leu
1               5                   10                  15

His Gly Asn Ser Val Leu Gln Gln Thr Pro Ala Tyr Ile Lys Val Gln
            20                  25                  30

Thr Asn Lys Met Val Met Leu Ser Cys Glu Ala Lys Ile Ser Leu Ser
        35                  40                  45

Asn Met Arg Ile Tyr Trp Leu Arg Gln Arg Gln Ala Pro Ser Ser Asp
    50                  55                  60

Ser His His Glu Phe Leu Ala Leu Trp Asp Ser Ala Lys Gly Thr Ile
65                  70                  75                  80

His Gly Glu Glu Val Glu Gln Glu Lys Ile Ala Val Phe Arg Asp Ala
                85                  90                  95

Ser Arg Phe Ile Leu Asn Leu Thr Ser Val Lys Pro Glu Asp Ser Gly
            100                 105                 110

Ile Tyr Phe Cys Met Ile Val Gly Ser Pro Glu Leu Thr Phe Gly Lys
        115                 120                 125

Gly Thr Gln Leu Ser Val Val Asp Phe Leu Pro Thr Thr Ala Gln Pro
    130                 135                 140

Thr Lys Lys Ser Thr Leu Lys Lys Arg Val Cys Arg Leu Pro Arg Pro
145                 150                 155                 160

Glu Thr Gln Lys Gly Pro Leu Cys Ser Pro Ile Thr Leu Gly Leu Leu
                165                 170                 175

Val Ala Gly Val Leu Val Leu Leu Val Ser Leu Gly Val Ala Ile His
            180                 185                 190

Leu Cys Cys Arg Arg Arg Arg Ala Arg Leu Arg Phe Met Lys Gln Phe
        195                 200                 205

Tyr Lys
    210

<210> SEQ ID NO 218
<211> LENGTH: 10
<212> TYPE: PRT
<213> ORGANISM: Artificial Sequence
<220> FEATURE:
<223> OTHER INFORMATION: ADAMTSL5-Abu-HLA-Cw6
<220> FEATURE:
<221> NAME/KEY: MISC_FEATURE
<222> LOCATION: (7)..(7)
<223> OTHER INFORMATION: Alanine, wherein the alanine is a homoalanine
      (alpha-aminobutyric acid (alpha-Abu))
```

```
<400> SEQUENCE: 218

Val Arg Ser Arg Arg Leu Ala Leu Arg Leu
1               5                   10

<210> SEQ ID NO 219
<211> LENGTH: 9
<212> TYPE: PRT
<213> ORGANISM: Artificial Sequence
<220> FEATURE:
<223> OTHER INFORMATION: ARFN-HLA-Cw6

<400> SEQUENCE: 219

Ala Arg Phe Asn Asp Leu Arg Phe Val
1               5

<210> SEQ ID NO 220
<211> LENGTH: 9
<212> TYPE: PRT
<213> ORGANISM: Artificial Sequence
<220> FEATURE:
<223> OTHER INFORMATION: TRAT-HLA-Cw6

<400> SEQUENCE: 220

Thr Arg Ala Thr Lys Met Gln Val Ile
1               5

<210> SEQ ID NO 221
<211> LENGTH: 9
<212> TYPE: PRT
<213> ORGANISM: Artificial Sequence
<220> FEATURE:
<223> OTHER INFORMATION: FIIQ-HLA-B46

<400> SEQUENCE: 221

Phe Ile Ile Gln Gly Leu Arg Ser Val
1               5

<210> SEQ ID NO 222
<211> LENGTH: 9
<212> TYPE: PRT
<213> ORGANISM: Artificial Sequence
<220> FEATURE:
<223> OTHER INFORMATION: ILGP-HLA-B46

<400> SEQUENCE: 222

Ile Leu Gly Pro Pro Gly Ser Val Tyr
1               5

<210> SEQ ID NO 223
<211> LENGTH: 8
<212> TYPE: PRT
<213> ORGANISM: Artificial Sequence
<220> FEATURE:
<223> OTHER INFORMATION: TSSY-HLA-B46

<400> SEQUENCE: 223

Thr Ser Ser Tyr Lys Pro Ile Val
1               5

<210> SEQ ID NO 224
<211> LENGTH: 9
<212> TYPE: PRT
<213> ORGANISM: Artificial Sequence
<220> FEATURE:
<223> OTHER INFORMATION: NRRF-HLA-B73
```

-continued

<400> SEQUENCE: 224

Asn Arg Arg Phe Val Asn Val Val Pro
1               5

<210> SEQ ID NO 225
<211> LENGTH: 275
<212> TYPE: PRT
<213> ORGANISM: Artificial Sequence
<220> FEATURE:
<223> OTHER INFORMATION: 2G8_TRAV5

<400> SEQUENCE: 225

Met Lys Thr Phe Ala Gly Phe Ser Phe Leu Phe Leu Trp Leu Gln Leu
1               5                   10                  15

Asp Cys Met Ser Arg Gly Glu Asp Val Glu Gln Ser Leu Phe Leu Ser
            20                  25                  30

Val Arg Glu Gly Asp Ser Ser Val Ile Asn Cys Thr Tyr Thr Asp Ser
        35                  40                  45

Ser Ser Thr Tyr Leu Tyr Trp Tyr Lys Gln Glu Pro Gly Ala Gly Leu
    50                  55                  60

Gln Leu Leu Thr Tyr Ile Phe Ser Asn Met Asp Met Lys Gln Asp Gln
65                  70                  75                  80

Arg Leu Thr Val Leu Leu Asn Lys Lys Asp Lys His Leu Ser Leu Arg
                85                  90                  95

Ile Ala Asp Thr Gln Thr Gly Asp Ser Ala Ile Tyr Phe Cys Ala Glu
            100                 105                 110

Ser Ser Asn Leu Ser Gly Asn Thr Pro Leu Val Phe Gly Lys Gly Thr
        115                 120                 125

Arg Leu Ser Val Ile Ala Asn Ile Gln Asn Pro Asp Pro Ala Val Tyr
    130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
    210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser
        275

<210> SEQ ID NO 226
<211> LENGTH: 321
<212> TYPE: PRT
<213> ORGANISM: Artificial Sequence
<220> FEATURE:
<223> OTHER INFORMATION: 2G8-1D3_TRBV13*01

<400> SEQUENCE: 226

```
Met Leu Ser Pro Asp Leu Pro Asp Ser Ala Trp Asn Thr Arg Leu Leu
1               5                   10                  15

Cys His Val Met Leu Cys Leu Leu Gly Ala Val Ser Val Ala Ala Gly
            20                  25                  30

Val Ile Gln Ser Pro Arg His Leu Ile Lys Glu Lys Arg Glu Thr Ala
            35                  40                  45

Thr Leu Lys Cys Tyr Pro Ile Pro Arg His Asp Thr Val Tyr Trp Tyr
        50                  55                  60

Gln Gln Gly Pro Gly Gln Asp Pro Gln Phe Leu Ile Ser Phe Tyr Glu
65                  70                  75                  80

Lys Met Gln Ser Asp Lys Gly Ser Ile Pro Asp Arg Phe Ser Ala Gln
            85                  90                  95

Gln Phe Ser Asp Tyr His Ser Glu Leu Asn Met Ser Ser Leu Glu Leu
            100                 105                 110

Gly Asp Ser Ala Leu Tyr Phe Cys Ala Ser Gly Leu Ala Gly Ile Thr
            115                 120                 125

Gly Glu Leu Phe Phe Gly Glu Gly Ser Arg Leu Thr Val Leu Glu Asp
        130                 135                 140

Leu Lys Asn Val Phe Pro Pro Glu Val Ala Val Phe Glu Pro Ser Glu
145                 150                 155                 160

Ala Glu Ile Ser His Thr Gln Lys Ala Thr Leu Val Cys Leu Ala Thr
            165                 170                 175

Gly Phe Tyr Pro Asp His Val Glu Leu Ser Trp Trp Val Asn Gly Lys
            180                 185                 190

Glu Val His Ser Gly Val Ser Thr Asp Pro Gln Pro Leu Lys Glu Gln
            195                 200                 205

Pro Ala Leu Asn Asp Ser Arg Tyr Cys Leu Ser Ser Arg Leu Arg Val
        210                 215                 220

Ser Ala Thr Phe Trp Gln Asn Pro Arg Asn His Phe Arg Cys Gln Val
225                 230                 235                 240

Gln Phe Tyr Gly Leu Ser Glu Asn Asp Glu Trp Thr Gln Asp Arg Ala
            245                 250                 255

Lys Pro Val Thr Gln Ile Val Ser Ala Glu Ala Trp Gly Arg Ala Asp
            260                 265                 270

Cys Gly Phe Thr Ser Glu Ser Tyr Gln Gln Gly Val Leu Ser Ala Thr
            275                 280                 285

Ile Leu Tyr Glu Ile Leu Leu Gly Lys Ala Thr Leu Tyr Ala Val Leu
        290                 295                 300

Val Ser Ala Leu Val Leu Met Ala Met Val Lys Arg Lys Asp Ser Arg
305                 310                 315                 320

Gly
```